US007300920B2

(12) United States Patent
Weiner et al.

(10) Patent No.: US 7,300,920 B2
(45) Date of Patent: Nov. 27, 2007

(54) ANTIANGIOGENIC PEPTIDE AGENTS

(75) Inventors: Richard I. Weiner, Muir Beach, CA (US); Joseph A. Martial, Esneux (BE); Ingrid Struman, Faimes (BE); Robert Taylor, San Francisco, CA (US); Frauke Bentzien, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 413 days.

(21) Appl. No.: 10/714,067

(22) Filed: Nov. 14, 2003

(65) Prior Publication Data

US 2004/0077054 A1 Apr. 22, 2004

Related U.S. Application Data

(63) Continuation of application No. 09/819,094, filed on Mar. 27, 2001, now abandoned, which is a continuation of application No. 09/076,675, filed on May 12, 1998, now abandoned.

(60) Provisional application No. 60/046,394, filed on May 13, 1997.

(51) Int. Cl.
*A61K 38/18* (2006.01)
*A61K 31/27* (2006.01)
*C07K 14/475* (2006.01)
*C07K 14/61* (2006.01)

(52) U.S. Cl. .................. 514/12; 530/399; 530/300
(58) Field of Classification Search ................ None
See application file for complete search history.

(56) References Cited

U.S. PATENT DOCUMENTS

| 4,189,426 | A | * | 2/1980 | Li |
| 4,725,549 | A | | 2/1988 | Cooke et al. |
| 4,853,332 | A | * | 8/1989 | Mark |
| 4,959,314 | A | * | 9/1990 | Mark et al. ............... 424/85.5 |
| 5,217,867 | A | | 6/1993 | Evans et al. |

OTHER PUBLICATIONS

Heymsfield et al. J. Clin. Invest. 60: 563-570, 1977.*
Reagan et al. Proc. Nat. Acad. Sci. USA 72(5): 1684-1686, 1975.*
Tokunaga et al. Eur. J. Biochem. 153: 445-449, 1985.*
Khurana et al. Endocrinology 140(9)4127-4132, 1999.*
Corbacho et al., J. Endocrinology 173(219-238)2002.*
Goffin et al., Sequence-Function Relationships Within the Expanding Family of Prolactin, Growth Hormone, Placental Lactogen, and Related Proteins in Mammals*, Edocrine Reviews, vol. 17, No. 4.
Ampudia, X. et al. European Journal of Obstetrics, Gynecology, and Reproductive Biology (abstract) 46(101-107) 1992.
Andries et al. Biochem J•281 :393-400 (1993).
Aston, R. et al. EMBO J. 2:4:493-497 (1983).
Baldocchi et al. Endocrinology 133:935-938 (1993).
Casabiell, MC. et al. Endocrinology 125:4(1967) 1989.
Clapp C. et al. Prolactin Gene Family and Its Receptors 119-122 (1988).
Clapp et al. Endocrinol. 122:2892-2898 (1988).
Clapp, C. et al. Abstract No. 1387 73rd Ann Mtg. Endoc. Soc. 1991.
Clapp et al. Endocrinol 130:3:1380-1386 (1992).
Clapp et al. Endocrinol. 121:6:2055-2064 (1987).
Clapp et al. Endocrinology 125:2:1054-1059 (1989).
Clapp et al. Endocrinology 133:1292-1299 (1993) (Weiner).
Cooke et al. The Journal Of Biological Chemistry 256:4007-4016 (1980).
Cooke The Journal Of Biological Chemistry 255:13:6502-6510 (1980).
D'Angelo, G. et al. The Endocrine Society Program & Abstracts 76th Annual Meeting Jun. 15-18, 1994.
D'Angelo, G. et al. PNAS 92:14:6374-6378 (1995).
Ferrara et al. The Endocrine Society 70th Annual Meeting, Jun. 8-11, 1988.
Ferrara et al. Endocrinology 129:2:896-900 (1991).
Fukuoka, H. et al. Horm. Res. 35(suppl 1)58-63.
Kim, K.J. et al. Nature 362:841-844 (1993).
Luck, D.L. et al. Protein Engineering 5:559-567 (1992).
Martinez-Rodriguez, H.G. et al. Archives of Medical Research 28:4(507-512) 1997.
Mitra et al. Biochemical and Biophysical Research Communications 95:4:1760-1767 (1980).
Nicoll et al. Endocrine Reviews 7(2):169-203 (1986).
Russell et al. The Journal Of Biological Chemistry 254:2296-2301 (1979).
Russell et al. The Journal Of Biological Chemistry 256:1:296-300 (1981).
Schneider et al. The Journal Of Biological Chemistry 256:1:301-303 (1981).
Sinha et al. J. Clim Endoc. & Metab 60:2:239-243 (1985).
Unlisted Drugs 40(10):185, Oct. 1988.
Vick, R.S. et al. Biochem Biophys Acta 931:196-204 (1987).
Warner, M.D: et al. Horm. Metab. Res. 25(425-429) 1992.
Cunningham et al., Receptor and Antibody Epitopes in Human Growth Hormone Identified by Homolog-Scanning Mutagenesis, Science, vol. 243. pp. 1330-1336. 1989.

* cited by examiner

*Primary Examiner*—Christine J. Saoud
(74) *Attorney, Agent, or Firm*—Sutherland Asbill & Brennan LLP

(57) ABSTRACT

The current invention provides novel antiangiogenic peptides which correspond to about 133 consecutive amino acids of the N-terminal sequence of growth hormone.

7 Claims, 6 Drawing Sheets

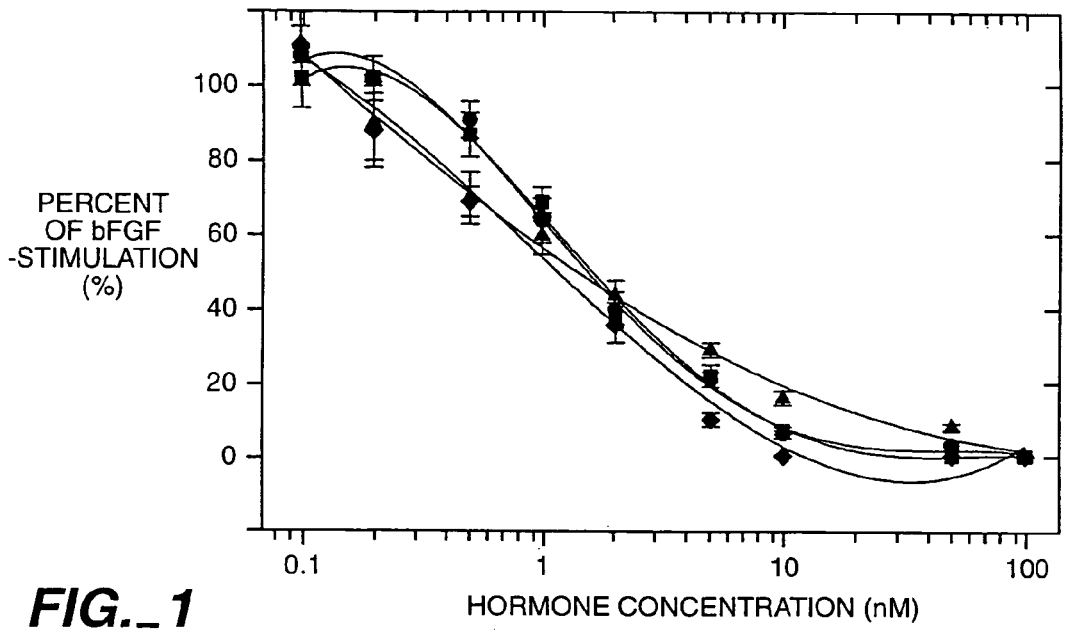
FIG._1
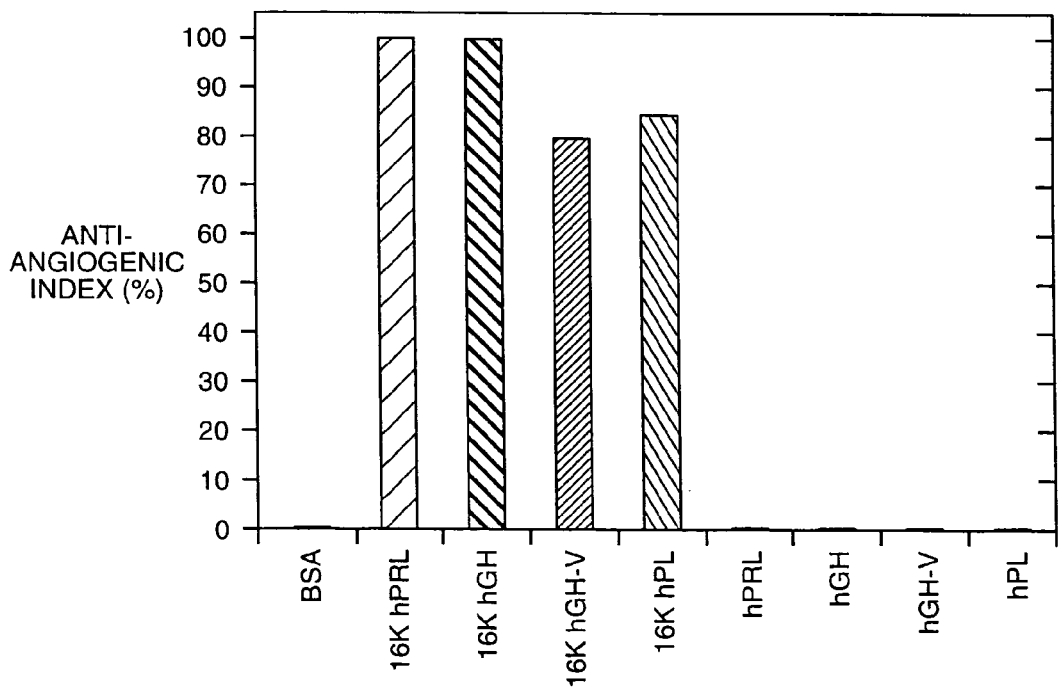
FIG._2

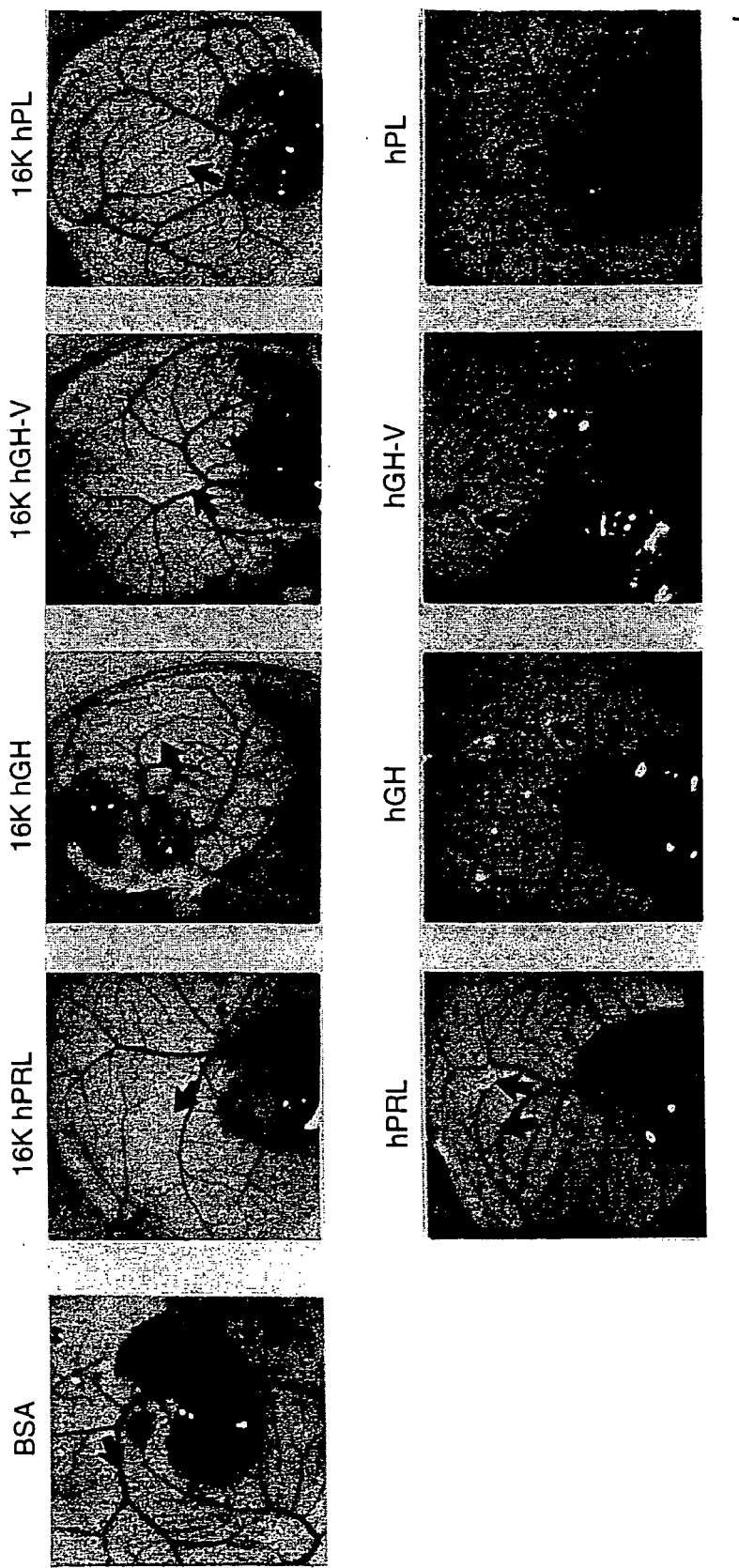
FIG._3

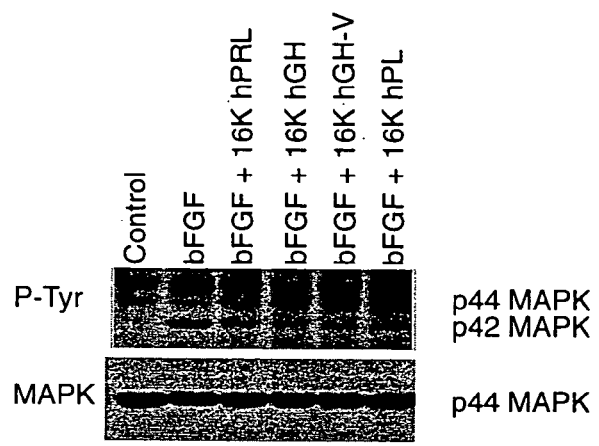
FIG._4A-1
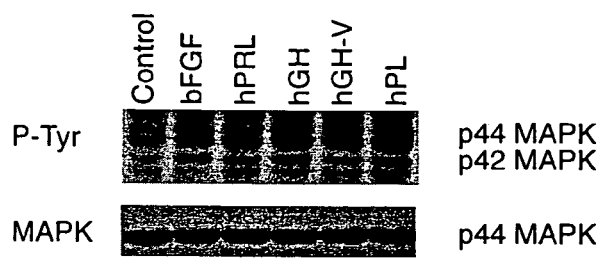
FIG._4A-2
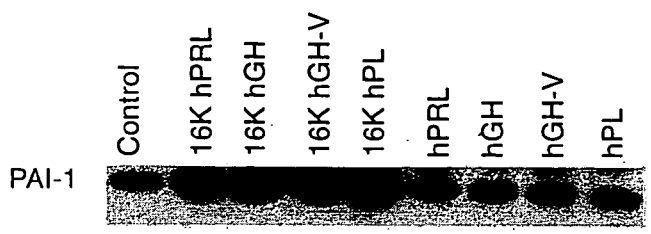
FIG._5A-1
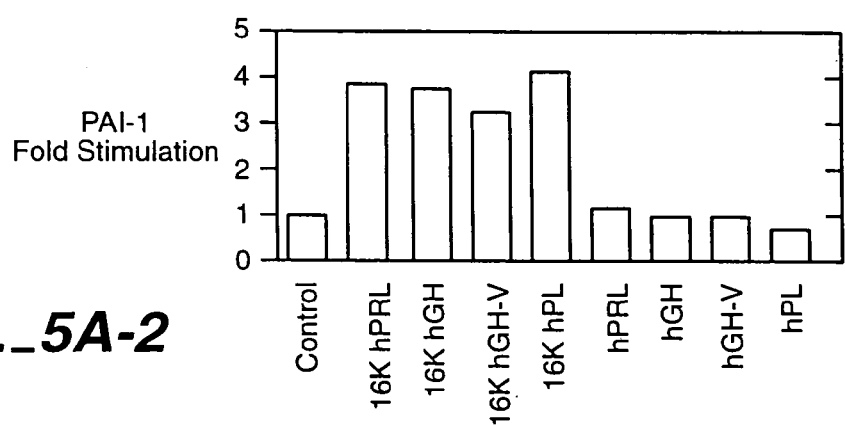
FIG._5A-2
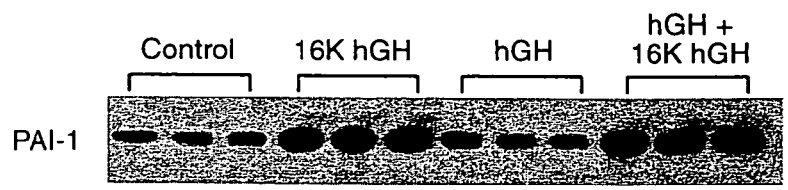
FIG._5B

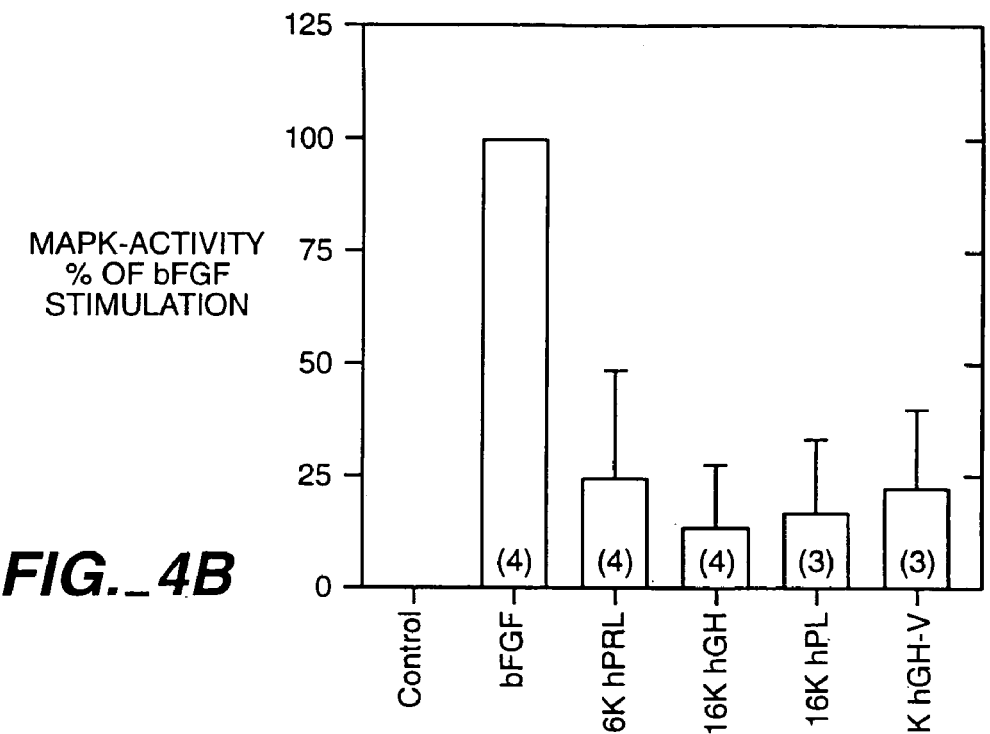
FIG._4B
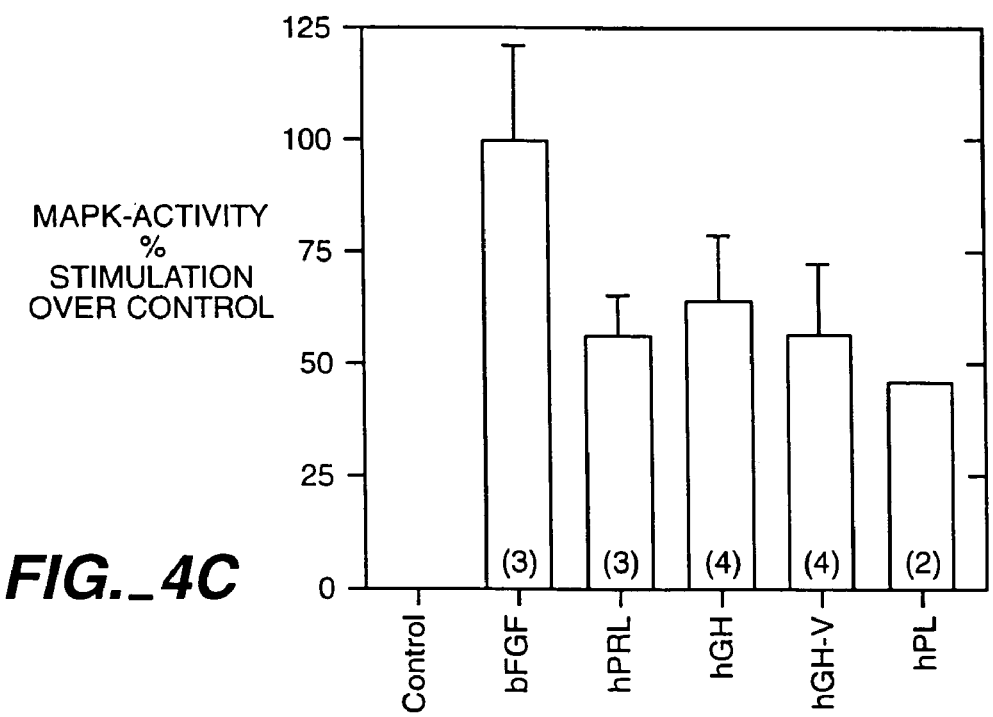
FIG._4C

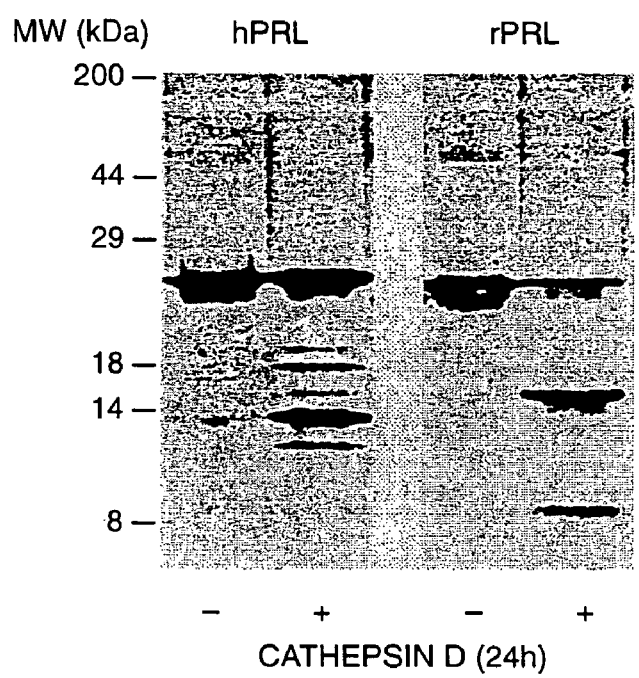
FIG._6
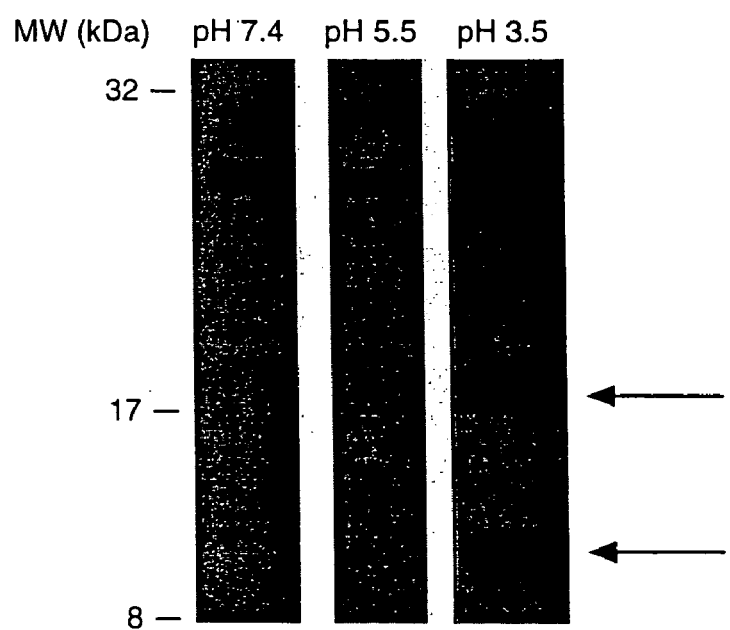
FIG._7

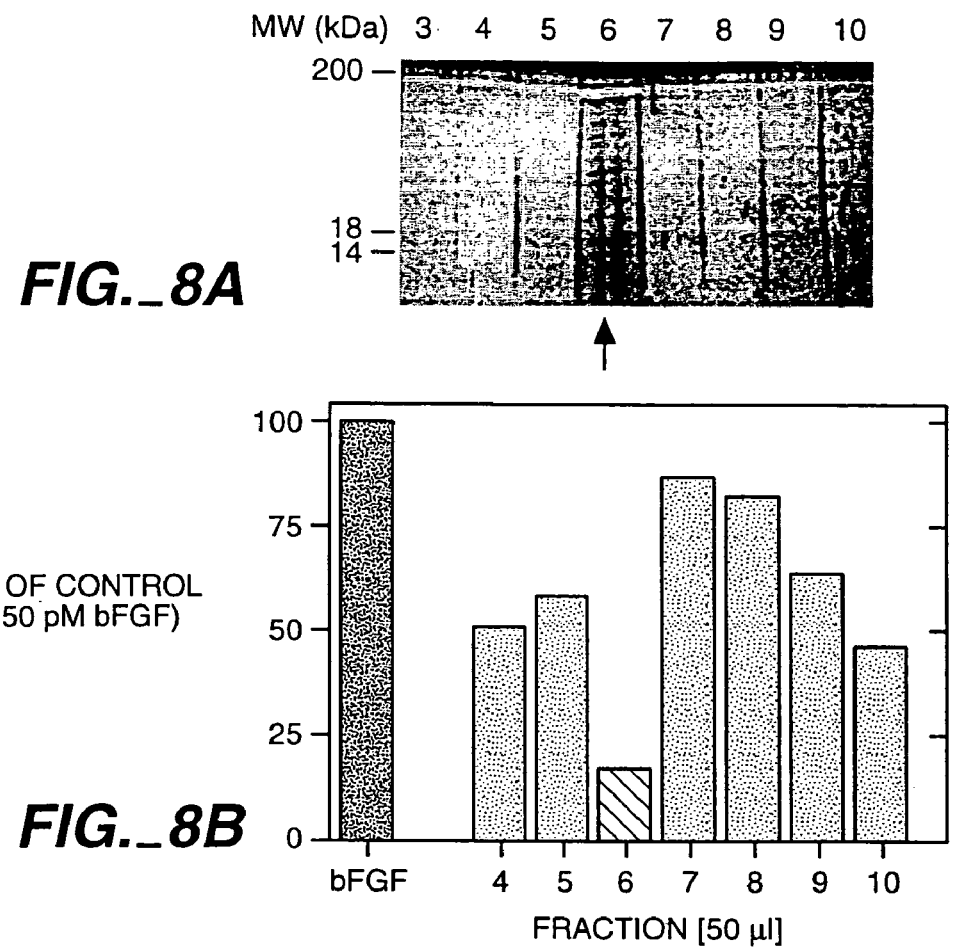
FIG._8A
FIG._8B
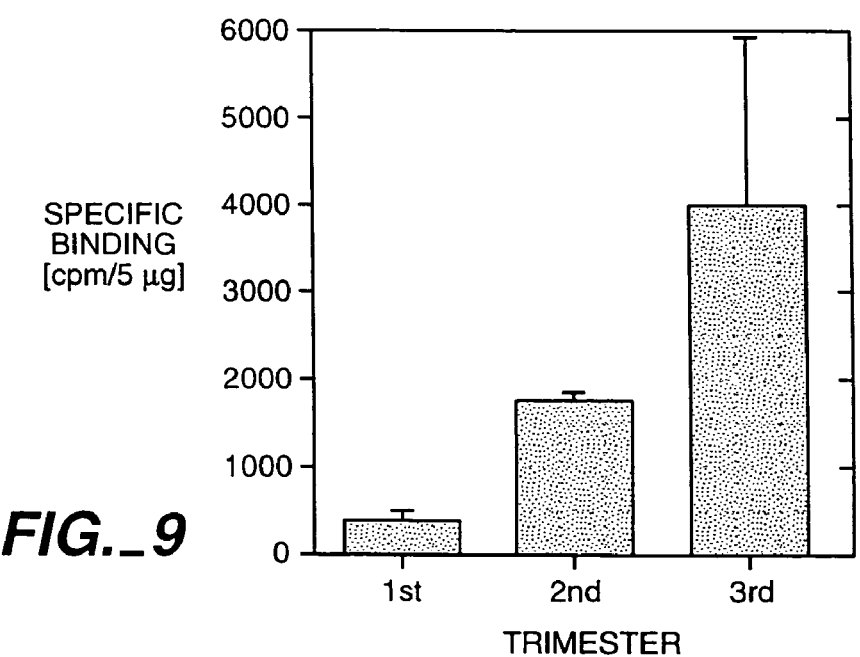
FIG._9

SEQUENCE LISTING

```
<160> NUMBER OF SEQ ID NOS: 34

<210> SEQ ID NO 1
<211> LENGTH: 603
<212> TYPE: DNA
<213> ORGANISM: Homo sapiens

<400> SEQUENCE: 1
atgttgccca tctgtcccgg cggggctgcc cgatgccagg tgaccttcg agacctgttt      60 gaccgcgccg tcgtcctgtc ccactacatc cataacctct cctcagaaat gttcagcgaa     120
ttcgataaac ggtataccca tggccggggg ttcattacca aggccatcaa cagctgccac     180
acttcttccc ttgccacccc cgaagacaag gagcaagccc aacagatgaa tcaaaaagac     240
tttctgagcc tgatagtcag catattgcga tcctggaatg agcctctgta tcatctggtc     300
acggaagtac gtggtatgca agaagcccg gaggctatcc tatccaaagc tgtagagatt      360
gaggagcaaa ccaaacggct tctagagggc atggagctga tagtcagcca ggttcatcct     420
gaaaccaaag aaaatgagat ctaccctgtc tggtcgggac ttccatccct gcagatggct     480
gatgaagaat ctcgcctttc tgcttattat aacctgctcc actgcctacg caggcattca     540
cataaaatcg acaattatct caagctcctg aagtgccgaa tcatccacaa caacaactgc     600
taa                                                                    603

<210> SEQ ID NO 2
<211> LENGTH: 375
<212> TYPE: DNA
<213> ORGANISM: Homo sapiens

<400> SEQUENCE: 2
atgttgccca tctgtcccgg cggggctgcc cgatgccagg tgaccttcg agacctgttt      60 gaccgcgccg tcgtcctgtc ccactacatc cataacctct cctcagaaat gttcagcgaa     120
ttcgataaac ggtataccca tggccggggg ttcattacca aggccatcaa cagctcccac     180
acttcttccc ttgccacccc cgaagacaag gagcaagccc aacagatgaa tcaaaaagac     240
tttctgagcc tgatagtcag catattgcga tcctggaatg agcctctgta tcatctggtc     300
acggaagtac gtggtatgca agaagcccg gaggctatcc tatccaaagc tgtagagatt      360
gaggagcaaa cctaa                                                       375
```

<210> SEQ ID NO 3
<211> LENGTH: 423
<212> TYPE: DNA
<213> ORGANISM: Homo sapiens

<400> SEQUENCE: 3

| | | | | | |
|---|---|---|---|---|---|
| atgttgccca | tctgtcccgg | cggggctgcc | cgatgccagg | tgaccttcg | agacctgttt | 60 |
| gaccgcgccg | tcgtcctgtc | ccactacatc | cataacctct | cctcagaaat | gttcagcgaa | 120 |
| ttcgataaac | ggtataccca | tggccggggg | ttcattacca | aggccatcaa | cagctcccac | 180 |
| acttcttccc | ttgccacccc | cgaagacaag | gagcaagccc | aacagatgaa | tcaaaaagac | 240 |
| tttctgagcc | tgatagtcag | catattgcga | tcctggaatg | agcctctgta | tcatctggtc | 300 |
| acggaagtac | gtggtatgca | agaagccccg | gaggctatcc | tatccaaagc | tgtagagatt | 360 |
| gaggagcaaa | ccaaacggct | tctagagggc | atggagctga | tagtcagcca | ggttcatcct | 420 |
| tga | | | | | | 423 |

<210> SEQ ID NO 4
<211> LENGTH: 603
<212> TYPE: DNA
<213> ORGANISM: Homo sapiens

<400> SEQUENCE: 4

| | | | | | |
|---|---|---|---|---|---|
| atgttgccca | tctgtcccgg | cggggctgcc | cgatgccagg | tgaccttcg | agacctgttt | 60 |
| gaccgcgccg | tcgtcctgtc | ccactacatc | cataacctct | cctcagaaat | gttcagcgaa | 120 |
| ttcgataaac | ggtataccca | tggccggggg | ttcattacca | aggccatcaa | cagctcccac | 180 |
| acttcttccc | ttgccacccc | cgaagacaag | gagcaagccc | aacagatgaa | tcaaaaagac | 240 |
| tttctgagcc | tgatagtcag | catattgcga | tcctggaatg | agcctctgta | tcatctggtc | 300 |
| acggaagtac | gtggtatgca | agaagccccg | gaggctatcc | tatccaaagc | tgtagagatt | 360 |
| gaggagcaaa | ccaaacggct | tctagagggc | atggagctga | tagtcagcca | ggttcatcct | 420 |
| agacccccaa | cacctgagat | ctaccctgtc | tggtcgggac | ttccatccct | gcagatggct | 480 |
| gatgaagagt | ctcgcctttc | tgcttattat | aacctgctcc | actgcctacg | cagggattca | 540 |
| cataaaatcg | acaattatct | caagctcctg | aagtgccgaa | tcatccacaa | caacaactgc | 600 |
| taa | | | | | | 603 |

<210> SEQ ID NO 5
<211> LENGTH: 603
<212> TYPE: DNA
<213> ORGANISM: Homo sapiens

<400> SEQUENCE: 5

| | | | | | |
|---|---|---|---|---|---|
| tacaacgggt | agacagggcc | gccccgacgg | gctacggtcc | actgggaagc | tctggacaaa | 60 |
| ctggcgcggc | agcaggacag | ggtgatgtag | gtattggaga | ggagtctta | caagtcgctt | 120 |
| aagctatttg | ccatatgggt | accggccccc | aagtaatggt | tccggtagtt | gtcgacggtg | 180 |
| tgaagaaggg | aacggtgggg | gcttctgttc | ctcgttcggg | ttgtctactt | agttttctg | 240 |
| aaagactcgg | actatcagtc | gtataacgct | aggaccttac | tcggagacat | agtagaccag | 300 |
| tgccttcatg | caccatacgt | tcttcggggc | ctccgatagg | ataggtttcg | acatctctaa | 360 |
| ctcctcgttt | ggtttgccga | agatctcccg | tacctcgact | atcagtcggt | ccaagtagga | 420 |
| ctttggtttc | ttttactcta | gatgggacag | accagccctg | aagtaggga | cgtctaccga | 480 |
| ctacttctca | gagcggaaag | acgaataata | ttggacgagg | tgacggatgc | gtccctaagt | 540 |

```
gtattttagc tgttaataga gttcgaggac ttcacggctt agtaggtgtt gttgttgacg    600
att                                                                  603
```

<210> SEQ ID NO 6
<211> LENGTH: 375
<212> TYPE: DNA
<213> ORGANISM: Homo sapiens

<400> SEQUENCE: 6

```
tacaacgggt agacagggcc gccccgacgg gctacggtcc actgggaagc tctggacaaa     60
ctggcgcggc agcaggacag ggtgatgtag gtattggaga ggagtcttta caagtcgctt    120
aagctatttg ccatatgggt accggccccc aagtaatggt tccggtagtt gtcgacggtg    180
tgaagaaggg aacggtgggg gcttctgttc ctcgttcggg ttgtctactt agttttctg     240 aaagactcgg actatcagtc gtataacgct aggaccttac tcggagacat agtagaccag    300
tgccttcatg caccatacgt tcttcggggc ctccgatagg ataggtttcg acatctctaa    360
ctcctcgttt ggatt                                                     375
```

<210> SEQ ID NO 7
<211> LENGTH: 423
<212> TYPE: DNA
<213> ORGANISM: Homo sapiens

<400> SEQUENCE: 7

```
tacaacgggt agacagggcc gccccgacgg gctacggtcc actgggaagc tctggacaaa     60
ctggcgcggc agcaggacag ggtgatgtag gtattggaga ggagtcttta caagtcgctt    120
aagctatttg ccatatgggt accggccccc aagtaatggt tccggtagtt gtcgacggtg    180
tgaagaaggg aacggtgggg gcttctgttc ctcgttcggg ttgtctactt agttttctg     240 aaagactcgg actatcagtc gtataacgct aggaccttac tcggagacat agtagaccag    300
tgccttcatg caccatacgt tcttcggggc ctccgatagg ataggtttcg acatctctaa    360
ctcctcgttt ggtttgccga agatctcccg tacctcgact atcagtcggt ccaagtagga    420
act                                                                  423
```

<210> SEQ ID NO 8
<211> LENGTH: 603
<212> TYPE: DNA
<213> ORGANISM: Homo sapiens

<400> SEQUENCE: 8

```
tacaacgggt agacagggcc gccccgacgg gctacggtcc actgggaagc tctggacaaa     60
ctggcgcggc agcaggacag ggtgatgtag gtattggaga ggagtcttta caagtcgctt    120
aagctatttg ccatatgggt accggccccc aagtaatggt tccggtagtt gtcgacggtg    180
tgaagaaggg aacggtgggg gcttctgttc ctcgttcggg ttgtctactt agttttctg     240 aaagactcgg actatcagtc gtataacgct aggaccttac tcggagacat agtagaccag    300
tgccttcatg caccatacgt tcttcggggc ctccgatagg ataggtttcg acatctctaa    360
ctcctcgttt ggtttgccga agatctcccg tacctcgact atcagtcggt ccaagtagga    420
tctgggggtt gtggactcta gatggacag accagccctg aagtaggga cgtctaccga      480 ctacttctca gagcggaaag acgaataata ttggacgagg tgacggatgc gtccctaagt    540
gtattttagc tgttaataga gttcgaggac ttcacggctt agtaggtgtt gttgttgacg    600
att                                                                  603
```

<210> SEQ ID NO 9
<211> LENGTH: 200
<212> TYPE: PRT
<213> ORGANISM: Homo sapiens

<400> SEQUENCE: 9

```
Met Leu Pro Ile Cys Pro Gly Gly Ala Ala Arg Cys Gln Val Thr Leu
  1               5                  10                  15

Arg Asp Leu Phe Asp Arg Ala Val Val Leu Ser His Tyr Ile His Asn
             20                  25                  30

Leu Ser Ser Glu Met Phe Ser Glu Phe Asp Lys Arg Tyr Thr His Gly
         35                  40                  45

Arg Gly Phe Ile Thr Lys Ala Ile Asn Ser Cys His Thr Ser Ser Leu
     50                  55                  60

Ala Thr Pro Glu Asp Lys Glu Gln Ala Gln Gln Met Asn Gln Lys Asp
 65                  70                  75                  80

Phe Leu Ser Leu Ile Val Ser Ile Leu Arg Ser Trp Asn Glu Pro Leu
                 85                  90                  95

Tyr His Leu Val Thr Glu Val Arg Gly Met Gln Glu Ala Pro Glu Ala
            100                 105                 110

Ile Leu Ser Lys Ala Val Glu Ile Glu Glu Gln Thr Lys Arg Leu Leu
        115                 120                 125

Glu Gly Met Glu Leu Ile Val Ser Gln Val His Pro Glu Thr Lys Glu
130                 135                 140

Asn Glu Ile Tyr Pro Val Trp Ser Gly Leu Pro Ser Leu Gln Met Ala
145                 150                 155                 160

Asp Glu Glu Ser Arg Leu Ser Ala Tyr Tyr Asn Leu Leu His Cys Leu
                165                 170                 175

Arg Arg Asp Ser His Lys Ile Asp Asn Tyr Leu Lys Leu Leu Lys Cys
            180                 185                 190

Arg Ile Ile His Asn Asn Asn Cys
        195                 200
```

<210> SEQ ID NO 10
<211> LENGTH: 124
<212> TYPE: PRT
<213> ORGANISM: Homo sapiens

<400> SEQUENCE: 10

```
Met Leu Pro Ile Cys Pro Gly Gly Ala Ala Arg Cys Gln Val Thr Leu
  1               5                  10                  15

Arg Asp Leu Phe Asp Arg Ala Val Val Leu Ser His Tyr Ile His Asn
             20                  25                  30

Leu Ser Ser Glu Met Phe Ser Glu Phe Asp Lys Arg Tyr Thr His Gly
         35                  40                  45

Arg Gly Phe Ile Thr Lys Ala Ile Asn Ser Ser His Thr Ser Ser Leu
     50                  55                  60

Ala Thr Pro Glu Asp Lys Glu Gln Ala Gln Gln Met Asn Gln Lys Asp
 65                  70                  75                  80

Phe Leu Ser Leu Ile Val Ser Ile Leu Arg Ser Trp Asn Glu Pro Leu
                 85                  90                  95

Tyr His Leu Val Thr Glu Val Arg Gly Met Gln Glu Ala Pro Glu Ala
            100                 105                 110

Ile Leu Ser Lys Ala Val Glu Ile Glu Glu Gln Thr
        115                 120
```

<210> SEQ ID NO 11
<211> LENGTH: 140
<212> TYPE: PRT
<213> ORGANISM: Homo sapiens

<400> SEQUENCE: 11

Met Leu Pro Ile Cys Pro Gly Gly Ala Ala Arg Cys Gln Val Thr Leu
1               5                   10                  15

Arg Asp Leu Phe Asp Arg Ala Val Val Leu Ser His Tyr Ile His Asn
            20                  25                  30

Leu Ser Glu Met Phe Ser Glu Phe Asp Lys Arg Tyr Thr His Gly
        35                  40                  45

Arg Gly Phe Ile Thr Lys Ala Ile Asn Ser Ser His Thr Ser Ser Leu
    50                  55                  60

Ala Thr Pro Glu Asp Lys Glu Gln Ala Gln Gln Met Asn Gln Lys Asp
65                  70                  75                  80

Phe Leu Ser Leu Ile Val Ser Ile Leu Arg Ser Trp Asn Glu Pro Leu
                85                  90                  95

Tyr His Leu Val Thr Glu Val Arg Gly Met Gln Glu Ala Pro Glu Ala
            100                 105                 110

Ile Leu Ser Lys Ala Val Glu Ile Glu Glu Gln Thr Lys Arg Leu Leu
        115                 120                 125

Glu Gly Met Glu Leu Ile Val Ser Gln Val His Pro
    130                 135                 140

<210> SEQ ID NO 12
<211> LENGTH: 143
<212> TYPE: PRT
<213> ORGANISM: Homo sapiens

<400> SEQUENCE: 12

Met Leu Pro Ile Cys Pro Gly Gly Ala Ala Arg Cys Gln Val Thr Leu
1               5                   10                  15

Arg Asp Leu Phe Asp Arg Ala Val Val Leu Ser His Tyr Ile His Asn
            20                  25                  30

Leu Ser Glu Met Phe Ser Glu Phe Asp Lys Arg Tyr Thr His Gly
        35                  40                  45

Arg Gly Phe Ile Thr Lys Ala Ile Asn Ser Ser His Thr Ser Ser Leu
    50                  55                  60

Ala Thr Pro Glu Asp Lys Glu Gln Ala Gln Gln Met Asn Gln Lys Asp
65                  70                  75                  80

Phe Leu Ser Leu Ile Val Ser Ile Leu Arg Ser Trp Asn Glu Pro Leu
                85                  90                  95

Tyr His Leu Val Thr Glu Val Arg Gly Met Gln Glu Ala Pro Glu Ala
            100                 105                 110

Ile Leu Ser Lys Ala Val Glu Ile Glu Glu Gln Thr Lys Arg Leu Leu
        115                 120                 125

Glu Gly Met Glu Leu Ile Val Ser Gln Val His Pro Arg Pro Pro
    130                 135                 140

<210> SEQ ID NO 13
<211> LENGTH: 579
<212> TYPE: DNA
<213> ORGANISM: Homo sapiens

<400> SEQUENCE: 13

```
atggtccaaa ccgttccgtt atccaggctt tttgaccacg ctatgctcca agcccatcgc    60
gcgcaccagc tggccattga cacctaccag gagtttgaag aaacctatat cccaaaggac   120
cagaagtatt cgttcctgca tgactcccag acctccttct ctttctcaga ctctattccg   180
acaccctcca acatggagga aacgcaacag aaatccaatc tagagctgct ccgcatctcc   240
ctgctgctca tcgagtcgtg gctggagccc gtgcggttcc tcaggagtat gttcgccaac   300
aacctggtgt atgacacctc ggacagcgat gactatcacc tcctaaagga cctagaggaa   360
ggcatccaaa cgctgatggg gaggctggaa gacggcagcc gccggactgg gcagatcctc   420
aagcagacct acagcaagtt tgacacaaac tcgcacaacc atgacgcact gctcaagaac   480
tacgggctgc tctactgctt caggaaggac atggacaagg tcgagacatt cctgcgcatg   540
gtgcagtgcc gctctgtgga gggcagctgt ggcttctag                         579
```

<210> SEQ ID NO 14
<211> LENGTH: 579
<212> TYPE: DNA
<213> ORGANISM: Homo sapiens

<400> SEQUENCE: 14

```
atggtccaaa ccgttccgtt atccaggctt tttgaccacg ctatgctcca agcccatcgc    60
gcgcaccagc tggccattga cacctaccag gagtttgaag aaacctatat cccaaaggac   120
cagaagtatt cgttcctgca tgactcccag acctccttct gcttctcaga ctctattccg   180
acaccctcca acatggagga aacgcaacag aaatccaatc tagagctgct ccgcatctcc   240
ctgctgctca tcgagtcgtg gctggagccc gtgcggttcc tcaggagtat gttcgccaac   300
aacctggtgt atgacacctc ggacagcgat gactatcacc tcctaaagga cctagaggaa   360
ggcatccaaa cgctgatggg gaggctggaa gacggcagcc ccggactgg gcagatcctc    420 aagcagacct acagcaagtt tgacacaaac tcgcacaacc atgacgcact gctcaagaac   480
tacgggctgc tctactgctt caggaaggac atggacaagg tcgagacatt cctgcgcatg   540
gtgcagtgcc gctctgtgga gggcagctgt ggcttctag                         579
```

<210> SEQ ID NO 15
<211> LENGTH: 579
<212> TYPE: DNA
<213> ORGANISM: Homo sapiens

<400> SEQUENCE: 15

```
taccaggttt ggcaaggcaa taggtccgaa aaactggtgc gatacgaggt tcgggtagcg    60
cgcgtggtcg accggtaact gtggatggtc ctcaaacttc tttggatata gggtttcctg   120
gtcttcataa gcaaggacgt actgagggtc tggaggaaga cgaagagtct gagataaggc   180
tgtgggaggt tgtacctcct ttgcgttgtc tttaggttag atctcgacga ggcgtagagg   240
gacgacgagt agctcagcac cgacctcggg cacgccaagt agtcctcata caagcggtgg   300
ttggaccaca tactgtggag cctgtcgcta ctgatagtgg aggatttcct ggatctcctt   360
ccgtaggttt gcgactaccc ctccgacctt ctgccgtcgg cggcctgacc cgtctaggag   420
ttcgtctgga tgtcgttcaa actgtgtttg agcgtgttgg tactgcgtga cgagttcttg   480
atgcccgacg agatgacgaa gtccttcctg tacctgttcc agctctgtaa ggacgcgtac   540
cacgtcacgg cgagacacct cccgtcgaca ccgaagatc                         579
```

<210> SEQ ID NO 16
<211> LENGTH: 579

```
<212> TYPE: DNA
<213> ORGANISM: Homo sapiens

<400> SEQUENCE: 16
taccaggttt ggcaaggcaa taggtccgaa aaactggtgc gatacgaggt tcgggtagcg      60
cgcgtggtcg accggtaact gtggatggtc ctcaaacttc tttggatata gggtttcctg     120
gtcttcataa gcaaggacgt actgagggtc tggaggaaga gaaagagtct gagataaggc     180
tgtgggaggt tgtacctcct ttgcgttgtc tttaggttag atctcgacga ggcgtagagg     240
gacgacgagt agctcagcac cgacctcggg cacgccaagg agtcctcata caagcggttg     300
ttggaccaca tactgtggag cctgtcgcta ctgatagtgg aggatttcct ggatctcctt     360
ccgtaggttt gcgactaccc ctccgacctt ctgccgtcgg gggcctgacc cgtctaggag     420
ttcgtctgga tgtcgttcaa actgtgtttg agcgtgttgg tactgcgtga cgagttcttg     480
atgcccgacg agatgacgaa gtccttcctg tacctgttcc agctctgtaa ggacgcgtac     540
cacgtcacgg cgagacacct cccgtcgaca ccgaagatc                            579

<210> SEQ ID NO 17
<211> LENGTH: 192
<212> TYPE: PRT
<213> ORGANISM: Homo sapiens

<400> SEQUENCE: 17

Met Val Gln Thr Val Pro Leu Ser Arg Leu Phe Asp His Ala Met Leu
 1               5                  10                  15

Gln Ala His Arg Ala His Gln Leu Ala Ile Asp Thr Tyr Gln Glu Phe
                20                  25                  30

Glu Glu Thr Tyr Ile Pro Lys Asp Gln Lys Tyr Ser Phe Leu His Asp
            35                  40                  45

Ser Gln Thr Ser Phe Cys Phe Ser Asp Ser Ile Pro Thr Pro Ser Asn
        50                  55                  60

Met Glu Glu Thr Gln Gln Lys Ser Asn Leu Glu Leu Leu Arg Ile Ser
 65                  70                  75                  80

Leu Leu Leu Ile Glu Ser Trp Leu Glu Pro Val Arg Phe Leu Arg Ser
                85                  90                  95

Met Phe Ala Asn Asn Leu Val Tyr Asp Thr Ser Asp Ser Asp Asp Tyr
               100                 105                 110

His Leu Leu Lys Asp Leu Glu Glu Gly Ile Gln Thr Leu Met Gly Arg
            115                 120                 125

Leu Glu Asp Gly Ser Arg Arg Thr Gly Gln Ile Leu Lys Gln Thr Tyr
        130                 135                 140

Ser Lys Phe Asp Thr Asn Ser His Asn His Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Met Val Gln Cys Arg Ser Val Glu Gly Ser Cys Gly Phe
            180                 185                 190

<210> SEQ ID NO 18
<211> LENGTH: 135
<212> TYPE: PRT
<213> ORGANISM: Homo sapiens

<400> SEQUENCE: 18

Met Val Gln Thr Val Pro Leu Ser Arg Leu Phe Asp His Ala Met Leu
 1               5                  10                  15
```

-continued

Gln Ala His Arg Ala His Gln Leu Ala Ile Asp Thr Tyr Gln Glu Phe
              20                  25                  30

Glu Glu Thr Tyr Ile Pro Lys Asp Gln Lys Tyr Ser Phe Leu His Asp
         35                  40                  45

Ser Gln Thr Ser Phe Ser Phe Ser Asp Ser Ile Pro Thr Pro Ser Asn
    50                  55                  60

Met Glu Glu Thr Gln Gln Lys Ser Asn Leu Glu Leu Leu Arg Ile Ser
65                  70                  75                  80

Leu Leu Leu Ile Glu Ser Trp Leu Glu Pro Val Arg Phe Leu Arg Ser
                85                  90                  95

Met Phe Ala Asn Asn Leu Val Tyr Asp Thr Ser Asp Ser Asp Asp Tyr
            100                 105                 110

His Leu Leu Lys Asp Leu Glu Glu Gly Ile Gln Thr Leu Met Gly Arg
        115                 120                 125

Leu Glu Asp Gly Ser Pro Arg
    130                 135

<210> SEQ ID NO 19
<211> LENGTH: 579
<212> TYPE: DNA
<213> ORGANISM: Homo sapiens

<400> SEQUENCE: 19
atgttcccaa ccattccctt atccaggctt tttgacaacg ctatgctccg cgcccatcgt      60
ctgcaccagc tggcctttga cacctaccag gagtttgaag aagcctatat cccaaaggaa     120
cagaagtatt cattcctgca gaaccccag acctccctct gtttctcaga gtctattccg      180
acaccctcca acaggagga aacacaacag aaatccaacc tagagctgct ccgcatctcc      240
ctgctgctca tccagtcgtg gctggagccc gtgcagttcc tcaggagtgt cttcgccaac     300
agcctggtgt acggcgcctc tgacagcaac gtctatgacc tcctaaagga cctagaggaa     360
ggcatccaaa cgctgatggg gaggctggaa gatggcagcc cccggactgg gcagatcttc     420
aagcagacct acagcaagtt cgacacaaac tcacacaacg atgacgcact actcaagaac     480
tacgggctgc tctactgctt caggaaggac atggacaagg tcgagacatt cctgcgcatc     540
gtgcagtgcc gctctgtgga gggcagctgt ggcttctag                            579

<210> SEQ ID NO 20
<211> LENGTH: 405
<212> TYPE: DNA
<213> ORGANISM: Homo sapiens

<400> SEQUENCE: 20
atgttcccaa ccattccctt atccaggctt tttgacaacg ctatgctccg cgcccatcgt      60
ctgcaccagc tggcctttga cacctaccag gagtttgaag aagcctatat cccaaaggaa     120
cagaagtatt cattcctgca gaaccccag acctccctct ctttctcaga gtctattccg      180
acaccctcca acaggagga aacacaacag aaatccaacc tagagctgct ccgcatctcc      240
ctgctgctca tccagtcgtg gctggagccc gtgcagttcc tcaggagtgt cttcgccaac     300
agcctggtgt acggcgcctc tgacagcaac gtctatgacc tcctaaagga cctagaggaa     360
ggcatccaaa cgctgatggg gaggctggaa gatggcagcc cctag                     405

<210> SEQ ID NO 21
<211> LENGTH: 579
<212> TYPE: DNA

<213> ORGANISM: Homo sapiens

<400> SEQUENCE: 21

```
tacaagggtt ggtaagggaa taggtccgaa aaactgttgc gatacgaggc gcgggtagca      60
gacgtggtcg accggaaact gtggatggtc ctcaaacttc ttcggatata gggtttcctt     120
gtcttcataa gtaaggacgt cttggggggtc tggagggaga caaagagtct cagataaggc    180
tgtgggaggt tgtccctcct ttgtgttgtc tttaggttgg atctcgacga ggcgtagagg     240
gacgacgagt aggtcagcac cgacctcggg cacgtcaagg agtcctcaca gaagcggttg     300
tcggaccaca tgccgcggag actgtcgttg cagatactgg aggatttcct ggatctcctt     360
ccgtaggttt gcgactaccc ctccgacctt ctaccgtcgg gggcctgacc cgtctagaag     420
ttcgtctgga tgtcgttcaa gctgtgtttg agtgtgttgc tactgcgtga tgagttcttg     480
atgcccgacg agatgacgaa gtccttcctg tacctgttcc agctctgtaa ggacgcgtag     540
cacgtcacgg cgagacacct cccgtcgaca ccgaagatc                           579
```

<210> SEQ ID NO 22
<211> LENGTH: 405
<212> TYPE: DNA
<213> ORGANISM: Homo sapiens

<400> SEQUENCE: 22

```
tacaagggtt ggtaagggaa taggtccgaa aaactgttgc gatacgaggc gcgggtagca      60
gacgtggtcg accggaaact gtggatggtc ctcaaacttc ttcggatata gggtttcctt     120
gtcttcataa gtaaggacgt cttggggggtc tggagggaga caaagagtct cagataaggc    180
tgtgggaggt tgtccctcct ttgtgttgtc tttaggttgg atctcgacga ggcgtagagg     240
gacgacgagt aggtcagcac cgacctcggg cacgtcaagg agtcctcaca gaagcggttg     300
tcggaccaca tgccgcggag actgtcgttg cagatactgg aggatttcct ggatctcctt     360
ccgtaggttt gcgactaccc ctccgacctt ctaccgtcgg ggatc                     405
```

<210> SEQ ID NO 23
<211> LENGTH: 192
<212> TYPE: PRT
<213> ORGANISM: Homo sapiens

<400> SEQUENCE: 23

```
Met Phe Pro Thr Ile Pro Leu Ser Arg Leu Phe Asp Asn Ala Met Leu
  1               5                  10                  15
Arg Ala His Arg Leu His Gln Leu Ala Phe Asp Thr Tyr Gln Glu Phe
                 20                  25                  30
Glu Glu Ala Tyr Ile Pro Lys Glu Gln Lys Tyr Ser Phe Leu Gln Asn
             35                  40                  45
Pro Gln Thr Ser Leu Cys Phe Ser Glu Ser Ile Pro Thr Pro Ser Asn
         50                  55                  60
Arg Glu Glu Thr Gln Gln Lys Ser Asn Leu Glu Leu Leu Arg Ile Ser
     65                  70                  75                  80
Leu Leu Leu Ile Gln Ser Trp Leu Glu Pro Val Gln Phe Leu Arg Ser
                 85                  90                  95
Val Phe Ala Asn Ser Leu Val Tyr Gly Ala Ser Asp Ser Asn Val Tyr
                100                 105                 110
Asp Leu Leu Lys Asp Leu Glu Glu Gly Ile Gln Thr Leu Met Gly Arg
            115                 120                 125
Leu Glu Asp Gly Ser Pro Arg Thr Gly Gln Ile Phe Lys Gln Thr Tyr
```

```
            130                 135                 140
Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190

<210> SEQ ID NO 24
<211> LENGTH: 134
<212> TYPE: PRT
<213> ORGANISM: Homo sapiens

<400> SEQUENCE: 24

Met Phe Pro Thr Ile Pro Leu Ser Arg Leu Phe Asp Asn Ala Met Leu
  1               5                  10                  15

Arg Ala His Arg Leu His Gln Leu Ala Phe Asp Thr Tyr Gln Glu Phe
                20                  25                  30

Glu Glu Ala Tyr Ile Pro Lys Glu Gln Lys Tyr Ser Phe Leu Gln Asn
            35                  40                  45

Pro Gln Thr Ser Leu Ser Phe Ser Glu Ser Ile Pro Thr Pro Ser Asn
 50                  55                  60

Arg Glu Glu Thr Gln Gln Lys Ser Asn Leu Glu Leu Leu Arg Ile Ser
 65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro
        130

<210> SEQ ID NO 25
<211> LENGTH: 579
<212> TYPE: DNA
<213> ORGANISM: Homo sapiens

<400> SEQUENCE: 25
atgttcccaa ccattccctt atccaggctt tttgacaacg ctatgctccg cgcccgtcgc     60
ctgtaccagc tggcatatga cacctatcag gagtttgaag aagcctatat cctgaaggag    120
cagaagtatt cattcctgca gaaccccag acctccctct gcttctcaga gtctattcca     180
acaccttcca acagggtgaa aacgcagcag aaatctaacc tagagctgct ccgcatctcc    240
ctgctgctca tccagtcatg gctggagccc gtgcagctcc tcaggagcgt cttcgccaac    300
agcctggtgt atggcgcctc ggacagcaac gtctatcgcc acctgaagga cctagaggaa    360
ggcatccaaa cgctgatgtg gaggctggaa gatggcagcc cccggactgg gcagatcttc    420
aatcagtcct acagcaagtt tgacacaaaa tcgcacaacg atgacgcact gctcaagaac    480
tacgggctgc tctactgctt caggaaggac atggacaagg tcgagacatt cctgcgcatc    540
gtgcagtgcc gctctgtgga gggcagctgt ggcttctag                           579

<210> SEQ ID NO 26
<211> LENGTH: 579
<212> TYPE: DNA
<213> ORGANISM: Homo sapiens
```

<400> SEQUENCE: 26

```
atgttcccaa ccattcccctt atccaggctt tttgacaacg ctatgctccg cgcccgtcgc      60
ctgtaccagc tggcatatga cacctatcag gagtttgaag aagcctatat cctgaaggag     120
cagaagtatt cattcctgca gaaccccccag acctccctct gcttctcaga gtctattcca    180
acaccttcca acagggtgaa aacgcagcag aaatctaacc tagagctgct ccgcatctcc     240
ctgctgctca tccagtcatg gctggagccc gtgcagctcc tcaggagcgt cttcgccaac     300
agcctggtgt atggcgcctc ggacagcaac gtctatcgcc acctgaagga cctagaggaa     360
ggcatccaaa cgctgatgtg gaggctggaa gatggcagcc cccggactgg gcagatcttc     420
aatcagtcct acagcaagtt tgacacaaaa tcgcacaacg atgacgcact gctcaagaac     480
tacgggctgc tctactgctt caggaaggac atggacaagg tcgagacatt cctgcgcatc     540
gtgcagtgcc gctctgtgga gggcagctgt ggcttctag                            579
```

<210> SEQ ID NO 27
<211> LENGTH: 579
<212> TYPE: DNA
<213> ORGANISM: Homo sapiens

<400> SEQUENCE: 27

```
tacaagggtt ggtaagggaa taggtccgaa aaactgttgc gatacgaggc gcgggcagcg      60
gacatggtcg accgtatact gtggatagtc ctcaaacttc ttcggatata ggacttcctc     120
gtcttcataa gtaaggacgt cttggggggtc tggagggaga cgaagagtct cagataaggt    180
tgtggaaggt tgtcccactt ttgcgtcgtc tttagattgg atctcgacga ggcgtagagg     240
gacgacgagt aggtcagtac cgacctcggg cacgtcgagg agtcctcgca gaagcggttg     300
tcggaccaca taccgcggag cctgtcgttg cagatagcgg tggacttcct ggatctcctt    360
ccgtaggttt gcgactacac ctccgacctt ctaccgtcgg gggcctgacc cgtctagaag     420
ttagtcagga tgtcgttcaa actgtgtttt agcgtgttgc tactgcgtga cgagttcttg    480
atgcccgacg agatgacgaa gtccttcctg tacctgttcc agctctgtaa ggacgcgtag    540
cacgtcacgg cgagacacct cccgtcgaca ccgaagatc                            579
```

<210> SEQ ID NO 28
<211> LENGTH: 579
<212> TYPE: DNA
<213> ORGANISM: Homo sapiens

<400> SEQUENCE: 28

```
tacaagggtt ggtaagggaa taggtccgaa aaactgttgc gatacgaggc gcgggcagcg      60
gacatggtcg accgtatact gtggatagtc ctcaaacttc ttcggatata ggacttcctc     120
gtcttcataa gtaaggacgt cttggggggtc tggagggaga cgaagagtct cagataaggt    180
tgtggaaggt tgtcccactt ttgcgtcgtc tttagattgg atctcgacga ggcgtagagg     240
gacgacgagt aggtcagtac cgacctcggg cacgtcgagg agtcctcgca gaagcggttg     300
tcggaccaca taccgcggag cctgtcgttg cagatagcgg tggacttcct ggatctcctt    360
ccgtaggttt gcgactacac ctccgacctt ctaccgtcgg gggcctgacc cgtctagaag     420
ttagtcagga tgtcgttcaa actgtgtttt agcgtgttgc tactgcgtga cgagttcttg    480
atgcccgacg agatgacgaa gtccttcctg tacctgttcc agctctgtaa ggacgcgtag    540
cacgtcacgg cgagacacct cccgtcgaca ccgaagatc                            579
```

```
<210> SEQ ID NO 29
<211> LENGTH: 192
<212> TYPE: PRT
<213> ORGANISM: Homo sapiens

<400> SEQUENCE: 29

Met Phe Pro Thr Ile Pro Leu Ser Arg Leu Phe Asp Asn Ala Met Leu
 1               5                  10                  15

Arg Ala Arg Arg Leu Tyr Gln Leu Ala Tyr Asp Thr Tyr Gln Glu Phe
             20                  25                  30

Glu Glu Ala Tyr Ile Leu Lys Glu Gln Lys Tyr Ser Phe Leu Gln Asn
         35                  40                  45

Pro Gln Thr Ser Leu Cys Phe Ser Glu Ser Ile Pro Thr Pro Ser Asn
     50                  55                  60

Arg Val Lys Thr Gln Gln Lys Ser Asn Leu Glu Leu Leu Arg Ile Ser
 65                  70                  75                  80

Leu Leu Leu Ile Gln Ser Trp Leu Glu Pro Val Gln Leu Leu Arg Ser
                 85                  90                  95

Val Phe Ala Asn Ser Leu Val Tyr Gly Ala Ser Asp Ser Asn Val Tyr
            100                 105                 110

Arg His Leu Lys Asp Leu Glu Glu Gly Ile Gln Thr Leu Met Trp Arg
        115                 120                 125

Leu Glu Asp Gly Ser Pro Arg Thr Gly Gln Ile Phe Asn Gln Ser Tyr
    130                 135                 140

Ser Lys Phe Asp Thr Lys Ser His Asn Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190

<210> SEQ ID NO 30
<211> LENGTH: 135
<212> TYPE: PRT
<213> ORGANISM: Homo sapiens

<400> SEQUENCE: 30

Met Phe Pro Thr Ile Pro Leu Ser Arg Leu Phe Asp Asn Ala Met Leu
 1               5                  10                  15

Arg Ala Arg Arg Leu Tyr Gln Leu Ala Tyr Asp Thr Tyr Gln Glu Phe
             20                  25                  30

Glu Glu Ala Tyr Ile Leu Lys Glu Gln Lys Tyr Ser Phe Leu Gln Asn
         35                  40                  45

Pro Gln Thr Ser Leu Cys Phe Ser Glu Ser Ile Pro Thr Pro Ser Asn
     50                  55                  60

Arg Val Lys Thr Gln Gln Lys Ser Asn Leu Glu Leu Leu Arg Ile Ser
 65                  70                  75                  80

Leu Leu Leu Ile Gln Ser Trp Leu Glu Pro Val Gln Leu Leu Arg Ser
                 85                  90                  95

Val Phe Ala Asn Ser Leu Val Tyr Gly Ala Ser Asp Ser Asn Val Tyr
            100                 105                 110

Arg His Leu Lys Asp Leu Glu Glu Gly Ile Gln Thr Leu Met Trp Arg
        115                 120                 125

Leu Glu Asp Gly Ser Pro Arg
    130                 135
```

```
<210> SEQ ID NO 31
<211> LENGTH: 18
<212> TYPE: DNA
<213> ORGANISM: Homo sapiens

<400> SEQUENCE: 31
cctgaaacca aagaaaat                                                   18

<210> SEQ ID NO 32
<211> LENGTH: 6
<212> TYPE: PRT
<213> ORGANISM: Homo sapiens

<400> SEQUENCE: 32

Pro Glu Thr Lys Glu Asn
 1               5

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: nucleotide
      sequence coding for specific cleavage site of the
      IgA protease

<400> SEQUENCE: 33
cctagacccc caacacct                                                   18

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence:specific
      cleavage site of the IgA protease

<400> SEQUENCE: 34

Pro Arg Pro Pro Thr Pro
 1               5
```

ANTIANGIOGENIC PEPTIDE AGENTS

This application is a continuation application of U.S. application Ser. No. 09/819,094, filed Mar. 27, 2001, now abandoned, which is a continuation of U.S. application Ser. No. 09/076,675, filed May 12, 1998, now abandoned, which claims priority under 35 U.S.C. § 119(e) to U.S. Provisional Application No. 60/046,394, filed May 13, 1997 now abandoned, all of which are incorporated herein in their entirety.

BACKGROUND OF THE INVENTION

A growing number of serious, debilitating and often fatal diseases are associated with angiogenesis. These diseases are cumulatively called angiogenic diseases. Under normal physiological conditions, angiogenesis in mammals is endogenously controlled throughout the lifetime and neovascularization rarely occurs except during embryonic development, the reproductive cycle, and wound healing.

Examples of the pathological conditions leading to development of angiogenic diseases are, among others, arthritis, rheumatoid arthritis, atherosclerotic plaques, corneal graft neovascularization, wound healing, hypertrophic or keloid scars, proliferative retinopathy, diabetic retinopathy, macular degeneration, granulations, neovascular glaucoma and uveitis.

Additionally, rapid and excessive angiogenesis accompanies the growth of the placenta and solid tumors. Many tumors seem to produce factors which increase cell division of vascular endothelial cells and stimulate the migration and organization of endothelial cells into vessels resulting in neovascularization. In addition, factors which inhibit angiogenesis may be turned off. Activation of angiogenesis, therefore, appears to be an essential stage in tumor progression. Various mammalian endogenous molecules have been identified as angiogenic factors stimulating angiogenesis directly or indirectly. These stimulators of angiogenesis include basic fibroblast growth factor (bFGF), vascular endothelial cell growth factor (VEGF), tumor necrosis factor-α (TNF-α), and angiogenin.

The search for neovascularization inhibitors has been recently vigorously pursued. Currently, several antiangiogenic factors including thrombospondin, platelet factor-4, fumagillin, thalidomide angiostatin and endostatin are being studied. Several of these are in early clinical trials, e.g., fumagillin and thalidomide.

Since there is no effective treatment available and since angiogenic diseases present a serious medical problem there is an ongoing need for new and more efficient antiangiogenic agents.

Human hormones, such as growth hormone (hGH), prolactin (hPRL), placental lactogen (hPL) or growth hormone variant (hGH-V) are homologous protein hormones which are potent endogenous chemical substances asserting specific biological activities on their respective target organs. The biological activities of these hormones are not the same and they differ depending on the hormone and/or the hormone target organ. For example, growth hormone, which is a protein of the anterior lobe of the pituitary gland, promotes and regulates body growth and morphogenesis, fat mobilization and inhibitions of glucose utilization (*Trends Endocrinol. Metab.,* 3:117(1992)).

Prolactin is a known hormone produced by the pituitary gland in all mammals. The normal biological function and activity of prolactin in mammals include regulation of reproduction, osmoregulation, the stimulation of milk production by the mammary gland, the modulation of steroidogenesis in the gonads, the stimulation of maternal behavior, and the modulation of immune function (*Life Sci.,* 57:1 (1995)).

The human placenta expresses two proteins with significant structural homology to human growth hormone, namely human placental lactogen and a variant of human growth hormone, hGH-V, differing by 13 amino acid substitutions (*Hormonal Proteins Peptides,* 4:61 (1977)).

Human placental lactogen is somatotropic in fetal tissues and aids in stimulating mammary cell proliferation (*Endocrin. Rev.,* 12:316 (1991)). Human growth hormone variant rather than pituitary growth hormone regulates maternal metabolism during the second half of the pregnancy (*Endocrinology,* 133:1292 (1993)). As described in *Endocrinology,* 121:2055 (1987) rodent placentas express and secrete several proteins such as proliferin and proliferin-related peptide possessing biological actions similar to prolactin rather than growth hormone.

The human placenta serves as the major respiratory, nutritional and endocrine organ throughout fetal life and is critical to the survival and healthy development of the fetus. The placenta provides an intimate interface between the maternal and fetal blood supplies. Pathological impairment of placental invasion and poor vascular development has been associated with both fetal and maternal complications.

Intrauterine fetal growth restriction (IUGR) is a condition that affects approximately 500,000 pregnancies annually in the United States. As a result of poor placental blood supply, and decreased fetal oxygenation and nutrition, this condition results in small-for-dates infants. These infants have a neonatal mortality rate 6-10 times higher than that of normal infants and are at risk for pulmonary and neurological problems at birth.

Preeclampsia, a condition that affects approximately 250,000 American pregnancies each year, puts mothers and their fetuses at high risk. Maternal hypertension, renal failure, hepatic failure, coagulopathy, cerebral edema seizures and stroke are the potential consequences of this syndrome. Fetal morbidity is 5 times higher than normal in preeclampsia.

Pathological conditions involving excessive trophoblastic invasion, such as placenta accreta and gestational trophoblastic tumors, can cause devastating maternal complications including hemorrhage and metastatic neoplasia.

All the above placental conditions associated with dysregulation of the vasculature of the developing placenta can have profound maternal and chi child health consequences.

Thus, there is a need for diagnosing and treating vascular abnormalities of the placenta. These needs and others are addressed by the instant invention.

SUMMARY OF THE INVENTION

One aspect of the invention is an anti-angiogenic peptide substantially identical to about 10 to about 150 consecutive amino acids selected from the N-terminal end of human placental lactogen, human growth hormone, growth hormone variant hGH-V, or human prolactin, wherein the peptide (i) inhibits capillary endothelial cell proliferation and organization;

(ii) inhibits angiogenesis in chick chorioallantoic membrane; and (iii) binds to at least one specific receptor which does not bind an intact full length growth hormone, placental lactogen, prolactin, or growth hormone variant hGH-V.

A further aspect of the invention is an isolated nucleic acid encoding the anti-angiogenic peptide of the invention. The nucleic acid may be DNA or RNA, and may comprise cDNA sequences.

A further aspect of the invention is a host cell comprising the nucleic acid encoding the anti-angiogenic peptide of the invention. A further aspect of the invention is a method of producing the peptide of the invention, comprising expressing the nucleic acid in the host cell, and recovering the peptide.

A further aspect of the invention is a method of treating an angiogenic disease in a subject, the method comprising administering to a subject in need of such treatment an angiogenesis inhibitory effective amount of the antiangiogenic peptide of the invention.

A further aspect of the invention is a method of inhibiting tumor formation or growth in a patient, the method comprising administering to the patient an angiogenesis inhibitory effective amount of the antiangiogenic peptide of the invention.

A further aspect of the invention is a method for diagnosing a probable abnormality of placental vascularization during pregnancy comprising assaying a level of at least one of endogenous N-terminal fragments of growth hormone, prolactin, growth hormone variant hGH-V, and placental lactogen in a tissue sample from a patient; and comparing the level of the at least one of endogenous N-terminal fragments to an average level of the at least one of endogenous N-terminal fragments in a normal patient population;

wherein a level of the at least one of endogenous N-terminal fragments higher than the average level is a probable abnormality of placental vascularization during pregnancy.

A further aspect of the invention is a method of modulating vascularization of a patient's placenta, the method comprising administering to the patient an angiogenesis inhibitory effective amount of the anti-angiogenic peptide of the invention.

BRIEF DESCRIPTION OF THE DRAWINGS

FIG. 1 is a graph showing in vitro antiangiogenic effect of peptides of the invention detected as an inhibition of bovine brain capillary endothelial cell proliferation.

FIG. 2 is a graph of relative antiangiogenic activity in the chick chorioallantoic membrane of 16K N-terminal fragment peptides of human growth hormone, growth hormone variant hGH-V, human placental lactogen and human prolactin compared to their-respective intact 22 or 23K polypeptides and to a bovine serum albumin control.

FIG. 3 comprises FIGS. 3A-H, which are photographs of a subset of data from FIG. 2 comparing in vivo neovascularization of the chick chorioallantoic membrane following the treatment with the peptides of the invention.

FIG. 4 comprises FIGS. 4A-C. FIG. 4A is a Western blot analysis of tyrosine phosphorylation of mitogen-activated protein kinase. FIG. 4B is a graph depicting the percent level of inhibition of the bFGF stimulation of MAPK enzymatic activity by 16K N-terminal fragments. FIG. 3C is a graph depicting percent of stimulation over control by intact hormones without the presence of 16K fragment.

FIG. 5 comprises FIGS. 5A-5B. FIG. 5A depicts Western blot analysis of plasminogen activator inhibitor-1 protein levels and their quantitation following treatment with 16K N-terminal fragments or intact hormones. FIG. 5B is a Western blot analysis of plasminogen activator inhibitor (PAI-1) in untreated cells and cells treated with 16K N-terminal hGH, hGH, or a combination thereof.

FIG. 6 depicts a silver stained SDS-polyacrylamide gels showing cleavage of human prolactin by cathepsin D in vitro.

FIG. 7 is Western blot of human amniotic fluid prolactin showing cleavage of human prolactin in anmiotic fluid into fragments of 18 kD and 13 kD.

FIG. 8 comprises FIGS. 8A and 8B and depicts HPLC fractions of human prolactin cleaved with cathepsin D (8A) and assayed for their ability to inhibit bFGF-induced bovine brain capillary endothelial (BBCE) cell $^3$H-thymidine incorporation (8B).

FIG. 9 is a graph depicting increases in the number of 16K N-terminal hPRL binding sites in the human placenta throughout pregnancy expressed as specific binding.

DESCRIPTION OF THE PREFERRED EMBODIMENTS

The invention provides novel antiangiogenic peptides which are potent inhibitors of angiogenesis. These peptides in general correspond to about 10 to about 150 consecutive amino acids, more preferably about 10 to about 100, most preferably about 10 to about 50 consecutive amino acids selected from the amino acid sequences of N-terminal fragments of about 13-16 kD ("16K") derived from full length human growth hormone, the growth hormone variant hGH-V, human placental lactogen or human prolactin. As defined, herein peptides "substantially identical" in amino acid sequence are also included in the scope in the invention. The about 13-16K N-terminal fragments of the full length hormones are also referred to herein as "16K N-terminal human hormone" (16K hGH), "16K N-terminal human placental lactogen" (16K hPL), "16K N-terminal growth hormone variant hGH-V" (16K hGHV), and "16K N-terminal human prolactin" (16K hPRL). The peptides of the invention have the properties of (i) inhibiting capillary endothelial cell proliferation and organization; (ii) inhibiting angiogenesis in chick chorioallantoic membrane; and (iii) binding to at least one specific receptor which does not bind an intact full length growth hormone, placental lactogen or growth hormone variant hGH-V.

The finding disclosed herein that 16K N-terminal fragments cleaved from this group of hormones bind to at least one new, previously undisclosed receptor or receptors other than their own specific receptors known in the art and have specific and distinguishable antiangiogenic activity is surprising and unexpected. The full length intact hormones have no antiangiogenic activity but are angiogenic in some settings. Furthermore, the antiangiogenic activity of the 16K N-fragments is not mediated via the intact hormones' own specific receptors.

The peptides of the invention have similar biological potencies acting in the nM concentrations. Typically, one-half of the inhibitory action $IA_{50}$ is achieved at a very low concentration of about 0.8-1 nM. The peptides bind to the new receptor(s) with high affinity and in a saturable manner. Intact full length growth hormone, placental lactogen, growth hormone variant hGH-V, and bFGF do not compete for the same receptor site(s) and have different activities as well as levels of activities.

In in vitro assays, the peptides of the invention inhibit the growth of bovine brain capillary endothelial (BBCE) cell proliferation confirming their antiangiogenic activity. Additionally, the peptides inhibit the mitogenic activity of bFGF and VEGF. While 16K N-terminal human growth hormone has this activity, rat 16K N-terminal growth hormone is not antiangiogenic.

A. Angiogenesis, Angiogenic Conditions and Angiogenic Diseases

The peptides of the invention and their respective pharmaceutical compositions and preparations which are capable of inhibiting angiogenesis are useful for preventing or treating any disease or condition which is associated with or results in or from angiogenesis. Such diseases include formation of malignant tumors, angiofibroma, arteriovenous malformations, arthritis, such as rheumatoid arthritis, atherosclerotic plaques, corneal graft neovascularization, delayed wound healing, proliferative retinopathy such as diabetic retinopathy, macular degeneration, granulations such as those occurring in hemophilic joints, inappropriate vascularization in wound healing such as hypertrophic scars or keloid scars, neovascular glaucoma, ocular tumor, uveitis, non-union fractures, Osler-Weber syndrome, psoriasis, pyogenic glaucoma, retrolental fibroplasia, scleroderma, solid tumors, Kaposi's sarcoma, trachoma, vascular adhesions, chronic varicose ulcers, leukemia, and reproductive disorders such as follicular and luteal cysts and choriocarcinoma, among others.

Given their anti-angiogenic activity, the peptides of the invention are also suitable for use in a method of inhibiting mammalian cell proliferation and organization that depends on vascularization, including the selective inhibition of vascularization of tumors, tumor size reduction and elimination. Examples of tumors undergoing angiogenesis include but are not limited to angiofibroma, arteriovenous malformations, ocular tumors, all solid tumors, Kaposi's sarcoma, trachoma and choriocarcinoma.

The peptides of the invention may be used to assess and/or modulate the development of the vasculature of the placenta. Regulation of placental vascularization has important clinical implications, since two disorders of pregnancy, preeclampsia and intrauterine growth retardation, are associated with impairment of vascular development. No clinical tests exist to predict the occurrence of these disorders until pregnancy is seriously compromised.

The peptides of the invention can also be used as contraceptive agents.

B. Diagnostic Assays for Placental Dysfunction and Abnormal Vascularization

Measurement of the endogenous levels of at least one of naturally occurring N-terminal fragments of hGH, hGH-V, hPRL, or hPL, such as 16K hGH, 16K hGH-V, 16K hPL or 16K hPRL, in the blood or tissue sample of a pregnant women by, for example, radioimmunoassay provides a diagnostic assay for the probable impairment of vascular development associated with preeclampsia, intrauterine growth retardation, and placental dysfunction. The activity level of enzymes which generate such fragments, such as but not limited to endogenous cathepsin, thrombin, plasmin, or subtilisin, can also be measured as an indication of probable vascular abnormalities in the placenta. Measurements are typically done in the first trimester, but may be performed in the second and/or third trimesters.

Any technique known in the art for detecting levels of peptides or polypeptides of known function or sequence may be used for the diagnostic assay. Typically, the diagnostic assay would comprise assaying a level of at least one of endogenous N-terminal fragments of prolactin, growth hormone, growth hormone variant hGH-V, and placental lactogen in a tissue sample from a patient; and comparing the level of the at least one of endogenous N-terminal fragments to an average level of the at least one of endogenous N-terminal fragments in a normal patient population; wherein a level of the at least one of endogenous N-terminal fragments higher than the average level is a probable abnormality of placental vascularization during pregnancy.

The phrase "specifically binds to an antibody" or "specifically immunoreactive with", when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amont to other proteins present in the sample. Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

C. Production of the Peptides of the Invention

The peptides of the current invention can, for example, be synthesized, prepared from purified full-length hormones, or produced using recombinant methods and techniques known in the art. Although specific techniques for their preparation are described herein, it is to be within the that all appropriate techniques suitable for production of these peptides are intended to be within the scope of this invention.

Generally, these techniques include DNA and protein sequencing, cloning, expression and other recombinant engineering techniques permitting the construction of prokaryotic and eukaryotic vectors encoding and expressing each of the peptides of the invention.

In one mode, the peptides of this invention are conveniently obtained by isolation of intact growth hormone from the human pituitary gland or plasma and isolation of lactogen and growth hormone variant hGH-V. The isolated intact hormones may be glycosylated and cleaved to varying degrees.

In another mode, the peptides may be prepared by peptide synthesis according to method described in *Biotechnology and Applied Biochem.*, 12:436 (1990) or by methods described in *Current Protocols in Molecular Biology*, Eds. Ausubel, F. M., et al, John Wiley & Sons, N.Y. (1987).

The peptides of the invention may be produced by expression of a nucleic acid encoding a peptide of interest, or by cleavage from a longer length polypeptide encoded by the nucleic acid. Expression of the encoded polypeptides may be done in bacterial, yeast, plant, insect, or mammalian hosts by techniques well known in the art. As for example, 16K hPRL has been produced in eukaryotic HCT 116 cells. The cDNA coding for the 16K hPRL (stop 140) has been cloned into the mammalian expression vector pRC-CMV. The construct was transferred into the HCT116 human colon cancer cells and stably transfected cells expressing 16K hPRL (stop 140) were obtained. Either conditioned media or purified 16K hPRL (stop 140) from these cells were able to inhibit bFGF-induced BBCE proliferation.

In an embodiment, a peptide of interest of the invention is obtained by cloning the DNA sequence encoding an intact full length human hormone into a vector; modifying the DNA codon corresponding to the last amino acid of a desired 16K N-terminal hormone fragment to a stop codon by mutagenesis techniques known in the art; and transforming a host cell with the modified nucleic acid to allow expression of the encoded peptide. In a further embodiment, the cloned hormone DNA is engineered to create a proteolytic cleavage site within the hormone polypeptide. The polypeptide is then cleaved after production in the host to generate the peptide of interest. Examples of mutagenesis techniques include, for example, methods described in *Promega Protocols and Applications Guide*, Promega Corp, Madison, Wis., p. 98 (1891) or according to *Current Protocols in Molecular Biology*, supra.

If the peptide is to be synthesized via a prokaryotic vector, the DNA sequence encoding human hormone preferably does not contain a signal peptide sequence. In addition, a DNA codon for methionine (Met) is typically inserted upstream of 5' to the first DNA codon of the coding sequence.

Methods for cloning DNA into a vector and for inserting, deleting and modifying polynucleotides and for site directed mutagenesis are described, for example, in *Promega Protocols and Applications Guide*, supra. Cells or bacteria may be transfected with a vector, preferably with an expression vector, having the desired DNA sequence attached thereto, by known techniques including heat shock, electroporation, calcium phosphate precipitation and lipofection, among others. The terminal peptides or other analogues or fragments may then be extracted and purified by, for example, high pressure liquid chromatography (HPLC), ion exchange chromatography or gel permeation chromatography. However, other methods and techniques known in the art of conducting the different steps or combinations of these steps necessary to derive the peptide of this invention or equivalent steps are contemplated to be within the scope of this invention.

The following terms are used to describe the sequence relationships between two or more nucleic acids or polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence.

Optimal alignment of sequences for aligning a comparison window may, for example, be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman Proc. Natl. Acad. Sci. U.S.A. 85:2444 (1988), or by computerized implementations of these algorithms (GAP, BESTFIT, FASTA, and TFASTA in the Wisconsin Genetics Software Package Release 7.0, Genetics Computer Group, 575 Science Dr., Madison, Wis.).

As applied to polypeptides, the terms "substantial identity" or "substantial sequence identity" mean that two peptide sequences, when optimally aligned, such as by the programs GAP or BESTFIT using default gap weights, share at least 80 percent sequence identity, preferably at least 90 percent sequence identity or more. "Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties such as charge or polarity are not likely to effect the properties of a protein. Examples include glutamine for asparagine or glutamic acid for aspartic acid.

The phrase "substantially purified" or "isolated" when referring to a peptide or protein, means a chemical composition which is essentially free of other cellular components. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. Generally, a substantially purified or isolated protein will comprise more than 80% of all macromolecular species present in the preparation. Preferably, the protein is purified to represent greater than 90% of all macromolecular species present. More preferably the protein is purified to greater than 95%, and most preferably the protein is purified to essential homogeneity, wherein other macromolecular species are not detected by conventional techniques.

D. Nucleic Acids of the Invention

Also provided herein are isolated nucleic acids that comprise DNA or RNA sequences encoding the peptides of the invention. The nucleic acids of the invention may further comprise vectors for expression of the peptides of the invention. In some embodiments the DNA may comprise cDNA sequences encoding full-length hormones or sequences encoding N-terminal regions of the hormones. It is understood by one of ordinary skill in the art that because of degeneracy in the genetic code, substitutions in the nucleotide sequence may be made which do not result in changes in the encoded amino acid sequence. Thus, "substantially identical" sequences as defined herein are included in the scope of the invention. It is further understood by one of ordinary skill in the art that both complementary strands of any DNA molecule described herein are included within the scope of the invention.

The terms "substantial identity" or "substantial sequence identity" as applied to nucleic acid sequences and as used herein and denote a characteristic of a polynucleotide sequence, wherein the polynucleotide comprises a sequence that has at least 85 percent sequence identity, preferably at least 90 to 95 percent sequence identity, and more preferably at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

E. Agonists

In some embodiments of the invention, agonists of the receptor(s) for the anti-angiogenic peptides are provided. Such agonists include but are not limited to mutants of the peptides of the invention and peptide, non-peptide, and peptidomimetic analogs of the peptides of the invention.

F. Treatment Protocols

The method for treatment of angiogenic diseases comprises administering to a patient an angiogenesis inhibitory amount of one or more peptides of the invention. As used herein, the term "treatment" is intended to refer to the prevention, amelioration, or reduction in severity of a symptom of angiogenesis. Similarly, an angiogenic-inhibitory effective dose of a peptide of the invention is a dose sufficient to prevent, ameliorate, or reduce the severity of a symptom of angiogenesis.

The peptides of the invention may be administered singly or in combination with each other or other angiogenesis inhibitory agents.

Typically, the peptides of the invention are administered in an amount of about 8 micrograms to 3,000 µg/kg per day, and more preferably about 20 to 1,500 µg/kg per day preferably once or twice daily. However, other amounts, including substantially lower or higher amounts, may also be administered. The peptides of the invention are administered to a human subject in need of antiangiogenic treatment intramuscularly, subcutaneously, intravenously, intratumorally, by any other acceptable route of administration. In the case of ocular angiogenic diseases, the peptide may also be administered topically to the eye.

Both preventative or therapeutic uses, such as the prevention and/or treatment of diabetic patients to avoid a decrease of their vision produced by vascularization of the retina, contraceptive applications, and the long-term treatment of cancer patients such as for avoiding the reformation of malignant tumors after surgery or chemotherapy are intended.

As it is well-known that some patients, e.g. diabetic patients, suffer from vision loss over a period of time, the present peptide may be suitably utilized for the inhibition or retardation of this process. When utilized for this application, the composition of the invention to be administered may comprise an amount of the peptide about 12 to 3,500 µg/kg per day, and preferably about 25 to 2,700 µg/kg per day. However, different amounts of the peptide may also be administered as seen suitable by a practitioner for specific cases. Smaller amounts may be administered by injection into the anterior chamber of the eye.

For this or any other application the peptide of this invention may be administered in an amount of about 10 to 3,750 µg/kg, and more preferably about 15 to 1,600 µg/kg. Any means of administration is suitable.

G. Gene Therapy

Gene therapy utilizing recombinant DNA technology to deliver nucleic acids encoding peptides of the invention into patient cells or vectors which will supply the patient with gene product in vivo is also contemplated within the scope of the present invention.

Gene therapy techniques have the potential for limiting the exposure of a subject to a gene product, such as polypeptide, by targeting the expression of the therapeutic gene to a tissue of interest, such as skeletal muscle, myocardium, vascular endothelium or smooth muscle, or solid or circulating tumor cells. For example, WIPO Patent Application Publication No. WO 93/15609 discloses the delivery of interferon genes to vascular tissue by administration of such genes to areas of vessel wall injury using a catheter system. In another example, an adenoviral vector encoding a protein capable of enzymatically converting a prodrug, a "suicide gene", and a gene encoding a cytokine are administered directly into a solid tumor.

Other methods of targeting therapeutic genes to tissues of interest include the three general categories of transductional targeting, positional targeting, and transcriptional targeting (for a review, see, e.g., Miller et al. *FASEB J.* 9:190-199 (1995)). Transductional targeting refers to the selective entry into specific cells, achieved primarily by selection of a receptor ligand. Positional targeting within the genome refers to integration into desirable loci, such as active regions of chromatin, or through homologous recombination with an endogenous nucleotide sequence such as a target gene. Transcriptional targeting refers to selective expression attained by the incorporation of transcriptional promoters with highly specific regulation of gene expression tailored to the cells of interest.

Examples of tissue-specific promoters include a liver-specific promoter (Zou et al., *Endocrinology* 138:1771-1774 (1997)); a small intestine-specific promoter (Olivera et al., *J. Biol. Chem.* 271:31831-31838 (1996)); the promoter for creatine kinase, which has been used to direct of dystrophin cDNA expression in muscle and cardiac tissue (Cox et al., *Nature* 364:725-729 (1993)); and immunoglobulin heavy or light chain promoters for the expression of suicide genes in B cells (Maxwell et al., *Cancer Res.* 51:4299-4304 (1991)). An endothelial cell-specific regulatory region has also been characterized (Jahroudi et al., *Mol. Cell, Biol.* 14:999-1008 (1994)). Amphotrophic retroviral vectors have been constructed carrying a herpes simplex virus thymidine kinase gene under the control of either the albumin or alpha-fetoprotein promoters (Huber et al., *Proc. Natl. Acad. Sci. U.S.A.* 88:8039-8043 (1991)) to target cells of liver lineage and hepatoma cells, respectively. Such tissue specific promoters can be used in retroviral vectors (Hartzoglou et al., *J. Biol. Chem.* 265:17285-17293 (1990)) and adenovirus vectors (Friedman et al., *Mol. Cell. Biol.* 6:3791-3797 (1986)) and still retain their tissue specificity.

Other elements aiding specificity of expression in a tissue of interest can include secretion leader sequences, enhancers, nuclear localization signals, endosmolytic peptides, etc. Preferably, these elements are derived from the tissue of interest to aid specificity.

Viral vector systems useful in the practice of the instant invention include but are not limited to adenovirus, herpesvirus, adeno-associated virus, minute virus of mice (MVM), HIV, sindbis virus, and retroviruses such as Rous sarcoma virus, and MoMLV. Typically, the nucleic acid encoding the therapeutic polypeptide or peptide of interest is inserted into such vectors to allow packaging of the nucleic acid, typically with accompanying viral DNA, infection of a sensitive host cell, and expression of the polypeptide or peptide of interest.

In still other embodiments of the invention, nucleic acid encoding a therapeutic polypeptide or peptide of interest is conjugated to a cell receptor ligand for facilitated uptake (e.g., invagination of coated pits and internalization of the endosome) through a DNA linking moiety (Wu et al., *J. Biol. Chem.* 263:14621-14624 (1988); WO 92/06180). For example, the DNA constructs of the invention can be linked through a polylysine moiety to asialo-oromucoid, which is a ligand for the asialoglycoprotein receptor of hepatocytes.

Similarly, viral envelopes used for packaging the recombinant constructs of the invention can be modified by the addition of receptor ligands or antibodies specific for a receptor to permit receptor-mediated endocytosis into specific cells (e.g., WO 93/20221, WO 0.93/14188; WO 94/06923). In some embodiments of the invention, the DNA constructs of the invention are linked to viral proteins, such as adenovirus particles, to facilitate endocytosis (Curiel et al., *Proc. Natl. Acad. Sci. U.S.A.* 88:8850-8854 (1991)). In other embodiments, molecular conjugates of the instant invention can include microtubule inhibitors (WO 94/06922); synthetic peptides mimicking influenza virus hemagglutinin (Plank et al., *J. Biol. Chem.* 269:12918-12924 (1994)); and nuclear localization signals such as SV40 T antigen (WO 93/19768).

The nucleic acid can be introduced into the tissue of interest in vivo or ex vivo by a variety of methods. In some embodiments of the invention, the nucleic acid is introduced into cells by such methods as microinjection, calcium phosphate precipitation, liposome fusion, or biolistics. In further embodiments, the nucleic acid is taken up directly by the tissue of interest. In other embodiments, nucleic acid is packaged into a viral vector system to facilitate introduction into cells.

In some embodiments of the invention, the compositions of the invention are administered ex vivo to cells or tissues explanted from a patient, then returned to the patient. Examples of ex vivo administration of gene therapy constructs include Arteaga et al., *Cancer Research* 56(5):1098-1103 (1996); Nolta et al., *Proc Natl. Acad. Sci. USA* 93(6): 2414-9 (1996); Koc et al., *Seminars in Oncology* 23 (1):46-65 (1996); Raper et al., *Annals of Surgery* 223(2):116-26 1996); Dalesandro et al., *J. Thorac. Cardi. Surg.* 11(2):416-22 (1996); and Makarov et al., *Proc. Natl. Acad. Sci. USA* 93(1):402-6 (1996).

H. Formulations and Pharmaceutical Compositions

The compositions of the invention will be formulated for administration by manners known in the art acceptable for administration to a mammalian subject, preferably a human. In some embodiments of the invention, the compositions of the invention can be administered directly into a tissue by injection or into a blood vessel supplying the tissue of interest. In further embodiments of the invention the compositions of the invention are administered "locoregionally", i.e., intravesically, intralesionally, and/or topically. In other embodiments of the invention, the compositions of the invention are administered systemically by injection, inhalation, suppository, transdermal delivery, etc. In further embodiments of the invention, the compositions are administered through catheters or other devices to allow access to a remote tissue of interest, such as an internal organ. The compositions of the invention can also be administered in depot type devices, implants, or encapsulated formulations to allow slow or sustained release of the compositions.

In order to administer therapeutic agents based on, or derived from, the present invention, it will be appreciated that suitable carriers, excipients, and other agents may be incorporated into the formulations to provide improved transfer, delivery, tolerance, and the like.

A multitude of appropriate formulations can be found in the formulary known to all pharmaceutical chemists: Remington's Pharmaceutical Sciences, (15th Edition, Mack Publishing Company, Easton, Pa. (1975)), particularly Chapter 87, by Blaug, Seymour, therein. These formulations include for example, powders, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax.

Any of the foregoing formulations may be appropriate in treatments and therapies in accordance with the present invention, provided that the active agent in the formulation is not inactivated by the formulation and the formulation is physiologically compatible.

The quantities of active ingredient necessary for effective therapy will depend on many different factors, including means of administration, target site, physiological state of the patient, and other medicaments administered. Thus, treatment dosages should be titrated to optimize safety and efficacy. Typically, dosages used in vitro may provide useful guidance in the amounts useful for in situ administration of the active ingredients. Animal testing of effective doses for treatment of particular disorders will provide further predictive indication of human dosage. Various considerations are described, for example, in *Goodman and Gilman's the Pharmacological Basis of Therapeutics,* 7th Edition (1985), MacMillan Publishing Company, New York, and *Remington's Pharmaceutical Sciences* 18th Edition, (1990) Mack Publishing Co, Easton Penn. Methods for administration are discussed therein, including oral, intravenous, intraperitoneal, intramuscular, transdermal, nasal, iontophoretic administration, and the like.

The compositions of the invention may be administered in a variety of unit dosage forms depending on the method of administration. For example, unit dosage forms suitable for oral administration include solid dosage forms such as powder, tablets, pills, capsules, and dragees, and liquid dosage forms, such as elixirs, syrups, and suspensions. The active ingredients may also be administered parenterally in sterile liquid dosage forms. Gelatin capsules contain the active ingredient and as inactive ingredients powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The concentration of the compositions of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The compositions of the invention may also be administered via liposomes. Liposomes include emulsions, foams, micelles, insoluble monolayers, liquid crystals, phospholipid dispersions, lamellar layers and the like. In these preparations the composition of the invention to be delivered is incorporated as part of a liposome, alone or in conjunction with a molecule which binds to a desired target, such as antibody, or with other therapeutic or immunogenic compositions. Thus, liposomes either filled or decorated with a desired composition of the invention can delivered systemically, or can be directed to a tissue of interest, where the liposomes then deliver the selected therapeutic/immunogenic peptide compositions.

Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety in, e.g., Szoka et al. Ann. Rev. Biophys. Bioeng. 9:467 (1980), U.S. Pat. Nos. 4,235,871, 4,501,728, 4,837,028, and 5,019,369, incorporated herein by reference.

A liposome suspension containing a composition of the invention may be administered intravenously, locally, topically, etc. in a dose which varies according to, inter alia, the manner of administration, the composition of the invention being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more compositions of the invention, and more preferably at a concentration of 25%-75%.

For aerosol administration, the compositions of the invention are preferably supplied in finely divided form along with a surfactant and propellant. Typical percentages of compositions of the invention are 0.01%-20% by weight, preferably 1%-10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25-5%. The balance of the composition is ordinarily propellant. A carrier can also be included, as desired, as with, e.g., lecithin for intranasal delivery.

The compositions of the invention can additionally be delivered in a depot-type system, an encapsulated form, or an implant by techniques well-known in the art. Similarly, the compositions can be delivered via a pump to a tissue of interest.

The compositions of the invention are typically administered to patients after the onset of symptoms, although treatment can also be prophylactic in some embodiments. Typically, treatment with direct administration of polypeptides is done daily, weekly, or monthly, for a period of time sufficient to reduce, prevent, or ameliorate symptoms. Treatment with the nucleic acids of the invention is typically done at intervals of several months. In some embodiments, administration of the compositions of the invention is done in utero.

The composition of the invention may also be provided in the kit as a slow-release composition such as a daily, weekly, monthly unit provided as a sponge, dermal patch, subcutaneous implant and the like in a wrapping or container as described above. In this case, the patient may release a unit of the composition from the container and applies it as indicated in the kit instructions. The composition may then be replaced at the end of the specified period by a fresh unit, and so on.

The present composition may also be administered by means of injection, as indicated above. Typically, the peptide may be administered by itself, or, for instance, in the case of a diabetic, in a composition also comprising insulin. The same is true for the slow-release forms of the composition. Similarly, the peptide of the invention may be administered in a composition that also comprises another drug. One such case is that of cancer patients, where different anti-cancer drugs such as chemotherapeutic or contrast agents and target-specific antibodies, among others, may be provided in a composition also comprising the peptide of the invention. The proportion of peptides to the other drug(s) and carrier may be adjusted accordingly.

The levels of the delivered peptide to a patient may be monitored by immunoassay. To determine the level of the peptide of invention in blood following administration, e.g., intramuscular or subcutaneous administration, an antibody assay may be performed with antibodies specific to the peptide sequence by any of the protocols known in the art. Polyclonal or monoclonal antibodies or the 16K N-terminal fragment receptor may be utilized. The level of the peptide in blood may then be correlated with the progress of the inhibition of any of the diseases the patient is afflicted with.

The following examples are intended to illustrate, not limit the scope of this invention.

EXAMPLE 1

Antiangiogenic Activity of 16K N-Terminal Fragments of Human Growth Hormone, Human Placental Lactogen. Human Prolactin. and Human Growth Hormone Variant hGH-V 16K N-terminal antiangiogenic agents were derived from full length human growth hormone, human growth hormone variant hGH-V, human placental lactogen and prolactin. These peptides were tested in vivo and in vitro for their binding and antiangiogenic activity in assays described in below. Results of these testings are illustrated in FIGS. 1-5.

A. In vitro and in vivo Angiogenic Inhibitory Activity

Biological antiangiogenic activity of the 16K N-terminal fragments was tested in bovine brain capillary endothelial cell assay, as well as in vivo chick chorioallantoic membrane assay. The in vitro and in vivo antiangiogenic inhibitory characteristics of the peptides of the invention were determined and are described in Sections 1 and 2, below.

1. In vitro Antiangiogenic Activity

In vitro, the peptides were tested for their ability to inhibit the basal or stimulated growth of bovine brain capillary endothelial cells. Fibroblast growth factors were used to stimulate endothelial cell growth. Experimental procedures for these tests are described in below.

In vitro inhibition of bFGF stimulation of bovine brain capillary endothelial (BBCE) cell proliferation is shown in FIG. 1.

FIG. 1 is a graph showing inhibition of bovine brain capillary endothelial cell proliferation expressed as the percent of inhibition of the stimulation by bFGF.

Experimental design for studies seen in FIG. 1 was as follows. On day 1, 104 bovine brain capillary endothelial (BBCE) cells were plated in 24-well plates in 0.25 ml Dulbecco's modified Eagle's medium obtained from Gibco, containing 10% fetal calf serum, human recombinant bFGF (1 ng/ml, Promega), with purified peptide (100, 50, 10, 5, 2, 1, 0.5, 0.2, or 0.1 nM) prepared as discussed below. Wells containing cells, medium and serum without presence of angiogenesis stimulator basic fibroblast growth factor (bFGF) were included as basal-growth controls. On day 3, bFGF (1 ng/ml) and 100, 50, 10, 5, 2, 1, 0.5, 0.2, or 0.1 nM purified protein were added once again to the dishes. On day 4, the cells were incubated with 500,000 cpm of ($^3$H) thymidine for 4 hours, washed in 5% trichloroacetic acid, solubilized in NaOH, and counted as previously described in *Endocrinology*, 133: 1292 (1993). Each point seen in FIG. 1 represents the mean of triplicate wells. The experiments were repeated at least three times. Similar results were obtained in each experiment.

The data seen in FIG. 1 are expressed as percentages of the inhibition of the stimulation obtained with bFGF alone which was considered to be 100% when the hormone concentration was less than 0.1 nM, 0% being the basal growth level.

As seen from FIG. 1, when the concentration of the hormone peptide was zero or lower than 0.1 nM, there was 100% bFGF induced BBCE cell proliferation that was 100% angiogenic. However, following the treatment with 0.2 nM 16K hGH-V or other 16K fragments, the drop in bFGF stimulation was observed. When the concentration of the 16K peptides was increased to 1 nM, the drop in bFGF stimulation was substantial from 100 to about 60%. At 10 nM concentration of the 16K peptides, the bFGF-stimulation dropped to about 10-20%. When the concentration of the 16K peptides was increased to about 50 nM, the bFGF stimulation of BBCE cell proliferation was completely suppressed.

FIG. 1, therefore, clearly shows that purified 16K hormone fragments of the invention are able to substantially inhibit the cell proliferation even in concentrations as low as 1 nM. At concentrations from 10-50 nM, these peptides completely inhibit endothelial cell proliferation in vitro. Symbols used for individual 16K peptides are: (■) 16K hPRL; (♦) 16K hPL; (●) 16K hGH; (▲) 16K hGH-V.

As seen in FIG. 1, in vitro 16K hPL, 16K hGH, and 16K hGH-V fragments and 16K hPRL used as a comparative control administered in concentrations from 0.1 to 100 nM almost completely inhibit induced basic fibroblast growth factor (bFGF) proliferation of bovine brain capillary endothelial (BBCE) cells. Inhibition of cell proliferation was dose dependent and the concentration required for half maximal inhibition ($IC_{50}$) ranged from 1 to 5 nM for the various 16K N-terminal fragment peptides.

2. In vivo Antiangiogenic Activity

In vivo, the peptides of the invention were tested for their ability to inhibit basal or stimulated capillary formation in developing chick embryos, using the chick chorioallantoic membrane assay (CAM) described below. The ability to inhibit the development of capillaries in the chick chorioallantoic membrane is a measure of in vivo antiangiogenic activity. The peptides were applied to the chorioallantoic membrane by local placement of methylcellulose disks containing the peptide.

In vivo studies using chick chorioallantoic membrane (CAM) assay are shown in FIGS. 2 and 3.

FIG. 2 shows the antiangiogenic effect of the peptides of the invention calculated as the percentage of eggs showing anti-angiogenic response in the CAM assay. The procedure is described below.

FIG. 2 compares antiangiogenic activity in the chick chorioallantoic membrane assay of the intact full length hPRL, hGH, hGH-V and hPL to the antiangiogenic activity of their respective 16K N-terminal fragment peptides.

The antiangiogenic activity is described as antiangiogenic index expressed in percent. Bovine serum albumin (BSA) was used as a protein control.

As seen from FIG. 2, neither BSA nor any of the full length intact hormones had any antiangiogenic effect. Of the 16K N-terminal fragment peptides, the highest antiangiogenic index was observed for 16K hPRL and for 16K hGH, both having antiangiogenic index close to 100%. The antiangiogenic index of 16K hGH-V was between 80-85% and antiangiogenic index of 16 K hPL was around 90%.

These findings show that antiangiogenic activity of 16K N-terminal fragments studied is specific to the N-terminal region of the full hormones and the locus of this activity is located within about 16K of the N-terminus. These findings are unexpected and surprising because the full length hormones give no indication of any such activity.

FIG. 3 shows photographs of results of the chick chorioallantoic membrane (CAM) assay following the treatment with 16K hGH, 16K hGH-V, 16K hPL and 16K hPRL compared to their respective full length-hormones and to a bovine serum albumin control. FIG. 3 describes the inhibition of angiogenesis in early stage CAM assay.

For this study, on day 3 of development, fertilized chick embryos were removed from their shells and placed in plastic Petri dishes. On day 6, 5 mm disks of methylcellulose (0.5%, Sigma) containing 20 μg of 16K N-terminal fragments or intact molecules and 2 μg bovine serum albumin (BSA) were laid on the advancing edge of the chick CAM, as described below. After a 48-hour exposure, white India ink was injected into the chorioallantoic sac for photographic purposes. Under these conditions, the disks are visible by light reflection and the black arrow delineates the border of the disk or the border of the avascular area, if present.

FIG. 3 shows photographs of neovascularization of chicken embryo subjected to treatment with BSA, (upper panel 1) serving as a protein control, to treatment with 16K peptides of the invention (upper panels 2-5) and to the treatment with intact full length hormones (lower panels 6-9). The sites of the disks, identified as black arrow, show clearly that at sites of treatment with 16K N-terminal fragments, the neovascularization is almost completely or substantially suppressed. In lower panels, which show results obtained following the treatment with intact full length hormones high neovascularization is clearly visible. Such high neovascularization is completely unobservable in embryos treated with the 16K peptides of the invention. In in vivo CAM assays 16K hPRL, 16K hPL, 16K hGH and 16K hGH-V inhibited capillary formation as seen in FIGS. 2 and 3, confirming their antiangiogenic activity. Large areas devoid of capillaries were observed surrounding the methylcellulose disks containing the 16K fragments. No such activity was observed when cellulose disks contained BSA or the intact full length hormone molecules.

These findings show that the peptides of the invention inhibit both cell proliferation in vitro and also inhibit neovascularization in vivo.

Quantitation of the in vivo antiangiogenic effect of the peptides of the invention expressed as antiangiogenesis index is seen in FIG. 2.

In view of the above described in vitro and in vivo results which indicate that the 16K N-terminal fragments of hPRL, hGH, hPL, and hGH-V hormones possess different biological properties than the intact full length hormones from which they are derived, the studies were performed to determine whether these peptides act on separate receptors.

For this purpose, a series of studies was performed to investigate the effects of the 16K N-terminal fragment peptides as well as 16K fragment of human prolactin on activation of mitogen-activated protein kinase (MAPK) in bovine brain capillary endothelial (BBCE) cells.

Both basic fibroblast growth factor (bFGF) and vascular endothelial growth factor (VEGF) are known mitogens which activate the so called mitogen-activated protein kinase (MAPK) activity. The activity of MAPK, therefore, is a good indicator of mitogenic activity or its inhibition. Kinase activity can indirectly assessed by determining the level of tyrosine phosphorylation with a phosphotyrosine antibody or directly by measuring phosphorylation of a substrate.

The activation of MAPK was assessed indirectly by Western analysis using a phosphotyrosine antibody and directly by both in vitro and in gel enzymatic assays. Results are seen in FIG. 4.

FIG. 4 represents a Western blot analysis of tyrosine phosphorylation of MAPK (FIG. 4A), and the percentage level of inhibition of the bFGF stimulation of MAPK enzymatic activity by 16K fragments (FIG. 4B) compared to % of stimulation over control without 16K fragment (FIG. 4C). Stimulation of the tyrosine phosphorylation of MAPK by bFGF was blocked by the addition of 16K hGH, 16K hGH-V and 16K hPL as well as 16K hPRL (FIG. 4C).

As seen in FIG. 4, 16K fragments inhibit bFGF-dependent MAPK tyrosine phosphorylation and activity, while full-length hormones stimulate these processes in the absence of bFGF. For this study, cell lysates and phosphotyrosine Western blots were prepared and in-gel MAPK activity was measured as previously described in EMBO J., 2:493 (1983). BBCE cells (105) were plated in 60-mm plates in 1 ml Dulbecco's modified Eagle's medium (DMEM) Gibco, containing 10% calf serum. Twenty-four hours after plating, the cells were transferred to DMEM containing 0.5% calf serum and incubated for 48 hours to induce quiescence. The cells were treated for 5 min with 10 nM of the purified 16K hGH, 16K hGH-V, 16K hPL or 16K hPRL and with 250 µM bFGF, or for 10 minutes with 10 nM of the intact full length corresponding hormone without bFGF. Control was left untreated. To terminate the incubation, the medium was removed by suction and the cells were washed twice with phosphate buffer solution (PBS). Then 250 µl lysis buffer containing 20 mM Tris-HCl pH 8; 137 mM NaCl; 10% glycerol; 1% Triton X100; 1 mM orthovanadate and protease inhibitors leupeptin (2 µM), aprotinin (0.14 µ/ml) Pefablock (1 mM) was added to the plates and the samples were shaken at 4° C. for 20 minutes.

FIG. 4A, P-Tyr panel—left side panel shows the inhibition of the bFGF-induced phosphorylation of the p42 and p44 MAPK which are 42 and 44K mitogen-activated kinases, respectively, also called erk-1 and erk-2. Right side panel shows the stimulation of the MAPK by the full length hormones in the absence of bFGF. Cell lysate proteins were separated by SDS-PAGE, transferred to PVDF membranes, and probed with an anti-phosphotyrosine antibody (4G10, UBI, 1/2000 dilution). In FIG. 4A MAPK panel was used to verify the identity of the tyrosine phosphorylated bands and to control protein loading, the Western Blot shown in the P-Tyr Panel was stripped and reprobed with an anti-MAPK antibody (erk: 1 ct, UBI, 1/10,000 dilution).

Level of inhibition of the stimulation of MAPK enzymatic activity by 16K N-terminal fragments of the invention is seen in FIG. 4B. Results are compared to their respective intact hormone controls (FIG. 4C).

FIGS. 4B and 4C show in-gel MAPK activity. For this study, cell lysates were resolved by SDS-PAGE in gels containing 0.5 mg/ml myelin basic protein (MBP) as discussed below. After electrophoreses, the gel proteins were denatured, renatured, and subjected to an in situ kinase reaction with 100 µCi of (γ-32) ATP. The gels were then dried and autoradiographed. 32P incorporated into MBP was quantified by a phosphorimager. Numbers at the bottom of the histograms represent the number of experiments performed.

FIGS. 4B and 4C show comparative results of MAPK activity, expressed as percent of bFGF stimulation. The bFGF stimulation of MAPK activity was 100%. When the samples were submitted to treatment with both bFGF and 16K N-terminal fragment peptides of the invention, the bFGF-induced MAPK activity was inhibited in all cases to less than 25%, with greatest suppression of MAPK activity observed after treatment with the 16K hGH suppressing the MAPK activity to about 10%.

FIG. 4C shows the stimulation of MAPK activity with intact full length hormone in the absence of bFGF. As seen from comparison of FIGS. 4B and 4C when the full length hormones were used instead of 16K N-terminal fragments, the intact molecules seen in FIG. 4C actually stimulated the tyrosine phosphorylation of MAPK. The inhibition of bFGF-stimulated MAPK enzymatic activity by the 16K N-terminal fragments ranged between 75 and 85% (FIG. 4B), while the intact molecules actually stimulated MAPK activity.

The inhibition of the bFGF-induced stimulation of tyrosine phosphorylation and activation of MAPK by the 16K N-terminal fragments in contrast to the stimulations by the intact hormones clearly shows that the intact full length hormone and their 16K N-terminal fragments act on different receptors and have opposite effects on MAPK activation.

The above discussed results were further confirmed by the study performed to determine the effect of the peptide of the invention on the expression of plasminogen activator inhibitor (PAI). Secretion of type-1 plasminogen activator inhibitor (PAI-1) by migrating endothelial cells limits the degradation by urokinase plasminogen activator (uPA) of the extracellular matrix and thus prevents angiogenesis. Determination of whether or not the 16K peptides stimulate the expression of PAI-1 was performed and is described in FIG. 5.

FIG. 5 is a Western blot analysis of the effect of the peptides of the invention on PAI-1 protein levels and their quantitation (FIG. 5A) and Western blot analysis of PAI-1 in untreated cells and cells treated with hGH, 16K hGH, or both (FIG. 5B).

For this study, cell lysates were prepared as described in EMBO J., 2: 493 (1985). BBCE ($10^5$) cells were plated in 24-well plates in 1 ml Dulbecco's modified Eagle's medium (DMEM) containing lot calf serum. Twenty-four hours after plating, the cells were treated for 16 hours with purified 16K fragments or full-length hormone (10 nM) in serum-free DMEM. Untreated well was used as a control. 20 µl cell lysate was resolved by SDS-PAGE (10-4%) and the separated proteins transferred to a nitrocellulose membrane. The blots were blocked for 1 hour with 5% milk in Tris-buffered saline with 0.1% Tween 20 and probed for 2 hours with mouse anti-bovine PAI-1 monoclonal antibody obtained from Gibco, at 1:2000 dilution. The antigen-antibody complex was detected with horseradish-peroxidase-conjugated secondary antibody and an enhanced chemiluminescence system (ECL, Amersham).

FIG. 5A shows the effect of 16K N-terminal peptides of the invention on the expression of PAI-1 compared to the effect of intact hormones. FIG. 5A shows that 16K fragments stimulate PAI-1 expression, where as the full length hormones have no effect. PAI-1 stimulation induced by 16K fragments, expressed as fold stimulation, clearly shows that all four 16K peptides stimulate PAI-1 expression about 4 times that of control levels or levels observed following treatment with the intact hormones.

In the competition experiment shown in FIG. 5B, the effects of 16K hGH (10 nM), intact hGH (50 nM), and a mixture of 16K hGH and hGH were compared with controls. As seen from FIG. 5B, treatment with intact hGH resulted in no stimulation of PAI-1 relative to the control. Treatment with 16K hGH alone stimulated PAI-1 expression while additions of intact hGH had no effect on the activity of 16K hGH.

As seen in FIG. 5A, treatment of BBCE cells for 16 hours with each of the 16K fragments stimulated the expression of PAI-1 by approximately 300%. Treatment with their corresponding intact molecules had no effect on the expression of PAI-1, nor did addition of a five fold excess of hGH affect the stimulatory action of 16K hGH as seen in FIG. 5B.

These data further support the conclusion that the 16K fragments signal through a different receptor than intact molecules. These data also clearly show that the 16K fragments are not acting as antiangiogenic factors via the bFGF receptors since the activity of the PAI-1 is independent of the action of bFGF.

EXAMPLE 2

Endogenous 16K N-terminal Fragments in the Placenta

The interaction of fetal and maternal cells at the placental-decidual interface in eutherian mammals has been the subject of intensive investigation during the last two decades. Variation among species is dramatic. The most complex interactions are observed in hemochorial placentation, e.g. in human and mouse, where fetal trophoblast cells are in direct contact with the maternal circulation.

The establishment of adequate placental vascularization is critical to the survival of the developing conceptus, and requires extensive proliferation and remodeling of the decidual vascular tree. If vasculogenic mechanisms of placentation are similar to those reported for tumor invasion there are at least two forces driving the acquisition of the new blood supply. Maternal endothelial cells are recruited toward the placenta and concomitantly, placental cells migrate toward proliferating maternal vessels.

The factors that prepare the endometrial capillary bed to allow implantation and subsequent placental vascularization are virtually unknown (*Obstet. Gynecol. Surv.*, 50:668-97 (1995)), yet these are likely to be under exquisite regulation. Failure of adequate placental vascularization is believed to be the primary pathogenetic defect in two common human pregnancy complications, namely in preeclampsia (Ann. Med., 25:243-9 (1993)) and in intrauterine fetal growth restriction (IUGR) (Am. J. Obstet. Gynecol., 170:838-841 (1994)). By contrast, excessive trophoblastic invasion is associated with placenta accreta and gestational trophoblastic neoplasia.

Attachment of the implanting human placenta to the maternal decidua is achieved by contact between anchoring villi of the chorion frondosum and the decidua basalis. The characteristic hemochorial vascular anatomy of the human placenta provides a unique environment for oxygen, nutrient and waste product exchange. Irregular lobes or cotyledons separated by septa demarcate the maternal surface of the developing placenta. Normally, each cotyledon is supplied by one of approximately 120 maternal uterine spiral arteries.

The classical radiocontrast studies described in Contrib. Embryol., 38:59-70 (1966) revealed that maternal arterial blood is propelled through patent arteries toward the chorionic plate and disperses laterally through a complex system of vascular lacunae within the intervillous space that contains arterial, venous and capillary-like zones. In two clinical conditions associated with fetal and placental hypoxia and vascular insufficiency, i.e. preeclampsia and IVGR, the number of patent spiral arteries is reduced (*Am. J. Obstet. GynecoL*, 155: 401-12 (1986). Pathological changes in this vasculature extend from the intervillous space to the base of the spiral arteries and may be due to the failure of normal angiogenic development.

The precise regulation of angiogenic factors expressed at the deciduoplacental interface is unknown currently but bFGF, VEGF (*Biol. Reprod.*, 51:524-30 (1994)) and other angiogenic proteins have been identified in human placenta. Clinical conditions associated with excessive trophoblastic invasion and neovascularity (e.g., placenta accreta, increta, precreta and choriocarcinoma), therefore, may be due to inadequate restraint by antiangiogenic agents. Conversely, premature or excessive production of antiangiogenic proteins relative to angiogenic factors could lead to poor maternal vascularization of the placental bed and result in fetoplacental ischemia as observed in preeclampsia and IUGR (*Clin. Perinatol.*, 18: 661-82 (1994)). Based on the current findings, antiangiogenic peptides of the invention seem also to play a critical role in the human placenta, serving to regulate placental vascularization during normal pregnancy.

Recent reports have documented the expression of three angiogenic factors during early human placental development. VEGF is synthesized by human endometrium during the preimplantation phase (J. Clin. Endocrinol. Metab., 81: 3112-18 (1996)), in the maternal decidua (Growth Factors, 12:235-43 (1995)) and by fetal trophoblast cells (Biol. Reprod., 51:524-30 (1994)). Platelet-derived endothelial cell growth factor (PDEGF) is expressed in secretory endometrium, and decidua (Human Reprod., 10:989-93 (1995)). Basic FGF is synthesized in endometrium and a preliminary report that bFGF is expressed throughout human placental development published in Endocrine Society Meeting, Abstract R35-4 (1997), confirms the current findings.

Normal placental neovascularization is most probably controlled by the co-regulation of angiogenic and antiangiogenic factors. Dysregulations of the balance between these factors leads to hypovascularized placental conditions and subsequent pregnancy pathology. Three proteins expressed at the human placental-decidual interface would typically be candidates for antiangiogenic factors. Without being limited to any one theory, these are genetically related lactogenic proteins. These genes all encode primary protein products of about 20-25K. As documented above, however, these about 20-25K proteins possess no antiangiogenic activity. Each of these proteins, nevertheless, possesses peptidase recognition sequences that predict the possibility of their cleavage to 16K N-terminal fragments which have been now found to have antiangiogenic activity.

The following experiments were undertaken to test the hypothesis that 16K hPRL, 16K hPL and 16K hGH-V fragments of the lactogenic hormone family are spontaneously produced and play a physiological role in the vascular development of the human placenta.

A. Cathepsin D Cleavage of hPRL

The first question in developing the diagnostic assay was to determine whether full length hPRL could be enzymatically cleaved to generate a biologically active 16K fragment. Cathepsin-like enzymes, which have been shown to cleave rat PRL to the 16K isoform (*Endocrinology*, 133:935-38 (1993)), e.g., cathepsin D, are expressed in several cells and tissues at the maternal-fetal interface. As shown herein, this enzyme can cleave human decidual PRL and can generate bioactive antiangiogenic fragments of purified hPRL.

Purified, intact full length 23K pituitary hPRL (30 µg) was incubated at 37° C. in glycine-HCl buffer (pH 3.5) with human cathepsin D (0.3 μg). Aliquots of the incubation mix were taken at 0, 10, 20, 30, 60, 120 minutes and 24 hours. Samples were reduced with 5% β-mercaptoethanol, electrophoresed on 13.5% SDS-polyacrylamide gels and silver stained.

Under these conditions, pituitary hPRL was cleaved by cathepsin D, generating several peptides, as seen in FIG. 6. The major fragment had an apparent molecular mass of about 13K with aminor fragment of about 18K. Under the same conditions, rat prolactin (rPRL) was cleaved into two major peptides of 16K and 8K as described previously (*Endocrinology,* 133:935-38 (1993)).

Next, a study was performed to confirm that human amniotic fluid prolactin, derived from the adjacent decidua, could be cleaved by endogenous protease(s) under acidic conditions to yield hPRL fragments identical to those generated by cathepsin D digestion in vitro, i.e. 13K, 18K or 16K.

Midtrimester amniotic fluid samples from 6 different subjects were adjusted to different pH ranging from 7.4 to 3.5, and incubated at 37° C. for 24 hours. Western blotting with anti-prolactin antibody revealed immunoreactive bands representing undigested 23K PRL at pH 7.4, but when incubated under acidic conditions, two fragments of 18K and 13K were observed, as seen in FIG. 7. The similarity of this pattern with that generated by cathepsin D digestion suggested that endogenous cathepsin D might be responsible for this observation. Data indicate that endogenous PRL in late first trimester human decidual cytosol also can be cleaved by exogenous cathepsin D. Western blotting of non-reducing gels indicated that endogenous decidual thiol reductase(s) reduce the 18K and 13K fragments under these conditions.

The pH optimum of hPRL cleavage by cathepsin D was then examined in more detail. Human PRL was cleaved in vitro by cathepsin D at pH 7.4, 5.5 and 3.5, reduced with β-mercaptoethanol and tested for antiangiogenic activity on BBCE cells bFGF-induced mitogenesis of BBCE cells was inhibited 50% by hPRL cleaved at pH 7.4 and 100% by hPRL cleaved at pH 5.5 and 3.5. Intact full length hPRL has no effect on cell growth. Thus, while less efficient than under acidic conditions, cathepsin D at physiological pH can generate bioactive, antiangiogenic fragments of hPRL.

B. Mapping of Cathepsin D Cleavage Site

To identify the cathepsin D cleavage site, recombinant 23K hPRL was treated as before with cathepsin D and the fragments resulting from the digestion were separated from intact PRL by gel filtration using a BioRad Biogel P-30 packed column. The column was equilibrated in 0.1 M ammonium bicarbonate buffer containing 200 mM β-mercaptoethanol (Endocrinology, 122:2892-98 (1988)). The PRL fragments were examined by SDS-PAGE using silver staining and revealed 18K and 16K species. The hPRL fragments were purified on a C18 reverse phase column. The fragments were reduced, loaded onto the column at pH=3.0 using 1% (v/v) TFA, and diluted using a gradient of acetonitrile containing 0.1% TFA. The purified fragments were separated on 13.5% SDS-PAGE gels and transferred to polyvinyldene fluoride membranes in 10 mM CAPS (3-cyclohexylamino-1-propanesulfonic acid) buffer hP=11.0 with 10% methanol. Transferred protein was stained with 0.1% Coomassie blue, the two bands of interest, namely 18K and 13K, excised from the PVDF membrane and the peptides were sequenced directly on a gas phase Beckman-Porton PI2090 protein sequencer by Edman degradation sequencing to analyze the $NH_2$-termini of the cleaved fragments.

As in the case of rat PRL where cleavage occurs at two sites, two cathepsin D cleavage sites between amino acids 36/37 and 133/134 of the mature hPRL were found. These sites resulted in two fragments, hPRL fragment 1-133 and hPRL fragment 37-133, consistent with the 18K and 13K bands identified in the corresponding Western blots of cleaved hPRL.

C. Biological Activity of Cathepsin D Cleaved hPRL

Separating the 18K and 13K fragments generated by cathepsin D cleavage of hPRL by HPLC was not successful, and both were eluted in fraction 6 seen in FIG. 8A. Each of the HPLC fractions was assayed for their ability to inhibit bFGF-induced BBCE cell ($^3$H) thymidine incorporation. Only fraction 6, containing the 18K and 13K fragments, inhibited the mitogenic response to exogenous bFGF, as seen in FIG. 8B. Thus the mixture of the unseparated 18K and 13K PRL was responsible for the observed antiangiogenic activity.

D. Identification of Cathepsin D at the Human Deciduoplacental Interface

To establish the present of human cathepsin D mRNA in human placental and decidual tissue oligonucleotide primers that span exon 8 and 9 based on the human cathepsin D gene sequence (DNA Cell Biol., 10:423-31 (1991)) were prepared. Total mRNA from these tissues was reverse transcribed and amplified using methods according to *J. Clin. Endocrine Metab.* 78:642-649 (1994). The results indicate that human placenta, endometrium and human umbilical vein endothelial cells all express cathepsin D mRNA transcripts (data not shown). Human fetal liver was used as a positive control. These results were extended by Western blotting of tissue lysates and biological fluids from pregnant and nonpregnant women. In reducing SDS-PAGE, anti-human cathepsin D antiserum detected the two subunits, about 25K and about 22K protein, in amniotic fluid, pregnancy plasma, and placental and decidual lysates. Nonpregnant endometrial lysates also contained cathepsin D protein.

E. Identification of Cathepsin D by Immunohistochemistry

Human fetal membranes and underlying decidua at term were evaluated by immunohistochemistry (IHC) using an antibody to human cathepsin D. Cathepsin D positive cells were observed in the amniotic membrane, chorionic trophoblast cells and scattered cells within the decidua. In human pregnancy the decidua synthesizes and secretes intact 23K hPRL into the extracellular space and the amniotic cavity. It has been confirmed that at least one enzyme capable of cleaving 23K PRL into antiangiogenic 16K fragments, cathepsin D, is not only synthesized locally at the deciduoplacental interface but also is present in amniotic fluid, plasma and in fact is synthesized by human endothelial cells. Thus, the necessary molecular components required to generate 16K PRL are available at the site of placental vascularization. The activity level of cathepsin D and/or concentrations of 16K fragments of hPRL, hPL and hGH-V are thus advantageously utilized for detection of placental function, whether normal or abnormal. Besides the cathepsin D site in hPRL several other cleavage sites exist within the sequences of hGH, hGH-V and hPL that generate a N-terminal fragment of around 16 kDa. hGH can be cleaved by plasmin, thrombin and subtilisin (*EMBO J,* 2:493 (1983)). The consensus cleavage sequence for these enzymes is also present in hGH-V and we have shown herein that hGH-V is cleaved by thrombin. Furthermore, preeclampsia has been characterized as a disease of an excess in thrombin activity. Finally, hPL can be cleaved by plasmin to yield a 16K N-terminal fragment (*J. Biol. Chem.* 254:2296 (1979)).

F. 16K hPRL Binding Sites are Present in Human Placenta Increases throughout Pregnancy A novel, high affinity (Kd=1 nM) receptor for rat 16K PRL (16K rPRL) was described in capillary endothelial cells by radioligand binding studies with $^{125}$I-16K rPRL (*Endocrinology*, 130: 1380 (1992)). Utilizing this approach we measured specific 16K hPRL binding sites in human placental membrane fractions obtained at different stages of gestation. By Scatchard analysis the dissociation constants were not significantly different in first, second or third trimester placental membranes. However, the maximal binding (Bmax) for membranes obtained during the first trimester was only 3.19 fmol/µg protein, whereas the Bmax for the second trimester was 630 fmol/µg protein and 775 fmol/µg protein for the third trimester. These differences were confirmed by measurement of specific binding in multiple samples (FIG. 9). Membranes from first trimester placentas (n=4) had maximal specific binding of 357±142.7 cpm/5 µg protein, while membranes from second (n=3) had 1778±128 cpm/5 µg protein and third trimester (n=3) had 4041±1882 cpm/5 µg protein. These results support the hypothesis that 16K hPRL may play a role in the inhibition of angiogenesis following completion of the deciduoplacental interface. The absence of receptors early in pregnancy is consistent with the idea that the action of an antiangiogenic factor would be inappropriate in early development and lead to inhibition of the normal vascular connection. Overproduction of this antiangiogenic factor could be involved in disorders of pregnancy in which formation of the vascular connection of the placenta is compromised, e.g., preeclampsia.

Specimens of human placental tissues of first, second, and third trimester pregnancies were obtained from consenting women either undergoing elective pregnancy terminations (first and second trimester) or at the end of pregnancy (third trimester). The protocols were approved by the UCSF committee of human research. Tissues were kept at −80° C. until further processing. Rinsed tissues were homogenized in 1:1 volume of 20 mM Tris, pH 7.4, 250 mM sucrose, 2 mM EDTA, and 0.2 mM Pefablock and centrifuged at 10,000 g for 30 min. The pellet-was resuspended in 5 ml of buffer and recentrifuged at 10,000 g for 30 min. Both supernatants were brought to 100 mM NaCl and 0.2 mM $MgCl_2$ to precipitate microsomal membranes. The pellet from a subsequent centrifugation at 30,000 g for 45 min was resuspended in 20 mM Hepes, 10% glycerol, 1 mM EDTA, 1 mM Pefablock, and 0.141U of aprotinin.

5 µg of the above membrane preparation were incubated with 100 pM of $^{125}$I-16K rPRL with or without 400 nM of 16K hPRL in a final volume of 300 µl of assay buffer (100 mM Tris, 500 mM acetic acid, 10 MM $MgCl_2$, 0.1% BSA, pH 7.4) for 5 h at room temperature. Assays were terminated by dilution with 3 ml cold assay buffer, followed by centrifugation at 3000 rpm for 45 min. at 4° C. and aspiration of supernantants. Specific binding was determined by subtracting counts bound in the presence of an excess (400 nM) of unlabeled 16K hPRL from counts bound in the absence of unlabeled hormone.

EXAMPLE 3

General Procedure for the Production of Peptides

This example illustrates the general methods used for the production of peptides of the invention.

Intact full length human prolactin (hPRL), human growth hormone (hGH), human growth hormone variant (hGH-V), human placental lactogen (hPL) and 16K N-terminal fragment of human prolactin (16K hPRL), growth hormone (16K hGH), growth hormone variant (16K hGH-V) and placental lactogen (16K hPL) were produced as described below.

The coding sequences, antisense sequences, and amino acid sequences of the intact hormones and 16K N-terminal peptides are listed in sequences identified as SEQ ID NO:1-30 as follows.

```
hPRL (Met⁻¹Cys¹⁹⁹)
                                                         (SEQ ID NO:1)
ATGTTGCCCA TCTGTCCCGG CGGGGCTGCC CGATGCCAGG TGACCCTTCG AGACCTGTTT   60

GACCGCGCCG TCGTCCTGTC CCACTACATC CATAACCTCT CCTCAGAAAT GTTCAGCGAA  120

TTCGATAAAC GGTATACCCA TGGCCGGGGG TTCATTACCA AGGCCATCAA CAGCTGCCAC  180

ACTTCTTCCC TTGCCACCCC CGAAGACAAG GAGCAAGCCC AACAGATGAA TCAAAAAGAC  240

TTTCTGAGCC TGATAGTCAG CATATTGCGA TCCTGGAATG AGCCTCTGTA TCATCTGGTC  300

ACGGAAGTAC GTGGTATGCA AGAAGCCCCG GAGGCTATCC TATCCAAAGC TGTAGAGATT  360

GAGGAGCAAA CCAAACGGCT TCTAGAGGGC ATGGAGCTGA TAGTCAGCCA GGTTCATCCT  420

GAAACCAAAG AAAATGAGAT CTACCCTGTC TGGTCGGGAC TTCCATCCCT GCAGATGGCT  480

GATGAAGAGT CTCGCCTTTC TGCTTATTAT AACCTGCTCC ACTGCCTACG CAGGGATTCA  540

CATAAAATCG ACAATTATCT CAAGCTCCTG AAGTGCCGAA TCATCCACAA CAACAACTGC  600

TAA;

16K hPRL (Met⁻¹Thr¹²³)
                                                         (SEQ ID NO:2)
ATGTTGCCCA TCTGTCCCGG CGGGGCTGCC CGATGCCAGG TGACCCTTCG AGACCTGTTT   60

GACCGCGCCG TCGTCCTGTC CCACTACATC CATAACCTCT CCTCAGAAAT GTTCAGCGAA  120

TTCGATAAAC GGTATACCCA TGGCCGGGGG TTCATTACCA AGGCCATCAA CAGCTCCCAC  180
```

-continued

```
ACTTCTTCCC TTGCCACCCC CGAAGACAAG GAGCAAGCCC AACAGATGAA TCAAAAAGAC      240

TTTCTGAGCC TGATAGTCAG CATATTGCGA TCCTGGAATG AGCCTCTGTA TCATCTGGTC      300

ACGGAAGTAC GTGGTATGCA AGAAGCCCCG GAGGCTATCC TATCCAAAGC TGTAGAGATT      360

GAGGAGCAAA CCTAA;
```

16K hPRL (Met$^{-1}$Pro$^{139}$)

(SEQ ID NO:3)
```
ATGTTGCCCA TCTGTCCCGG CGGGGCTGCC CGATGCCAGG TGACCCTTCG AGACCTGTTT       60

GACCGCGCCG TCGTCCTGTC CCACTACATC CATAACCTCT CCTCAGAAAT GTTCAGCGAA      120

TTCGATAAAC GGTATACCCA TGGCCGGGGG TTCATTACCA AGGCCATCAA CAGCTCCCAC      180

ACTTCTTCCC TTGCCACCCC CGAAGACAAG GAGCAAGCCC AAGAGATGAA TCAAAAAGAC      240

TTTCTGAGCC TGATAGTCAG CATATTGCGA TCCTGGAATG AGCCTCTGTA TCATCTGGTC      300

ACGGAAGTAC GTGGTATGCA AGAAGCCCCG GAGGCTATCC TATCCAAAGC TGTAGAGATT      360

GAGGAGCAAA CCAAACGGCT TCTAGAGGGC ATGGAGCTGA TAGTCAGCCA GGTTCATCCT      420

TGA;
```

16K hPRL (Met$^{-1}$Pro$^{142}$)

(SEQ ID NO:4)
```
ATGTTGCCCA TCTGTCCCGG CGGGGCTGCC CGATGCCAGG TGACCCTTCG               50

AGACCTGTTT GACCGCGCCG TCGTCCTGTC CCACTACATC CATAACCTCT              100

CCTCAGAAAT GTTCAGCGAA TTCGATAAAC GGTATACCCA TGGCCGGGGG              150

TTCATTACCA AGGCCATCAA CAGCTCCCAC ACTTCTTCCC TTGCCACCCC              200

CGAAGACAAG GAGCAAGCCC AACAGATGAA TCAAAAAGAC TTTCTGAGCC              250

TGATAGTCAG CATATTGCGA TCCTGGAATG AGCCTCTGTA TCATCTGGTC              300

ACGGAAGTAC GTGGTATGCA AGAAGCCCCG GAGGCTATCC TATCCAAAGC              350

TGTAGAGATT GAGGAGCAAA CCAAACGGCT TCTAGAGGGC ATGGAGCTGA              400

TAGTCAGCCA GGTTCATCCT AGACCCCCAA CACCTGAGAT CTACCCTGTC              450

TGGTCGGGAC TTCCATCCCT GCAGATGGCT GATGAAGAGT CTCGCCTTTC              500

TGCTTATTAT AACCTGCTCC ACTGCCTACG CAGGGATTCA CATAAAATCG              550

ACAATTATCT CAAGCTCCTG AAGTGCCGAA TCATCCACAA CAACAACTGC              600

TAA;
``` hPRL (Met$^{-1}$Cys$^{199}$) antisense (SEQ ID NO:5)
```
TACAACGGGT AGACAGGGCC GCCCCGACGG GCTACGGTCC ACTGGGAAGC TCTGGACAAA       60

CTGGCGCGGC AGCAGGACAG GGTGATGTAG GTATTGGAGA GGAGTCTTTA CAAGTCGCTT      120

AAGCTATTTG CCATATGGGT ACCGGCCCCC AAGTAATGGT TCCGGTAGTT GTCGACGGTG      180

TGAAGAAGGG AACGGTGGGG GCTTCTGTTC CTCGTTCGGG TTGTCTACTT AGTTTTTCTG      240

AAAGACTCGG ACTATCAGTC GTATAACGCT AGGACCTTAC TCGGAGACAT AGTAGACCAG      300

TGCCTTCATG CACCATACGT TCTTCGGGGC CTCCGATAGG ATAGGTTTCG ACATCTCTAA      360

CTCCTCGTTT GGTTTGCCGA AGATCTCCCG TACCTCGACT ATCAGTCGGT CCAAGTAGGA      420

CTTTGGTTTC TTTTACTCTA GATGGGACAG ACCAGCCCTG AAGGTAGGGA CGTCTACCGA      480

CTACTTCTCA GAGCGGAAAG ACGAATAATA TTGGACGAGG TGACGGATGC GTCCCTAAGT      540

GTATTTTAGC TGTTAATAGA GTTCGAGGAC TTCACGGCTT AGTAGGTGTT GTTGTTGACG      600

ATT;
```

16K hPRL (Met$^{-1}$Thr$^{123}$) antisense

-continued 16K hPRL (Met⁻¹Pro¹³⁹)
(SEQ ID NO:6)
```
TACAACGGGT AGACAGGGCC GCCCCGACGG GCTACGGTCC ACTGGGAAGC TCTGGACAAA   60

CTGGCGCGGC AGCAGGACAG GGTGATGTAG GTATTGGAGA GGAGTCTTTA CAAGTCGCTT  120

AAGCTATTTG CCATATGGGT ACCGGCCCCC AAGTAATGGT TCCGGTAGTT GTCGAGGGTG  180

TGAAGAAGGG AACGGTGGGG GCTTCTGTTC CTCGTTCGGG TTGTCTACTT AGTTTTTCTG  240

AAAGACTCGG ACTATCAGTC GTATAACGCT AGGACCTTAC TCGGAGACAT AGTAGACCAG  300

TGCCTTCATG CACCATACGT TCTTCGGGGC CTCCGATAGG ATAGGTTTCG ACATCTCTAA  360

CTCCTCGTTT GGATT;
```

16K hPRL (Met⁻¹Pro¹³⁹) antisense
(SEQ ID NO:7)
```
TACAACGGGT AGACAGGGCC GCCCCGACGG GCTACGGTCC ACTGGGAAGC TCTGGACAAA   60

CTGGCGCGGC AGCAGGACAG GGTGATGTAG GTATTGGAGA GGAGTCTTTA CAAGTCGCTT  120

AAGCTATTTG CCATATGGGT ACCGGCCCCC AAGTAATGGT TCCGGTAGTT GTCGAGGGTG  180

TGAAGAAGGG AACGGTGGGG GCTTCTGTTC CTCGTTCGGG TTGTCTACTT AGTTTTTCTG  240

AAAGACTCGG ACTATCAGTC GTATAACGCT AGGACCTTAC TCGGAGACAT AGTAGACCAG  300

TGCCTTCATG CACCATACGT TCTTCGGGGC CTCCGATAGG ATAGGTTTCG ACATCTCTAA  360

CTCCTCGTTT GGTTTGCCGA AGATCTCCCG TACCTCGACT ATCAGTCGGT CCAAGTAGGA  420

ACT;
```

16K hPRL (Met⁻¹Pro¹⁴²)
(SEQ ID NO:8)
```
TACAACGGGT AGACAGGGCC GCCCCGACGG GCTACGGTCC ACTGGGAAGC             50

TCTGGACAAA CTGGCGCGGC AGCAGGACAG GGTGATGTAG GTATTGGAGA            100

GGAGTCTTTA CAAGTCGCTT AAGCTATTTG CCATATGGGT ACCGGCCCCC            150

AAGTAATGGT TCCGGTAGTT GTCGAGGGTG TGAAGAAGGG AACGGTGGGG            200

GCTTCTGTTC CTCGTTCGGG TTGTCTACTT AGTTTTTCTG AAAGACTCGG            250

ACTATCAGTC GTATAACGCT AGGACCTTAC TCGGAGACAT AGTAGACCAG            300

TGCCTTCATG CACCATACGT TCTTCGGGGC CTCCGATAGG ATAGGTTTCG            350

ACATCTCTAA CTCCTCGTTT GGTTTGCCGA AGATCTCCCG TACCTCGACT            400

ATCAGTCGGT CCAAGTAGGA TCTGGGGGTT GTGGACTCTA GATGGGACAG            450

ACCAGCCCTG AAGGTAGGGA CGTCTACCGA CTACTTCTCA GAGCGGAAAG            500

ACGAATAATA TTGGACGAGG TGACGGATGC GTCCCTAAGT GTATTTTAGC            550

TGTTAATAGA GTTCGAGGAC TTCACGGCTT AGTAGGTGTT GTTGTTGACG            600

ATT;
``` hPRL (Met⁻¹Cys¹⁹⁹)
(SEQ ID NO:9)
```
MetLeuProIleCysProGlyGlyAlaAlaArgCysGlnValThrLeuArgAspLeuPhe
 -1              5             10             15

AspArgAlaValValLeuSerHisTyrIleHisAsnLeuSerSerGluMetPheSerGlu
 20             25             30             35

PheAspLysArgTyrThrHisGlyArgGlyPheIleThrLysAlaIleAsnSerCysHis
 40             45             50             55

ThrSerSerLeuAlaThrProGluAspLysGluGlnAlaGlnGlnMetAsnGlnLysAsp
 60             65             70             75

PheLeuSerLeuIleValSerIleLeuArgSerTrpAsnGluProLeuTyrHisLeuVal
 80             85             90             95

ThrGluValArgGlyMetGlnGluAlaProGluAlaIleLeuSerLysAlaValGluIle
100            105            110            115
```

-continued

GluGluGlnThrLysArgLeuLeuGluGlyMetGluLeuIleValSerGlnValHisPro
120            125            130            135

GluThrLysGluAsnGluIleTyrProValTrpSerGlyLeuProSerLeuGlnMetAla
140            145            150            155

AspGluGluSerArgLeuSerAlaTyrTyrAsnLeuLeuHisCysLeuArgArgAspSer
160            165            170            175

HisLysIleAspAsnTyrLeuLysLeuLeuLysCysArgIleIleHisAsnAsnAsnCys
180            185            190            195            199

16K hPRL (Met⁻¹Thr¹²³)
(SEQ ID NO:10)
MetLeuProIleCysProGlyGlyAlaAlaArgCysGlnValThrLeuArgAspLeuPhe
-1             5              10             15

AspArgAlaValValLeuSerHisTyrIleHisAsnLeuSerSerGluMetPheSerGlu
20             25             30             35

PheAspLysArgTyrThrHisGlyArgGlyPheIleThrLysAlaIleAsnSerSerHis
40             45             50             55

ThrSerSerLeuAlaThrProGluAspLysGluGlnAlaGlnGlnMetAsnGlnLysAsp
60             65             70             75

PheLeuSerLeuIleValSerIleLeuArgSerTrpAsnGluProLeuTyrHisLeuVal
80             85             90             95

ThrGluValArgGlyMetGlnGluAlaProGluAlaIleLeuSerLysAlaValGluIle
100            105            110            115

GluGluGlnThr;
120            123

16K hPRL (Met⁻¹Pro¹³⁹)
(SEQ ID NO:11)
MetLeuProIleCysProGlyGlyAlaAlaArgCysGlnValThrLeuArgAspLeuPhe
-1             5              10             15

AspArgAlaValValLeuSerHisTyrIleHisAsnLeuSerSerGluMetPheSerGlu
20             25             30             35

PheAspLysArgTyrThrHisGlyArgGlyPheIleThrLysAlaIleAsnSerSerHis
40             45             50             55

ThrSerSerLeuAlaThrProGluAspLysGluGlnAlaGlnGlnMetAsnGlnLysAsp
60             65             70             75

PheLeuSerLeuIleValSerIleLeuArgSerTrpAsnGluProLeuTyrHisLeuVal
80             85             90             95

ThrGluValArgGlyMetGlnGluAlaProGluAlaIleLeuSerLysAlaValGluIle
100            105            110            115

GluGluGlnThrLysArgLeuLeuGluGlyMetGluLeuIleValSerGlnValHisPro;
120            125            130            135            139

16K hPRL (Met⁻¹Pro¹⁴²)
(SEQ ID NO:12)
MetLeuProIleCysProGlyGlyAlaAlaArgCysGlnValThrLeuArgAspLeuPhe
-1             5              10             15

AspArgAlaValValLeuSerHisTyrIleHisAsnLeuSerSerGluMetPheSerGlu
20             25             30             35

PheAspLysArgTyrThrHisGlyArgGlyPheIleThrLysAlaIleAsnSerSerHis
40             45             50             55

ThrSerSerLeuAlaThrProGluAspLysGluGlnAlaGlnGlnMetAsnGlnLysAsp
60             65             70             75

PheLeuSerLeuIleValSerIleLeuArgSerTrpAsnGluProLeuTyrHisLeuVal
80             85             90             95

ThrGluValArgGlyMetGlnGluAlaProGluAlaIleLeuSerLysAlaValGluIle
100            105            110            115

GluGluGlnThrLysArgLeuLeuGluGlyMetGluLeuIleValSerGlnValHisPro

-continued

```
120             125             130             135
ArgProPro;
140  142
``` hRL (Met⁻¹Phe¹⁹¹)

(SEQ ID NO:13)
```
ATGGTCCAAA CCGTTCCGTT ATCCAGGCTT TTTGACCACG CTATGCTCCA AGCCCATCGC  60
GCGCACCAGC TGGCCATTGA CACCTACCAG GAGTTTGAAG AAACCTATAT CCCAAAGGAC  120
CAGAAGTATT CGTTCCTGCA TGACTCCCAG ACCTCCTTCT GCTTCTCAGA CTCTATTCCG  180
ACACCCTCCA ACATGGAGGA AACGCAACAG AAATCCAATC TAGAGCTGCT CCGCATCTCC  240
CTGCTGCTCA TCGAGTCGTG GCTGGAGCCC GTGCGGTTCC TCAGGAGTAT GTTCGCCAAC  300
AACCTGGTGT ATGACACCTC GGACAGCGAT GACTATACC TCCTAAAGGA CCTAGAGGAA  360
GGCATCCAAA CGCTGATGGG GAGGCTGGAA GACGGCAGCC GCCGGACTGG GCAGATCCTC  420
AAGCAGACCT ACAGCAAGTT TGACACAAAC TCGCACAACC ATGACGCACT GCTCAAGAAC  480
TACGGGCTGC TCTACTGCTT CAGGAAGGAC ATGGACAAGG TCGAGACATT CCTGCGCATG  540
TGCAGTGCC GCTCTGTGGA GGGCAGCTGT GGCTTCTAG; 579
```

16K hPL (Met⁻¹Arg¹³⁴)

(SEQ ID NO:14)
```
ATGGTCCAAA CCGTTCCGTT ATCCAGGCTT TTTGACCACG CTATGCTCCA            50
AGCCCATCGC GCGCACCAGC TGGCCATTGA CACCTACCAG GAGTTTGAAG            100
AAACCTATAT CCCAAAGGAC CAGAAGTATT CGTTCCTGCA TGACTCCCAG            150
ACCTCCTTCT CTTTCTCAGA CTCTATTCCG ACACCCTCCA ACATGGAGGA            200
AACGCAACAG AAATCCAATC TAGAGCTGCT CCGCATCTCC CTGCTGCTCA            250
TCGAGTCGTG GCTGGAGCCC GTGCGGTTCC TCAGGAGTAT GTTCGCCAAC            300
AACCTGGTGT ATGACACCTC GGACAGCGAT GACTATACC TCCTAAAGGA             350
CCTAGAGGAA GGCATCCAAA CGCTGATGGG GAGGCTGGAA GACGGCAGCC            400
CCCGGACTGG GCAGATCCTC AAGCAGACCT ACAGCAAGTT TGACACAAAC            450
TCGCACAACC ATGACGCACT GCTCAAGAAC TACGGGCTGC TCTACTGCTT            500
CAGGAAGGAC ATGGACAAGG TCGAGACATT CCTGCGCATG GTGCAGTGCC            550
GCTCTGTGGA GGGCAGCTGT GGCTTCTAG;
``` hPL (Met⁻¹Phe¹⁹¹) antisense (SEQ ID NO:15)
```
TACCAGGTTT GGCAAGGCAA TAGGTCCGAA AAACTGGTGC GATACGAGGT TCGGGTAGCG  60
CGCGTGGTCG ACCGGTAACT GTGGATGGTC CTCAAACTTC TTTGGATATA GGGTTTCCTG  120
GTCTTCATAA GCAAGGACGT ACTGAGGGTC TGGAGGAAGA CGAAGAGTCT GAGATAAGGC  180
TGTGGGAGGT TGTACCTCCT TTGCGTTGTC TTTAGGTTAG ATCTCGACGA GGCGTAGAGG  240
GACGACGAGT AGCTCAGCAC CGACCTCGGG CACGCCAAGG AGTCCTCATA CAAGCGGTGG  300
TTGGACCACA TACTGTGGAG CCTGTCGCTA CTGATAGTGG AGGATTTCCT GGATCTCCTT  360
CCGTAGGTTT GCGACTACCC CTCCGACCTT CTGCCGTCGG CGGCCTGACC CGTCTAGGAG  420
TTCGTCTGGA TGTCGTTCAA ACTGTGTTTG AGCGTGTTGG TACTGCGTGA CGAGTTCTTG  480
ATGCCCGACG AGATGACGAA GTCCTTCCTG TACCTGTTCC AGCTCTGTAA GGACGCGTAC  540
CACGTCACGG CGAGACACCT CCCGTCGACA CCGAAGATC;
```

16K hPL (Met⁻¹Arg¹³⁴) antisense (SEQ ID NO:16)
```
TACCAGGTTT GGCAAGGCAA TAGGTCCGAA AAACTGGTGC GATACGAGGT            50
TCGGGTAGCG CGCGTGGTCG ACCGGTAACT GTGGATGGTC CTCAAACTTC            100
```

-continued

```
TTTGGATATA GGGTTTCCTG GTCTTCATAA GCAAGGACGT ACTGAGGGTC        150

TGGAGGAAGA GAAAGAGTCT GAGATAAGGC TGTGGGAGGT TGTACCTCCT        200

TTGCGTTGTC TTTAGGTTAG ATCTCGACGA GGCGTAGAGG GACGACGAGT        250

AGCTCAGCAC CGACCTCGGG CACGCCAAGG AGTCCTCATA CAAGCGGTTG        300

TTGGACCACA TACTGTGGAG CCTGTCGCTA CTGATAGTGG AGGATTTCCT        350

GGATCTCCTT CCGTAGGTTT GCGACTACCC CTCCGACCTT CTGCCGTCGG        400

GGGCCTGACC CGTCTAGGAG TTCGTCTGGA TGTCGTTCAA ACTGTGTTTG        450

AGCGTGTTGG TACTGCGTGA CGAGTTCTTG ATGCCCGACG AGATGACGAA        500

GTCCTTCCTG TACCTGTTCC AGCTCTGTAA GGACGCGTAC CACGTCACGG        550

CGAGACACCT CCCGTCGACA CCGAAGATC;
``` hPL (Met⁻¹Phe¹⁹¹)
(SEQ ID NO:17)

```
MetValGlnThrValProLeuSerArgLeuPheAspHisAlaMetLeuGlnAlaHisArg
 -1               5                10               15

AlaHisGlnLeuAlaIleAspThrTyrGlrlGluPheGluGlumrTyrIleProLysAsp
 20              25                30               35

GlnLysTyrSerPheLeuHisAspSerGlnThrSerPheCysPheSerAspSerIlePro
 40              45                50               55

ThrProSerAsnMetGluGluThrGlnGlnLysSerAsnLeuGluLeuLeuArgIleSer
 60              65                70               75

LeuLeuLeuIleGluSerTrpLeuGluProValArgPheLeuArgSerMetPheAlaAsn
 80              85                90               95

AsnLeuValTyrAspThrSerAspSerAspAspTyrHisLeuLeuLysAspLeuGluGlu
 100             100               110              115

GlyIleGlnThrLeuMetGlyArgLeuGluAspGlySerArgArgThrGlyGlnIleLeu
 120             125               130              135

LysGlnThrTyrSerLysPheAspThrAsnSerHisAsnHisAspAlaLeuLeuLysAsn
 140             145               150              155

TyrGlyLeuLeuTyrCysPheArgLysAspMetAspLysValGluThrPheLeuArgMet
 160             165               170              175

ValGlnCysArgSerValGluGlySerCysGlyPhe;
 180             185               190
```

16K hPL (Met⁻¹Arg¹³¹)
(SEQ ID NO:18)

```
MetValGlnThrValProLeuSerArgLeuPheAspHisAlaMetLeuGlnAlaHisArg
 -1               5                10               15

AlaHisGlnLeuAlaIleAspThrTyrGlnGluPheGluGluThrTyrIleProLysAsp
 20              25                30               35

GlnLysTyrSerPheLeuHisAspSerGlnThrSerPheSerPheSerAspSerIlePro
 40              45                50               55

ThrProSerAsnMetGluGluThrGlnGlnLysSerAsnLeuGluLeuLeuArgIleSer
 60              65                70               75

LeuLeuLeuIleGluSerTrpLeuGluProValArgPheLeuArgSerMetPheAlaAsn
 80              85                90               95

AsnLeuValTyrAspThrSerAspSerAspAspTyrHisLeuLeuLysAspLeuGluGlu
 100             105               110              115

GlyIleGlnThrLeuMetGlyArgLeuGluAspGlySerProArg;
 120             125               130
``` hGH (Met⁻¹Phe¹⁹¹)
(SEQ ID NO:19)

```
ATGTTCCCAA CCATTCCCTT ATCCAGGCTT TTTGACAACG CTATGCTCCG         50
```

-continued

```
CGCCCATCGT CTGCACCAGC TGGCCTTTGA CACCTACCAG GAGTTTGAAG           100

AAGCCTATAT CCCAAAGGAA CAGAAGTATT CATTCCTGCA GAACCCCCAG           150

ACCTCCCTCT GTTTCTCAGA GTCTATTCCG ACACCCTCCA ACAGGGAGGA           200

AACACAACAG AAATCCAACC TAGAGCTGCT CCGCATCTCC CTGCTGCTCA           250

TCCAGTCGTG GCTGGAGCCC GTGCAGTTCC TCAGGAGTGT CTTCGCCAAC           300

AGCCTGGTGT ACGGCGCCTC TGACAGCAAC GTCTATGACC TCCTAAAGGA           350

CCTAGAGGAA GGCATCCAAA CGCTGATGGG GAGGCTGGAA GATGGCAGCC           400

CCCGGACTGG GCAGATCTTC AAGCAGACCT ACAGCAAGTT CGACACAAAC           450

TCACACAACG ATGACGCACT ACTCAAGAAC TACGGGCTGC TCTACTGCTT           500

CAGGAAGGAC ATGGACAAGG TCGAGACATT CCTGCGCATC GTGCAGTGCC           550

GCTCTGTGGA GGGCAGCTGT GGCTTCTAG;
```

16K hGH (Met$^{-1}$Pro$^{133}$)
(SEQ ID NO:20)

```
ATGTTCCCAA CCATTCCCTT ATCCAGGCTT TTTGACAACG CTATGCTCCG            50

CGCCCATCGT CTGCACCAGC TGGCCTTTGA CACCTACCAG GAGTTTGAAG           100

AAGCCTATAT CCCAAAGGAA CAGAAGTATT CATTCCTGCA GAACCCCCAG           150

ACCTCCCTCT CTTTCTCAGA GTCTATTCCG ACACCCTCCA ACAGGGAGGA           200

AACACAACAG AAATCCAACC TAGAGCTGCT CCGCATCTCC CTGCTGCTCA           250

TCCAGTCGTG GCTGGAGCCC GTGCAGTTCC TCAGGAGTGT CTTCGCCAAC           300

AGCCTGGTGT ACGGCGCCTC TGACAGCAAC GTCTATGACC TCCTAAAGGA           350

CCTAGAGGAA GGCATCCAAA CGCTGATGGG GAGGCTGGAA GATGGCAGCC           400

CCTAG;
``` hGH (Met$^{-1}$Phe$^{191}$) antisense
(SEQ ID NO:21)

```
TACAAGGGTT GGTAAGGGAA TAGGTCCGAA AAACTGTTGC GATACGAGGC            50

GCGGGTAGCA GACGTGGTCG ACCGGAAACT GTGGATGGTC CTCAAACTTC           100

TTCGGATATA GGGTTTCCTT GTCTTCATAA GTAAGGACGT CTTGGGGGTC           150

TGGAGGGAGA CAAAGAGTCT CAGATAAGGC TGTGGGAGGT TGTCCCTCCT           200

TTGTGTTGTC TTTAGGTTGG ATCTCGACGA GGCGTAGAGG GACGACGAGT           250

AGGTCAGCAC CGACCTCGGG CACGTCAAGG AGTCCTCACA GAAGCGGTTG           300

TCGGACCACA TGCCGCGGAG ACTGTCGTTG CAGATACTGG AGGATTTCCT           350

GGATCTCCTT CCGTAGGTTT GCGACTACCC CTCCGACCTT CTACCGTCGG           400

GGGCCTGACC CGTCTAGAAG TTCGTCTGGA TGTCGTTCAA GCTGTGTTTG           450

AGTGTGTTGC TACTGCGTGA TGAGTTCTTG ATGCCCGACG AGATGACGAA           500

GTCCTTCCTG TACCTGTTCC AGCTCTGTAA GGACGCGTAG CACGTCACGG           550

CGAGACACCT CCCGTCGACA CCGAAGATC;
```

16K hGH (Met$^{-1}$Pro$^{133}$) antisense
(SEQ ID NO:22)

```
TACAAGGGTT GGTAAGGGAA TAGGTCCGAA AAACTGTTGC GATACGAGGC            50

GCGGGTAGCA GACGTGGTCG ACCGGAAACT GTGGATGGTC CTCAAACTTC           100

TTCGGATATA GGGTTTCCTT GTCTTCATAA GTAAGGACGT CTTGGGGGTC           150

TGGAGGGAGA GAAAGAGTCT CAGATAAGGC TGTGGGAGGT TGTCCCTCCT           200

TTGTGTTGTC TTTAGGTTGG ATCTCGACGA GGCGTAGAGG GACGACGAGT           250
```

-continued

```
AGGTCAGCAC CGACCTCGGG CACGTCAAGG AGTCCTCACA GAAGCGGTTG        300

TCGGACCACA TGCCGCGGAG ACTGTCGTTG CAGATACTGG AGGATTTCCT        350

GGATCTCCTT CCGTAGGTTT GCGACTACCC CTCCGACCTT CTACCGTCGG        400

GGATC;
``` hGH (Met⁻¹Phe¹⁹¹)

(SEQ ID NO:23)

```
MetPheProThrIleProLeuSerArgLeuPheAspAsnAlaMetLeuArgAlaHisArg
 -1         5          10          15

LeuHisGlnLeuAlaPheAspThrTyrGlnGluPheGluGluAlaTyrIleProLysGlu
 20         25         30          35

GlnLysTyrSerPheLeuGlnAsnProGlnThrSerLeuCysPheSerGlugerIlePro
 40         45         50          55

ThrProSerAsriArgGluGluThrGlnGlnLysSerAsnLeuGluLeuLeuArgIleSer
 60         65         70          75

LeuLeuLeuIleGlnSerTrpLeuGluProValGlnPheLeuArgSerValPheAlaAsn
 80         85         90          95

SerLeuValTyrGlyAlaSerAspSerAsnValTyrAspLeuLeuLysAspLeuGluGlu
100         105        110          115

GlyIleGlnThrLeuMetGlyArgLeuGluAspGlySerProArgThrGlyGlnIlePhe
120         125        130          135

LysGlnThrTyrSerLysPheAspThrAsnSerHisAsnAspAspAlaLeuLeuLysAsn
140         145        150          155

TyrGlyLeuLeuTyrCysPheArgLysAspMetAspLysValGluThrPheLeuArgIle
160         165        170          175

ValGlnCysArgSerValGluGlySerCysGlyPhe;
180         185        190
```

16K hGH (Met⁻¹Pro¹³³)

(SEQ ID NO:24)

```
MetPheProThrIleProLeuSerArgLeuPheAspAsnAlaMetLeuArgAlaHisArg
 -1         5          10          15

LeuHisGlnLeuAlaPheAspThrTyrGlnGluPheGluGluAlaTyrIleProLysGlu
 20         25         30          35

GlrlLysTyrSerPheLeuGlnAsnProGlnThrSerLeuSerPheSerGluSerIlePro
 40         45         50          55

ThrProSerAsnArgGluGluThrGlnGlnLysSerAsnLeuGluLeuLeuA.rgIleSer
 60         65         70          75

LeuLeuLeuIleGlnSerTrpLeuGluProValGlnPheLeuArgSerValPheAlaAsn
 80         85         90          95

SerLeuValTyrGlyAlaSerAspSerAsnValTyrAspLeuLeuLysAspLeuGluGlu
100         105        110          115

GlyIleGlnThrLeuMetGlyArgLeuGluAspGlySerPro;
120         125        130
``` hGH-V (Met⁻¹Phe¹⁹¹)

(SEQ ID NO:25)

```
ATGTTCCCAA CCATTCCCTT ATCCAGGCTT TTTGACAACG CTATGCTCCG         50

CGCCCGTCGC CTGTACCAGC TGGCATATGA CACCTATCAG GAGTTTGAAG        100

AAGCCTATAT CCTGAAGGAG CAGAAGTATT CATTCCTGCA GAACCCCCAG        150

ACCTCCCTCT GCTTCTCAGA GTCTATTCCA ACACCTTCCA ACAGGGTGAA        200

AACGCAGCAG AAATCTAACC TAGAGCTGCT CCGCATCTCC CTGCTGCTCA        250

TCCAGTCATG GCTGGAGCCC GTGCAGCTCC TCAGGAGCGT CTTCGCCAAC        300

AGCCTGGTGT ATGGCGCCTC GGACAGCAAC GTCTATCGCC ACCTGAAGGA        350

CCTAGAGGAA GGCATCCAAA CGCTGATGTG GAGGCTGGAA GATGGCAGCC        400
```

-continued

```
CCCGGACTGG GCAGATCTTC AATCAGTCCT ACAGCAAGTT TGACACAAAA         450

TCGCACAACG ATGACGCACT GCTCAAGAAC TACGGGCTGC TCTACTGCTT         500

CAGGAAGGAC ATGGACAAGG TCGAGACATT CCTGCGCATC GTGCAGTGCC         550

GCTCTGTGGA GGGCAGCTGT GGCTTCTAG;
```

16K hGH-V (Met$^{-1}$Arg$^{131}$)

(SEQ ID NO:26)
```
ATGTTCCCAA CCATTCCCTT ATCCAGGCTT TTTGACAACG CTATGCTCCG          50

CGCCCGTCGC CTGTACCAGC TGGCATATGA CACCTATCAG GAGTTTGAAG         100

AAGCCTATAT CCTGAAGGAG CAGAAGTATT CATTCCTGCA GAACCCCCAG         150

ACCTCCCTCT GCTTCTCAGA GTCTATTCCA ACACCTTCCA ACAGGGTGAA         200

AACGCAGCAG AAATCTAACC TAGAGCTGCT CCGCATCTCC CTGCTGCTCA         250

TCCAGTCATG GCTGGAGCCC GTGCAGCTCC TCAGGAGCGT CTTCGCCAAC         300

AGCCTGGTGT ATGGCGCCTC GGACAGCAAC GTCTATCGCC ACCTGAAGGA         350

CCTAGAGGAA GGCATCCAAA CGCTGATGTG GAGGCTGGAA GATGGCAGCC         400

CCCGGACTGG GCAGATCTTC AATCAGTCCT ACAGCAAGTT TGACACAAAA         450

TCGCACAACG ATGACGCACT GCTCAAGAAC TACGGGCTGC TCTACTGCTT         500

CAGGAAGGAC ATGGACAAGG TCGAGACATT CCTGCGCATC GTGCAGTGCC         550

GCTCTGTGGA GGGCAGCTGT GGCTTCTAG;
``` hGH-V (Met$^{-1}$Phe$^{191}$) antisense (SEQ ID NO:27)
```
TACAAGGGTT GGTAAGGGAA TAGGTCCGAA AAACTGTTGC GATACGAGGC          50

GCGGGCAGCG ACATGGTCG ACCGTATACT GTGGATAGTC CTCAAACTTC         100

TTCGGATATA GGACTTCCTC GTCTTCATAA GTAAGGACGT CTTGGGGGTC         150

TGGAGGGAGA CGAAGAGTCT CAGATAAGGT TGTGGAAGGT TGTCCCACTT         200

TTGCGTCGTC TTTAGATTGG ATCTCGACGA GGCGTAGAGG GACGACGAGT         250

AGGTCAGTAC CGACCTCGGG CACGTCGAGG AGTCCTCGCA GAAGCGGTTG         300

TCGGACCACA TACCGCGGAG CCTGTCGTTG CAGATAGCGG TGGACTTCCT         350

GGATCTCCTT CCGTAGGTTT GCGACTACAC CTCCGACCTT CTACCGTCGG         400

GGGCCTGACC CGTCTAGAAG TTAGTCAGGA TGTCGTTCAA ACTGTGTTTT         450

AGCGTGTTGC TACTGCGTGA CGAGTTCTTG ATGCCCGACG AGATGACGAA         500

GTCCTTCCTG TACCTGTTCC AGCTCTGTAA GGACGCGTAG CACGTCACGG         550

CGAGACACCT CCCGTCGACA CCGAAGATC;
```

16K hGH-V (Met$^{-1}$Arg$^{134}$)antisense (SEQ ID NO:28)
```
TACAAGGGTT GGTAAGGGAA TAGGTCCGAA AAACTGTTGC GATACGAGGC          50

GCGGGCAGCG ACATGGTCG ACCGTATACT GTGGATAGTC CTCAAACTTC         100

TTCGGATATA GGACTTCCTC GTCTTCATAA GTAAGGACGT CTTGGGGGTC         150

TGGAGGGAGA CGAAGAGTCT CAGATAAGGT TGTGGAAGGT TGTCCCACTT         200

TTGCGTCGTC TTTAGATTGG ATCTCGACGA GGCGTAGAGG GACGACGAGT         250

AGGTCAGTAC CGACCTCGGG CACGTCGAGG AGTCCTCGCA GAAGCGGTTG         300

TCGGACCACA TACCGCGGAG CCTGTCGTTG CAGATAGCGG TGGACTTCCT         350

GGATCTCCTT CCGTAGGTTT GCGACTACAC CTCCGACCTT CTACCGTCGG         400

GGGCCTGACC CGTCTAGAAG TTAGTCAGGA TGTCGTTCAA ACTGTGTTTT         450
```

```
AGCGTGTTGC TACTGCGTGA CGAGTTCTTG ATGCCCGACG AGATGACGAA        500

GTCCTTCCTG TACCTGTTCC AGCTCTGTAA GGACGCGTAG CACGTCACGG        550

CGAGACACGT CCCGTCGACA CCGAAGATC;
``` hGH-V (Met⁻¹Phe¹⁹¹)
(SEQ ID NO:29)
```
MetPheProThrIleProLeuSerArgLeuPheAspAsnAlaMetLeuArgAlaArgArg
 -1              5            10             15

LeuTyrGlnLeuAlaTyrAspThrTyrGlnGluPheGluGluAlaTyrIleLeuLysGlu
 20             25            30             35

GlnLysTyrSerPheLeuGlnAsnProGlnThrSerLeuCysPheSerGluSerIlePro
 40             45            50             55

ThrProSerAsnArgValLysThrGlnGlnLysSerAsnLeuGluLeuLeuArgIleSer
 60             65            70             75

LeuLeuLeuIleGlnSerTrpLeuGluProValGlnLeuLeuArgSerValPheAlaAsn
 80             85            90             95

SerLeuValTyrGlyAlaSerAspSerAsnValTyrArgHisLeuLysAspLeuGluGlu
100            105           110            115

GlyIleGlnThrLeuMetTrpArgLeuGluAspGlySerProArgThrGlyGlnIlePhe
120            125           130            135

AsnGlnSerTyrSerLysPheAspThrLysSerHisAsnAspAspAlaLeuLeuLysAsn
140            145           150            155

TyrGlyLeuLeuTyrCysPheArgLysAspMetAspLysValGluThrPheLeuArgIle
160            165           170            175

ValGlnCysArgSerValGluGlySerCysGlyPhe;
180            185           190
```

16K hGH-V (Met⁻¹Arg¹³⁴)
(SEQ ID NO:30)
```
MetPheProThrIleProLeuSerArgLeuPheAspAsriAlaMetLeuArgAlaArgArg
 -1              5            10             15

LeuTyrGlnLeuAlaTyrAspThrTyrGlnGluPheGluGluAlaTyrIleLeuLysGlu
 20             25            30             35

GlnLysTyrSerPheLeuGlnAsnProGlnThrSerLeuCysPheSerGluSerIlePro
 40             45            50             55

ThrProSerAsnArgValLysThrGlnGlnLysSerAsnLeuGluLeuLeuArgIleSer
 60             65            70             75

LeuLeuLeuIleGlnSerTrpLeuGluProValGlnLeuLeuArgSerValPheAlaAsn
 80             85            90             95

SerLeuValTyrGlyAlaSerAspSerAsnValTyrArgHisLeuLysAspLeuGluGlu
100            105           110            115

GlyIleGlnThrLeuMetTrpArgLeuGluAspGlySerProArg.
120            125           130
```

The sequences of the 16K N-terminal fragments were obtained by mutagenesis of the sequences of the intact hormones. Mutagenesis was performed using the oligonucleotide-directed mutagenesis kit purchased from either Amersham International (Buckinghamshire, UK) or Boehringer Mannheim (Mannheim, Germany). Oligonucleotides were purchased from Eurogentec S.A. (Seraing, Belgium).

The coding sequences were inserted into expression vector pT7L according to *J. Mol. Biol.*, 89:113-130 (1986). Plasmid constructions were made following standard techniques described in *Molecular Cloning, A Laboratory Manual*, Eds. Sambrook, Fritsch and Maniatis, Cold Spring Harbor Laboratory Press, Cold Spring Harbor, N.Y. (1992). Restriction enzymes and ligase were obtained from Eurogentec S. A. (Seraing, Belgium), Bethesda Research Laboratories (Gaithersburg, Md.) or Boehringer Mannheim (Mannheim, Germany).

Expression of the proteins was performed in *E. coli* BL21 (DE3). For purifications, Sephadex G100 or G75 gels (Pharmacia, Uppsala, Sweden) packed in C26 columns (2.6×100 cm, Pharmacia) and anion exchange MonoQ, Hitrap Q and Phenyl sepharose 6 fast flow columns (HR 10/10, Pharmacia) mounted on a FPLC system (Pharmacia) were used. Elution profiles were monitored by recording the absorbance at 280 nm.

EXAMPLE 4

Production of Human Prolactin

This example describes the procedure for preparation of intact full-length (23K) human prolactin.

The coding region for human prolactin (hPRL) minus the signal peptide was inserted into plasmid pT7L according to *Biotech. Applied Biochem.*, 12:436 (1990). An initiation codon ATG was added to the 51 end of the coding sequence of the hPRL deoxyribonucleotide sequence (denoted hPRL (Met$^{-1}$Cys$^{199}$)) (SEQ ID NO:1) and inserted into the pT7L *E. coli* expression vector. This plasmid was called pT7L-hPRL.

A 100 ml culture of *E. coli* BL21(DE3) carrying the pT7L-hPRL plasmid was grown overnight at 37° C. in LB, medium-ampicillin 100 µg/ml. Twenty ml of this culture were used to inoculate 1 liter of LB medium-ampicillin 100 µg/ml. When the O.D. (600 nm) reached 0.9, 1 mm isopropyl β-D thiogalactopyranoside (IPTG) was added to the culture. The induced culture was grown for an additional 4 hour period. Cells were collected by centrifugation at 5000 g for 15 min (4° C.) and resuspended in 50 mM Tris-HCl, 0.5 mM EDTA, ($T_{50}E_{0.5}$), 0.1 mM PMSF, pH 8. Cells were broken in a cell disrupter. After centrifugation of cell lysates (12,000 g; 15 min. 4° C.), hPRL was found in the insoluble fraction (inclusion bodies).

The inclusion bodies recovered in the pellet were washed 2 times in 250 ml of $T_{50}E_{0.5}$, 0.1 mM PMSF, pH 8. Inclusions bodies were solubilized in 200 mM phosphate buffer (pH 7) containing 8 M of deionized urea, 1% β-mercaptoethanol (β-ME), 0.5 mM PMSF at a concentration of 100 µg of protein per ml of buffer. The protein solution was heated at 55° C. for 5 min and then incubated overnight at room temperature. The renaturation was performed by a continued dialysis (72 hours) against 500 volumes of 50 mM NH$_4$HCO$_3$, pH 7.5.

The renatured protein was concentrated to 2 mg/ml and loaded on a Sephadex G100 column (50 mM NH$_4$HCO$_3$, pH 7.5) Fractions containing hPRL were pooled, dialyzed against 50 volumes of 20 mM Tris-HCl, pH 8 and loaded on a HitrapQ anion exchange column. Chromatography was performed in 20 mM Tris-HCl, pH 8 and hPRL was eluted within a gradient 0 to 1 M NaCl. Fractions containing purified hPRL were pooled, dialyzed against 20 mM NH$_4$HCO$_3$, pH 7.5 and lyophilized. The protein was purified to 95% homogeneity.

EXAMPLE 5

Production of the 16K N-terminal Fragment of Human Prolactin

This example describes the construction of plasmids coding for 3 different forms of 16K hPRL.

The 16K N-terminal fragment of human prolactin was produced by three different methods. The DNA sequences coding for the three different forms of 16K hPRL have been obtained by mutating the DNA of hPRL (cloned in the laboratory) (SEQ ID NO:1). The three different forms of 16K hPRL are called 16K hPRL (stop 124), 16K hPRL (stop 140) and 16K hPRL (IgA). All of the forms exhibit the same antiangiogenic activity.

To generate 16K hPRL (stop 124), two mutations were introduced in the hPRL coding sequence (16K hPRL (Met$^-$1Thr$^{123}$)) (SEQ ID NO:2). The Lys124 codon (AAA) was mutated to a stop codon (TAA); the Cys58 (TGC) into a Ser (TCC). The resulting plasmid was called pT7L-16K hPRL (stop 124). It encodes a protein called 16K hPRL (stop 124) which is composed of the 123 N-terminal amino acids of hPRL with the substitution of a Ser at position 58 instead of a Cys (SEQ ID NO:10).

To generate 16K hPRL (stop 140), two mutations were introduced in the hPRL cDNA (16K hPRL (Met$^{-1}$Pro$^{139}$)) (SEQ ID NO:3). The Glu 140 codon (GAA) was mutated in a stop codon (TGA); the Cys 58 (TGC) into a Ser (TCC). The resulting plasmid was called pT7L-16K hPRL (stop 140). It encodes a protein called 16K hPRL (stop 140) which is composed of the 139 N-terminal amino acids of hPRL with the substitution of a Ser at position 58 instead of a Cys (SEQ ID NO:11).

To obtain 16K hPRL (IgA) mutant, Cys 58 codon (TGC) was mutated to Ser codon (TCC) and the nucleotide sequence CCTGAAACCA AAGAAAAT (SEQ NO:31) coding for amino acids 139-144 ProGluThrLysGluAsn (SEQ ID NO:32) in hPRL was replaced by the nucleotide sequence CCTAGACCCC CAACACCT (SEQ ID NO:33) coding for the specific cleavage site of the IgA protease (ProArgProProThrPro) (SEQ ID NO:34). The resulting plasmid was called pT7L-hPRL (IgA). It encodes a protein called hPRL (IgA) which differs from hPRL at position 58 (Ser) and 140-144 (IgA specific cleavage site) (16K hPRL (Met$^{-1}$Pro$^{142}$)).

After cleavage of hPRL (IgA) by the IgA protease (between Pro 142 and Thr 143), the N-terminal fragment denoted 16K hPRL (IgA) is released. The latter was composed of the 142 N-terminal residues of hPRL with the substitution of a Ser at position 58 and ArgProPro at position 140-142 (SEQ ID NO:12).

To produce and purify 16K hPRL (stop 124) a 100 ml culture of *E. coli* BL21(DE3) carrying the pT7L-16K hPRL (stop 124) plasmid was grown overnight at 37° C. in LB medium-ampicillin 100 µg/ml. Twenty ml of this culture were used to inoculate 1 liter of LB medium-ampicillin 100 µg/ml. When the O.D. (600 nm) reached at 0.9, 1 mM isopropyl β-D thiogalactopyranoside (IPTG) was added to the culture. The induced culture was grown for an additional 4 hour period. Cells were collected by centrifugation at 5000 g for 15 min (4° C.) and resuspended in 50 mM Tris-HCl, 0.5 mM EDTA, ($T_{50}E_{0.5}$), 0.1 mM PMSF, pH 8. Cells were broken in a French Pressure cell Press (American Instrument Co.) at 13500 psi. After centrifugation of cell lysates (12,000 g, 15 min, 4° C.), 16K hPRL (stop124) was found in both soluble and insoluble fractions (inclusion bodies).

The inclusion bodies were recovered in the pellet and washed 2 times in 250 ml of $T_{50}E_{0.5}$, 0. 1 mM PMSF, pH 8. Inclusions bodies were solubilized in 200 mM phosphate buffer (pH 7) containing 8 M of deionized urea, 1% 0-ME, 0.5 mM PMSF at a concentration of 100 µg of protein per ml of buffer. The protein solution was heated at 55° C. for 5 min and then incubated overnight at room temperature. The renaturation was performed by a continued dialysis (72 hours) against 500 volumes of 50 mM NH$_4$HCO$_3$, pH 7.5.

The renatured protein was finally dialyzed against of 20 mM Tris-HCl, pH 8. After centrifugation at 5000 g to remove any precipitate, the supernatant was loaded on a MonoQ anion exchange column. Chromatography was performed in 20 mM Tris-HCl, pH 8 and 16K hPRL (stop124) was eluted within a gradient 0 to 1 M NaCl. Fractions containing 16K hPRL (stop124) were pooled and dialyzed against 50 mM NH$_4$HCO$_3$, pH 7.5. After centrifugation, supernatant was loaded on a Sephadex G75 column (50 mM NH₄HCO₃, pH 7.5). Fractions containing 16K hPRL (stop124) were pooled, dialyzed against 20 mM NH₄HCO₃, pH 7.5 and lyophilized.

Purification of the soluble fraction of 16K hPRL (stop 124) was performed. The supernatant obtained after centrifugation of cell lysate was fractionated with ammonium sulfate (4° C.). The precipitate obtained by the 10 to 40% fractionation was collected by centrifugation. The protein pellet corresponding to 1 liter of culture was resuspended in 50 ml of 50 mM NH₄HCO₃, pH 7.5 and dialyzed overnight (4° C.) against the same buffer containing 0.5 mM EDTA, 0.1 mM PMSF and 1 mM NaN3. After centrifugation, the 16K hPRL (stop124) was dialyzed against 50 mM NH₄HCO₃, pH 7.5. The protein was then concentrated to 2 mg/ml. The 16K hPRL (stop124) was denatured in 200 mM phosphate buffer, pH 7, containing 8 M of deionized urea, 1% β-ME, 0.5 mm PMSF.

The solution was heated at 55° C. for 5 min and then incubated overnight at room temperature. The denatured proteins were loaded on a Sephadex G10O column equilibrated in buffer containing 6 M deionized urea, 50 mM NH₄HCO₃, 5 mM β-ME, 0.5 mM PMSF, pH 7.5. Fractions containing 16K hPRL (stop124) were pooled, and renatured by continued dialysis (72 hours) against 500 volumes of 50 mM NH4HCO₃, pH 7.5.

Renatured proteins were finally dialyzed against 20 mM NH₄HCO₃, pH 7.5 and lyophilized. Degree of purity was between 90 and 95%.

The molecular mass of the 16K hPRL (stop124) was calculated from its amino acid sequence to be 13.9 kD.

To produce 16K hPRL (stop 140) an *E. coli* BL21(DE3) culture (100 ml) carrying the plasmid pT7L-16K hPRL (stop 140) was grown overnight at 37° C. into TB medium-ampicillin 100 μg/ml. Twenty ml of this culture was used to inoculate 1 liter of TB medium-ampicillin 100 μg/ml. When the O.D. (600 nm) reached at 0.9, 1 mM isopropyl β-D thiogalactopyranoside (IPTG) was added to the culture. The induced culture was grown for an additional 4 hour period.

Cells were collected by centrifugation at 5000 g for 15 min (4° C.) and resuspended in 50 mM Tris-HCl, 0.5 mM EDTA, ($T_{50}E_{0.5}$), 0.1 mM PMSF, pH 8. Cells were broken in a French Pressure Cell Press (American Instrument Co.) at 13500 psi. After centrifugation of cell lysates (12,000 g, 15 min, 4° C.), 16K hPRL (stop140) was found in the insoluble fraction (inclusion bodies). The latter were solubilized in 20 mM ethanolamine-HCl, pH 9, containing 8 M deionized urea, 1% β-ME, 0.5 mM PMSF at a ratio of 100 μg of protein per ml of buffer.

The solution was heated at 55° C. for 5 min and then incubated overnight at RT. The denatured proteins were dialyzed against 20 mM ethanolamine-HCl, pH 9, 6 M deionized urea. After centrifugation (5000 g; 15 min.), the proteins were applied for purification onto an anion exchange Hitrap Q column. Chromatography was performed in 20 mm ethanolamine-HCl, pH 9, 6 M deionized urea and 16K hPRL (stop140) was eluted within a gradient 0 to 1 M NaCl.

Fractions containing 16K hPRL (stop 140) were pooled, diluted with 20 mm ethanolamine-HCl, pH 9, 6 M deionized urea to a concentration of 0.1 mg/ml. For the renaturation, a continued dialysis was performed within a bath of 10 volumes of 20 mM ethanolamine-HCl, pH 9, 6 M deionized urea whose the urea was progressively removed by buffer exchange against 500 volumes of 20 mM ethanolamine, pH 9 for 72 hours. The renatured proteins were then dialyzed against 50 mM NH₄HCO₃, PH 7.5, 0.1 M NaCl. After concentration until 2 mg/ml, the proteins were loaded a Sephadex G100 column (50 mM NH₄HCO₃, pH 7.5, 0.1 M NaCl). Fractions containing the 16K hPRL (stop 140) were pooled, dialyzed against 20 mM NH₄HCO₃, pH 7.5 and lyophilized.

The molecular mass of the 16K hPRL (IRA) calculated from its amino acid sequence was 15.8 kD.

To produce 16K hPRL (IgA) an *E. coli* BL21(DE3) culture (100 ml) carrying the plasmid pT7L-hPRL (IgA) was grown overnight at 37° C. in LB medium-ampicillin 100 μg/ml. Twenty ml of this culture was used to inoculate 1 liter of LB medium-ampicillin 100 μg/ml. When the O.D. (600 nm) reached at 0.9, 1 mm isopropyl β-D thiogalactopyranoside (IPTG) was added to the culture. The induced culture was grown for an additional 4 hour period. Cells were collected by centrifugation at 5000 g for 15 min (4° C.) and resuspended in 50 mM Tris-HCl, 0.5 mM EDTA, ($T_{50}E_{0.5}$), 0.1 mM PMSF, pH 8. Cells were broken in a cell disrupter. After centrifugation of cell lysates (12,000 g, 15 min, (4° C.), 23K hPRL (IgA) was found in the insoluble fraction (inclusion bodies).

The inclusion bodies recovered in the pellet were washed 2 times in 250 ml of $T_{50}E_{0.5}$ 0.1 mM PMSF, pH 8. Inclusions bodies were solubilized in 200 mM phosphate buffer (pH 7) containing 8 M of deionized urea, 1% β-ME, 0.5 mM PMSF at a concentration of 100 gg of protein per ml of buffer. The protein solution was heated at 55° C. for 5 min and then incubated overnight at room temperature. The renaturation was performed by a continued dialysis (72 hours) against 500 volumes of 50 mM NH₄HCO₃, pH 7.5. After renaturation, the 23K hPRL (IgA) was dialyzed against 50 mM NH₄HCO₃, pH 7.5. For the digestion by IgA protease, the protein solution was concentrated to 1 mg/ml. The proteins were incubated 24 hours (25° C.) with 0.05% (w/w) of IgA protease (Boehringer Mannheim, Mannheim, Germany). The cleaved proteins were incubated for one hour with 1% β-ME before loading on a Sephadex G100 column (50 mM NH₄HCO₃, pH 7.5, 100 mM NaCl, 5 mM β-ME. Fractions containing 16K hPRL (IgA) were pooled, dialyzed against 20 mM Tris-HCl, pH 8 and loaded on a HitrapQ anion exchange column. Chromatography was performed in 20 mm Tris-HCl, pH 8 and 16K hPRL (IgA) was eluted within a gradient 0 to 1 M NaCl. Fractions containing purified 16K hPRL (IgA) were pooled, dialyzed against 20 mM NH₄HCO₃, pH 7.5 and lyophilized. Proteins were purified to 95% homogeneity.

The molecular mass of the 16K hPRL (IgA) calculated from its amino acid sequence was determined to be 16.1 kD.

EXAMPLE 6

Production of Intact Human Growth Hormone

This example describes a procedure for preparation of intact human growth hormone (hGH (Met⁻¹Phe¹⁹¹)) (SEQ ID NO:23).

The coding region for human growth hormone (hGH) minus the signal peptide was inserted into plasmid pT7L. An initiation codon ATG was added to the 5' end of the coding sequence of the hGH (Science, 205:602 (1979) (SEQ ID NO:19), and inserted into the pT7L *E. coli* expression vector. This plasmid was called pT7L-hGH.

A 100 ml culture of *E. coli* BL21(DE3) carrying the pT7L-hGH plasmid was grown at 37° C. in LB medium-ampicillin 100 μg/ml. Twenty ml of this culture were used to inoculate 1 liter of LB medium-ampicillin 100 μg/ml. When the O.D. (600 nm) reached at 0.9, 1 mM isopropyl β-D thiogalactopyranoside (IPTG) was added to the culture. The induced culture was grown for an additional 4 hour period. Cells were collected by centrifugation at 5000 g for 15 min (4° C.) and resuspended in 50 mM Tris-HCl, 0.5 mM EDTA, ($T_{50}E_{0.5}$), 0.1 mM PMSF, pH 8. Cells were broken in a cell disrupter. After centrifugation of cell lysates (12,000 g, 15 min, 4° C.), hGH was found in insoluble fractions (inclusion bodies).

The inclusion bodies recovered in the pellet were washed 2 times in 250 ml of $T_{50}E_{0.5}$, 0.1 mM PMSF, pH 8 and stored at −20° C. Inclusion bodies were solubilized in 20 mM ethanolamine, pH 9 containing 8 M of deionized urea, it β-ME, 0.5 mM PMSF at a concentration of 100 gg of protein per ml of buffer. The protein solution was heated at 55° C. for 5 min and then incubated overnight at room temperature. The renaturation was performed by a continued dialysis (72 hours) against 500 volumes of 20 mM ethanolamine, pH 9.

The renatured protein was loaded on a HitrapQ anion exchange column. Chromatography was performed in 20 mm ethanolamine, pH 9 and hGH was eluted within a gradient 0 to 1 M NaCl. Fractions containing hGH were pooled, concentrated to 2 mg/ml and loaded on a Sephadex G100 column (50 mM $NH_4HCO_3$, pH 7.5). Fractions containing purified hGH were pooled, dialyzed against 20 mM $NH_4HCO_3$, pH 7.5 and lyophilized proteins were purified to 90% homogeneity.

EXAMPLE 7

Purification of the 16K N-terminal Fragment of Human Growth Hormone

This example describes the procedure for preparation of the 16K N-terminal fragment of human growth hormone (16K hGH (Met$^{-1}$Pro$^{133}$)) (SEQ ID 24).

Two mutations were introduced in the hGH coding sequence. Cys 53 (TGT) was mutated to Ser (TCT) and Arg 134 (CGG) was mutated to a stop codon (TAG) (SEQ ID NO:20). The mutated cDNA was reinserted into the pT7L expression vector and called pT7L-16K hGH.

A E. coli BL21(DE3) culture (100 ml) carrying the plasmid pT7L-16K hGH was grown overnight at 37° C. into TB medium-ampicillin 100 µg/ml. Twenty ml of this culture was used to inoculate 1 liter of TB medium-ampicillin 100 µg/ml. When the O.D.600 reached at 0.6, 1 mM isopropyl β-D thiogalactopyranoside (IPTG) was added to the culture. The induced culture was grown for an additional 4 hour period. Cells were collected by centrifugation at 5000 g for 15 min (4° C.) and resuspended in 50 mM Tris-HCl, 0.5 mM EDTA, ($T_{50}E_{0.5}$), 0.1 mM PMSF, pH 8.

16K hGH was produced as an insoluble form (inclusion bodies). The latter were solubilized in 20 mM ethanolamine-HCl, pH 9, containing 8 M deionized urea, 1% β-ME. 0.5 mM PMSF (Buffer A) at a ratio of 100 µg of protein per ml of buffer. The solution was heated at 55° C. for 5 min and then incubated overnight at RT. The denatured proteins were dialyzed against 20 mM ethanolamine-HCl, pH 9, 6 M deionized urea. After centrifugation (5000 g; 15 min.), the proteins were applied for purification onto an anion exchange Hitrap Q column. Chromatography was performed in 20 mM ethanolamine-HCl, pH 9, 6 M deionized urea and 16K hGH was eluted within a gradient 0 to 1 M NaCl. Fractions containing 16K hGH were pooled, diluted with 20 mM ethanolamine-HCl, pH 9, 6 M deionized urea to a concentration of 0.1 mg/ml.

The renaturation was performed by a continued dialysis for 72 hours. For the renaturation, a continued dialysis was performed within a bath of 10 volumes of 20 mM ethanolamine-HCl, pH 9, 6 M deionized urea. The urea was progressively removed by buffer exchange against 500 volumes of 20 mM ethanolamine, pH 9 for 72 hours. The renatured proteins were then dialyzed against 50 mM $NH_4HCO_3$, pH 7.5, 0.1 M NaCl. After concentration to 2 mg/ml, the proteins were loaded a Sephadex G100 column (50 mM $NH_4HCO_3$, pH 7.5, 0.1 M NaCl). Fractions containing the 16K hGH were pooled, dialyzed against 20 mM $NH_4HCO_3$, pH 7.5 and lyophilized.

The molecular mass of the 16K hGH calculated from its amino acid sequence was determined to be 15.5 kD. Proteins were purified to 95% homogeneity.

EXAMPLE 8

Production of Intact Human Growth Hormone Variant hGH-V

This example describes a procedure for preparation of intact human growth:hormone variant hGH-V (hGH-V (Met$^{-1}$Phe$^{191}$)))(SEQ ID NO:2.9)

The coding region for hGH-V minus the signal peptide was inserted into a plasmid. The coding sequence for hGH-V was cloned by screening a placental cDNA library (Clonetech, HL 1008). An initiation codon ATG was added to the 51 end of the coding sequence of the hGH-V (SEQ ID NO:25) and inserted into the pT7L E. coli expression vector. This plasmid was called pT7L-hGH-V.

A 100 ml culture of E. coli BL21 (DE3) carrying the pT7L-hGH-V plasmid was grown overnight at 37° C. in LB medium-ampicillin 100 µg/ml. Twenty ml of this culture were used to inoculate 1 liter of LB medium-ampicillin 100 µg/ml. When the O.D. (600 nm) reached at 0.9, 1 mM isopropyl β-D thiogalactopyranoside (IPTG) was added to the culture. The induced culture was grown for an additional 4 hour period. Cells were collected by centrifugation at 5000 g for 15 min (4° C.) and resuspended in 50 mM Tris-HCl, 0.5 mM EDTA, ($T_{50}E_{0.5}$), 0.1 mM PMSF, pH 8. Cells were broken in a cell disrupter. After centrifugation of cell lysates (12,000 g, 15 min, 4° C.), hGH-V was found in the insoluble fraction (inclusion bodies).

The inclusion bodies recovered in the pellet were washed 2 times in 250 ml of $T_{50}E_{0.5}$ 0.1 mM PMSF, pH 8. Inclusion bodies were solubilized in 20 mM ethanolamine (pH 10) containing 8 M of deionized urea, 1% β-ME. 0.5 mM PMSF at a concentration of 100 µg of protein per ml of buffer. The protein solution was heated at 55° C. for 5 min and then incubated overnight at room temperature. The renaturation was performed by a continued dialysis (72 hours) against 500 volumes of 20 mM ethanolamine (pH 10).

The renatured protein was loaded on a HitrapQ anion exchange column. Chromatography was performed in 20 mM ethanolamine, pH 10 and hGH-V was eluted within a gradient of 0 to 1 M NaCl. Fractions containing hGH-V were pooled, concentrated to 2 mg/ml and loaded on a Sephadex G100 column (50 mM $NH_4HCO_3$, pH 9). Fractions containing purified hGH-V were pooled, dialyzed against 20 mM $NH_4HCO_3$, pH 9 and lyophilized. Proteins were purified to 95% homogeneity.

EXAMPLE 9

Purification of the 16K N-terminal Fragment of Human Growth Hormone Variant hGH-V This example describes the procedure for preparation of the 16K N-terminal fragment of human growth hormone variant hGH-V (16K hGH-V (Me$^{-1}$Arg$^{134}$)) (SEQ ID NO:30).

For production of 16K hGH-V, a natural cleavage site specific to thrombin is present at position Pro133-Arg134. Cleavage occurs after arginine 134. Human GH-V was produced and inclusion bodies denatured and renatured as described is Example 8. hGH-V was concentrated to 1 mg/ml and then enzymatically cleaved with thrombin (0.3%, 25° C. overnight, Sigma).

Purification was performed. The cleaved hGH-V was denatured in 20 mM ethanolamine-HCl, pH 9, 6 M deionized urea, 1% β-ME. 0.5 mM PMSF. After centrifugation (5000 g; 15 min.), the proteins were applied for purification onto a anion exchange Hitrap Q column. Chromatography was performed in 20 mM ethanolamine-HCl, pH 9, 6 M deionized urea, 5 mM β-ME and 16K hGH-V was eluted within a gradient 0 to 1 M NaCl. Fractions containing 16K hGH-V were pooled, diluted with 20 mm ethanolamine-HCl, pH 9, 6 M deionized urea to a concentration of 0.1 mg/ml.

The renaturation was performed by a continued dialysis for 72 hours. In order to remove the urea carefully, a first dialysis against 10 volumes of 20 mM ethanolamine-HCl, pH 9, 6 M deionized urea was performed. Second, the urea from this bath was removed by a continued dialysis against 500 volumes of 20 mM ethanolamine, pH 9. For the renaturation, a continued dialysis was performed within a bath of 10 volumes of 20 mM ethanolamine-HCl, pH 9, 6 M deionized urea whose the urea was progressively removed by buffer exchange against 500 volumes of 20 mM ethanolamine, pH 9 for 72 hours. The renatured proteins were then dialyzed against 50 mM NH$_4$HCO$_3$, pH 9, 0.1 M NaCl. After concentration to 2 mg/ml, the proteins were loaded a Sephadex G100 column (50 mM NH$_4$HCO$_3$, pH 9, 0.1 M NaCl). Fractions containing the 16K hGH-V were pooled, dialyzed against 20 mM NH$_4$HCO$_3$, pH 9 and lyophilized.

The molecular mass of the 16K hGH-V calculated from its amino acid sequence was determined to be 15.7 kD.

EXAMPLE 10

Production of Intact Human Placental Lactogen

This example describes a procedure preparation of intact human placental lactogen (hPL (Met$^{-1}$Phe$^{191}$)) (SEQ ID NO:17).

The coding sequence of the hPL was cloned using RT-PCR experiments performed on syncytiotrophoblastic cells. An initiation codon ATG was added to the 51 end of the coding sequence of the hPL (SEQ ID NO:13) and inserted into the pT7L E. coli expression vector. This recombinant plasmid was called pT7L-hPL.

A 100 ml culture of E. coli BL21 (DE3) carrying the pT7L-hPL plasmid was grown overnight at 37° C. in LB medium-ampicillin 100 µg/ml. Twenty ml of this culture were used to inoculate 1 liter of LB medium-ampicillin 100 µg/ml. When the O.D. (600 nm) reached at 0.9, 1 mM isopropyl β-D thiogalactopyranoside (IPTG) was added to the culture. The induced culture was grown for an additional 4 hour period. Cells were collected by centrifugation at 5000 g for 15 min (4° C.) and resuspended in 50 mM Tris-HCl, 0.5 mM EDTA, (T$_{50}$E$_{0.5}$), 0.1 mM PMSF, pH 8. Cells were broken in a cell disrupter. After centrifugation of cell lysates (12,000 g, 15 min, 4° C.), hPL was found in insoluble fraction (inclusion bodies).

The inclusion bodies recovered in the pellet were washed 2 times in 250 ml of T$_{50}$E$_{0.5}$, 0.1 mM PMSF, pH 8. Inclusions bodies were solubilized in 20 mM ethanolamine, pH 9 containing 8 M of deionized urea, 1% β-ME. 0.5 mM PMSF at a concentration of 100 g of protein per ml of buffer. The protein solution was heated at 55° C. for 5 min and then incubated overnight at room temperature. The renaturation was performed by a continued dialysis (72 hours) against 500 volumes of 20 mM ethanolamine, pH 9.

The renatured protein was loaded on a HitrapQ anion exchange column. Chromatography was performed in 20 mM ethanolamine, pH 9 and hPL was eluted within a gradient of 0 to 1 M NaCl. Fractions containing hPL were pooled, concentrated to 2 mg/ml and loaded on a Sephadex G100 column (50 mM NH$_4$HCO$_3$, pH 7.5)

Fractions containing purified hPL were pooled, dialyzed against 20 mM NH$_4$HCO$_3$, PH 7.5 and lyophilized. Proteins were purified to 95% homogeneity.

EXAMPLE 11

Purification of the 16K N-terminal Fragment of Human Placental Lactogen

This example describes the procedure for preparation of the 16K N-terminal fragment of human placental lactogen (16K hPL (Met$^{-1}$Arg$^{134}$)) (SEQ ID NO:18).

For production of 16K hPL, Cys 53 (TGC) was mutated to Ser (TCT) and Arg 134 (CGC) was mutated to Pro (CCC) in order to introduce a thrombin specific cleavage site (SEQ ID NO:14). The mutated cDNA was reinserted into the pT7L expression vector and called pT7L-16K hPL.

An E. coli BL21 (DE3) culture (100 ml) carrying the plasmid pT7L-16K hPL was grown overnight at 37° C. in LE medium-ampicillin 100 µg/ml. Twenty ml of this culture was used to inoculate 1 liter of LB medium-ampicillin 100 µg/ml. When the O.D. (600 nm) reached at 0.9, 1 mM isopropyl β-D thiogalactopyranoside (IPTG) was added to the culture. The induced culture was grown for an additional 4 hour period. Cells were collected by centrifugation at 5000 g for 15 min (4° C.) and resuspended in 50 mM Tris-HCl, 0.5 mM EDTA, (T$_{50}$E$_{0.5}$), 0.1 mM PMSF, pH 3. Cells were broken in a cell disrupter. After centrifugation of cell lysates (12,000 g, 15 min, (4° C.), mutated hPL was found in the insoluble fraction (inclusion bodies).

The inclusion bodies recovered in the pellet were washed 2 times in 250 ml of T$_{50}$E$_{0.5}$, 0.1 mM PMSF, pH 8 and stored at −20° C. Inclusions bodies were solubilized in 20 mm ethanolamine, pH 9 containing 8 M of deionized urea, it β-ME. 0.5 mM PMSF at a concentration of 100 gg of protein per ml of buffer. The protein solution was heated at 55° C. for 5 min and then incubated overnight at room temperature (RT). The renaturation was performed by a continued dialysis (72 hours) against 500 volumes of 20 mM ethanolamine, pH 9. The protein was then concentrated to 2 mg/ml and cleaved with thrombin overnight (0.3%, 25° C.).

The cleaved proteins were incubated for one hour with 1% β-ME before loading on a Sephadex G100 column (50 mM NH$_4$HCO$_3$, pH 7.5, 100 mM NaCl, 5 mM β-ME. Fractions containing 16K hPL were pooled, dialyzed against 50 mM Tris-HCl, pH 8, 20% NH$_2$SO$_4$ and loaded on a phenyl sepharose 6 fast flow hydrophobic column. Chromatography was performed in 50 mM Tris-HCl, pH 8 and 16K hPL was eluted within a gradient 20 to 0% of $NH_2SO_4$. Fractions containing purified 16K hPL were pooled, dialyzed against 20 mM $NH_4HCO_3$, pH 7.5 and lyophilized. Proteins were purified to 95% homogeneity.

The molecular mass of the 16K hPL calculated from its amino acid sequence was determined to be 15.6 kD.

EXAMPLE 12

Bovine grain Capillary Endothelial Cell Proliferation Assay

This example describes bovine brain capillary endothelial cell proliferation assay used for testing in vitro angiogenic activity of the peptides of the invention.

On day 1, $10^4$ BBCE cells prepared as described herein were plated onto 24 well plates (Nunc) in 0.25 ml of low glucose Dulbecco's modified Eagle's medium (Gibco) containing 10% fetal calf serum (Gibco), human bFGF (1 ng/ml, Promega) and concentrations of purified peptides from 0.1, 0.2, 0.5, 1, 2, 5, 10, 50 or 100 nM.

Wells containing 0.25 ml of medium well serum without bFGF were included as controls for basal growth. On day 3, bFGF (1 ng/ml) and purified peptides (0.1, 0.2, 0.5, 1, 2, 5, 10, 50 or 100 nM) were added once again to the dishes. On day 4, cells were incubated with 500,000 cpm of ($^3$H) thymidine with 0.6 µCi ($^3$H) thymidine (20.1 Ci/mmol; New England Nuclear), for 4 hours, washed in 5% trichloroacetic acid, solubilized in NaOH, and counted to method described in *Endocrinology*, 129:896 (1991). Each point represents the means of triplicate wells. The experiments were repeated at least three times, with similar results. Data seen in FIGS. 1 and 2 are represented as the percentage of bFGF-stimulation. Zero % is the level obtained for basal growth, whereas 100% is obtained when cell proliferation is induced by bFGF.

EXAMPLE 13

Preparation of Bovine Brain Capillary Endothelial Cells

This example illustrates preparation of bovine brain capillary endothelial cells for study of inhibitory effect of human 16K N-terminal fragments of lactogenic hormones.

Bovine brain capillary endothelial cells (BBCE) were isolated according to *J. Cell. Physiol.*, 127:121 (1986), and grown in low glucose Dulbecco's modified Eagle's medium containing 10 wt % calf serum, 2 mM glutamine, and 100 U/ml penicillin/streptomycin and 2.5 µg/ml fungizone.

Basic fibroblast growth factor (bFGF) was purified from bovine brain according to *P.N.A.S.* (USA) 81: 6963 (1984), and 1 ng/ml was then added to the BBCE cells every other day. Confluent cell cultures between passages 3-8 were used for the assays.

EXAMPLE 14

In Gel Mitogen Activated Protein Kinase Assay

This example describes in gel mitogen activated protein kinase MAPK assay.

The in gel MAPK assay was carried out essentially as previously described in *Proc. Natl. Acad. Sci. U.S.A.*, 92:6374 (1995).

Approximately 20 µg protein from BBCE cell lysates were electrophoresed through a 12.5% SDS-polyacrylamide gel containing 0.5 mg/ml of myelin basic protein (MBP) co-polymerized in the running gel. Following electrophoresis, the gel was washed twice each in buffer A (50 mM Tris pH 8, and 5 mM β-mercaptoethanol) containing 20% isopropyl alcohol, and denatured in buffer A containing 6 M guanidine HCl. After the guanidine HCl wash, the proteins in the gel were allowed to renature at 4° C. by extensive washing in buffer A containing 0.04% Tween 40. Renatured MBP kinase activity was detected by incubating the gel for 60 min at room temperature in a reaction buffer containing 40 mM HEPES (pH 7.4) 2 mM DTT, 15 mM $MgCl_2$, 300 µM sodium orthovanadate, 100 mM EGTA, 25 µM ATP and 100 µCi of ($\gamma$-$^{32}$P)ATP. Unincorporated radioactivity was removed by extensive washing in 5% trichloroacetic acid containing 1% tetrasodium pyrophosphate PPi. The gel was dried and exposed to X-ray film for 24 hours.

EXAMPLE 15

Phosphotyrosine Western for Mitogen Activated Protein Kinase

This example describes Western blot for detection of mitogen activated protein kinase (MAPK) used for determination of specificity of the receptors bind peptides of the invention.

Cellular proteins were resolved by SDS-PAGE (8%, 12% 12.5%) and transferred to nitrocellulose membranes (Schleicher & Schuell). Western blots were probed with the following antibodies: an anti-phosphotyrosine mouse monoclonal antibody (UBI, USA) (4G10, 1:2,000 dilution) and an anti-MAPK polyclonal antiserum that recognizes both p42 and p44 MAPK (erk 1-CT, 1:10,000 dilution) western blots were incubated with the appropriate antibody and then washed in Tris-buffered saline containing 0.5% Nonidet NP-40 and 0.1% Tween 20.

Antigen-antibody complexes were detected with horseradish peroxidase-coupled secondary antibodies using the Enhanced Chemiluminescence system (ECL, Amersham). The blots were exposed to Reflection NEF films (NEN). Western blots were stripped for reprobing with other primary antibodies by incubation for 30 min at 22° C. in a buffer containing 0.2 M glycine (pH 2.5) followed by two washes in PBS.

EXAMPLE 16

Western blot Analysis for Bovine Plasminogen Activator Inhibitor-i

This example describes the assay used for detection of inhibition of bovine plasminogen activator inhibitor-1 by peptides of the invention.

Cell homogenates or conditioned media from BBCE cells were resolved by SDS-PAGE (4-10%) and transferred to nitrocellulose membrane by semi-dry transfer apparatus. The transfer blots were stained with Ponceau Red for 1 min to visualize the even transfer of the proteins. The blots were blocked with 5% milk in Tris-buffered saline with 0.1% Tween 20 for 1 hour and incubated with anti-bovine PAI-1 mouse monoclonal antibody at a 1:2,000 dilution for 2 hours obtained from (Gibco Gaithersburg, Md.).

The antigen-antibody complexes were detected with horseradish peroxidase conjugated secondary antibody and the Enhanced Chemiluminescence system. The blots were exposed to reflection EF films (NEN) to visualize the bands.

EXAMPLE 17

Chick Chorioallantoic Membrane Assay

This example illustrates chick chorioallantoic membrane assay used for testing of in vivo inhibitory activity of peptides of the invention.

Chick embryos were placed in a Petri dish on day 3 of their development and cultured in a humidified incubator in an atmosphere of oxygen containing 2.5% $CO_2$ as described in *Nature,* 297:307 (1982). On day six, 5 mm disk of methylcellulose (0.5%, Sigma M0512) containing 20 µg of peptides of the invention and 2 µg bovine serum albumin (BSA) were laid on the advancing edge of the chick CAM as previously described in *Nature,* 297:307 (1982). After 48-h exposure, white India ink was injected into the chorioallantoic sac for photographic purpose.

All publications and patent applications cited in this specification are herein incorporated by reference in their entirety for all purposes as if each individual publication or patent application were specifically and individually indicated to be incorporated by reference.

As will be apparent to those skilled in the art to which the invention pertains, the present invention may be embodied in forms other than those specifically disclosed above, without departing from the spirit or essential characteristics of the invention. The particular embodiments of the invention described above, are, therefore to be considered as illustrative and not restrictive. The scope of the present invention is as set forth in the appended claims rather than being limited to the examples contained in the foregoing description.

What is claimed is:

1. An isolated peptide having the amino acid sequence of SEQ ID NO: 24.

2. A method of inhibiting angiogenesis in a patient, the method comprising administering to the patient an angiogenesis inhibitory effective amount of the isolated peptide of claim 1, wherein the patient has preeclampsia, intrauterine growth retardation, or placental dysfunction.

3. The isolated peptide of claim 1, wherein the peptide inhibits capillary endothelial cell proliferation and organization; inhibits angiogenesis in chick chorioallantoic membrane; and binds to at least one specific receptor which does not bind an intact full length growth hormone.

4. A method of treating an angiogenic disease in a subject, the method comprising administering to a subject in need of such treatment an angiogenesis inhibitory effective amount of an isolated peptide that has the amino acid sequence of SEQ ID NO:24.

5. A method of inhibiting tumor formation or growth in a patient, the method comprising administering to the patient an angiogenesis inhibitory effective amount of an isolated peptide that has the amino acid sequence of SEQ ID NO:24.

6. A pharmaceutical formulation, comprising:
   a pharmaceutically acceptable carrier; and
   a therapeutically effective amount of an isolated peptide that has the amino acid sequence of SEQ ID NO:24.

7. A method of treating a tumor, comprising:
   diagnosing a patient as having a tumor; and
   administering to the patient an angiogenesis inhibitory effective amount of the formulation of claim 6.

* * * * *

UNITED STATES PATENT AND TRADEMARK OFFICE
CERTIFICATE OF CORRECTION

| | | |
|---|---|---|
| PATENT NO. | : 7,300,920 B2 | Page 1 of 1 |
| APPLICATION NO. | : 10/714067 | |
| DATED | : November 27, 2007 | |
| INVENTOR(S) | : Richard I. Weiner et al. | |

It is certified that error appears in the above-identified patent and that said Letters Patent is hereby corrected as shown below:

On the title page, under "Other Publications" insert the following reference:

--Cunningham et al., Receptor and Antibody Epitopes in Human Growth Hormone Identified by Homolog-Scanning Mutagenesis, Science, 243:1330-1336, 1989.--

Signed and Sealed this

Twentieth Day of May, 2008

JON W. DUDAS
*Director of the United States Patent and Trademark Office*